(12) United States Patent
Brookings et al.

(10) Patent No.: US 7,521,460 B2
(45) Date of Patent: *Apr. 21, 2009

(54) THIENOPYRIDONE DERIVATIVES AS KINASE INHIBITORS

(75) Inventors: Daniel Christopher Brookings, Reading (GB); Jeremy Martin Davis, Wokingham (GB); Barry John Langham, Reading (GB)

(73) Assignee: UCB Pharma S.A., Brussels (BE)

( * ) Notice: Subject to any disclaimer, the term of this patent is extended or adjusted under 35 U.S.C. 154(b) by 210 days.

This patent is subject to a terminal disclaimer.

(21) Appl. No.: 10/561,052

(22) PCT Filed: Jun. 18, 2004

(86) PCT No.: PCT/GB2004/002621

§ 371 (c)(1),
(2), (4) Date: Oct. 10, 2006

(87) PCT Pub. No.: WO2004/113347

PCT Pub. Date: Dec. 29, 2004

(65) Prior Publication Data

US 2007/0099894 A1 May 3, 2007

(30) Foreign Application Priority Data

Jun. 20, 2003 (GB) .................................. 0314492.0
Dec. 19, 2003 (GB) .................................. 0329485.7

(51) Int. Cl.
*A01N 43/42* (2006.01)
*A61K 31/44* (2006.01)
*C07D 513/02* (2006.01)
*C07D 515/02* (2006.01)

(52) U.S. Cl. ...................................... 514/301; 546/114
(58) Field of Classification Search .................. 546/114; 514/301

See application file for complete search history.

(56) References Cited

U.S. PATENT DOCUMENTS

| 6,180,792 | B1 | 1/2001 | Furuya et al. | |
| 2006/0004025 | A1* | 1/2006 | Brookings et al. | ........ 514/260.1 |
| 2006/0025428 | A1 | 2/2006 | Brookings et al. | |
| 2006/0247269 | A1 | 11/2006 | Brookings et al. | |
| 2007/0078131 | A1 | 4/2007 | Alexander | |

FOREIGN PATENT DOCUMENTS

| WO | WO99/64400 | 12/1999 |
| WO | WO 03/033502 A1 | 4/2003 |
| WO | WO2004/000846 A1 | 11/2004 |

OTHER PUBLICATIONS

Fiebich et al., Journal of Immunology (2000), 165(10), pp. 5606-5611.*

Adams, J.L. et al., "p38 MAP kinase: molecular target for the inhibition of pro-inflammatory cytokines," *Progress in Medicinal Chemistry*, 2001, 38, 1-60.

Adhikari, R., et al., "An adventitious synthesis of 2,2'-dipyrryl disulfides," *Aust. J. Chem.*, 1999, 52, 63-67.

Allen, M. et al., "Deficiency of the stress kinase p38α results in embryonic lethality: characterization of the kinase dependence of stress responses of enzyme-deficient embryonic stem cells," *J. Exp. Med.*, 2000, 191, 859-869.

Badger, A.M., et al., "Pharmacological profile of SB 203580, a selective inhibitor of cytokine suppressive binding protein/p38 kinase, in animal models of arthritis, bone resorption, endotoxin shock and immune function," *J. Pharm. Exp. Ther.*, 1996, 279(3), 1453-1461.

Chan, D.T. et al., "New N-andO-arylations with phenylboronic acids and cupric acetate," *Tetrahedron Letters*, 1998, 39, 2933-2936.

Cohen, P., "The search for physiological substrates of MAP and SAP kinases in mammalian cells," *Trends Cell Biol*, 1997, 7, 353-361.

Dinarello, C.A., "An update on human interleukin-1: from molecular biology to clinical relevance," *J. Clinical Immunology*, 1985, 5(5), 287-297.

Doza, Y.N., et al., "Activation of the MAP kinase homologue RK requires the phosphorylation of Thr-180 and Tyr-182 and both resides are phosphorylated in chemically stressed KB cells," *FEBS Lett.*, 1995, 364, 223-228.

Enslen, H. et al., "Selective activation of p38 mitogen-activated protein (MAP) kinase isoforms by the MAP kinase kinases MKK3 and MKK6," *J. Biol. Chem.*, 1998, 273, 1741-1748.

Hale, K.K. et al., "Differential expression and activation of p38 mitogen-activated protein kinase α, β, γ, and δ in inflammatory cell lineages," *J. Immun.*, 1999, 162, 4246-4252.

Hartwig, J.F., "Transition metal catalyzed synthesis of arylamines and aryl ethers from aryl halides and triflates: scope and mechanism," *Agnew Chem. Int. Ed. Engl.*, 1998, 37, 2046-2067.

Hedayatullah, M., "Alkylation des pyrimidines en catalyse par transfert de phase," *J. Heterocyclic Chem.*, 1981, 18, 339-342 (no English Abstract).

Hunter, T., "Protein kinase classification," *Methods in Enzymology*, 1991, vol. 200, Academic Press, San Diego, p. 3.

Jiang, Y., Characterization of the structure and function of a new mitogen-activated protein kinase (p38β) et al., *J. Biol. Chem.*, 1996, 271(30), 17920-17926.

Konno, et al., "Improved procedures for preparation of 2-pyridones and 2-hydroxymethylpyridines from pyridine N-oxides," *Heterocycles*, 1986, 24(8), 2169-2171.

Kotlyarov, A. et al., "MAPKAP kinase 2 is essential for LPS-induced TNF-α biosynthesis," *Nature Cell Biol.*, 1999, 1, 94-97.

(Continued)

*Primary Examiner*—Janet L Andres
*Assistant Examiner*—Niloofar Rahmani
(74) *Attorney, Agent, or Firm*—McDonnell Boehnen Hulbert & Berghoff LLP

(57) ABSTRACT

A series of thieno[2,3-b]pyridin-6(7H)-one derivatives, substituted in the 2-position by a carbonyl- or sulfonyl-linked pyrrolidin-1-yl or related moiety, being inhibitors of p38 MAP kinase, are accordingly of use in medicine, for example in the treatment and/or prevention of immune or inflammatory disorders.

11 Claims, No Drawings

OTHER PUBLICATIONS

Lee, J.C. et al., "Bicyclic imidazoles as a novel class of cytokine biosynthesis inhibitors," *Annals N.Y. Acad Sci.*, 1993, 696, 149-170.

Lee, J.C. et al., "Inhibition of monocyte IL-1 production by the anti-inflammatory compound, SK&F 86002," *Int. J. Immunopharm*, 1988, 10(7), 835-843.

Lee, J.C. et al., "A protein kinase involved in the regulation of inflammatory cytokine biosynthesis," *Nature*, 1994, 372, 739-746.

Luker, T.J., et al., "Palladium catalysed amination of electron deficient halopthiophenes," *Tetrahedron Lett.*, 2001, 41, 7731-7735.

McDonnell, P.C. et al., Localization of the human stress responsive MAP kinase-like CSAIDs binding protein (CSBP) gene to chromosome 6p21.3/21.2, *Genomics*, 1995, 29, 301-302.

Sont, J.K., et al., "Fully automated assessment of inflammatory cell counts and cytokine expression in bronchial tissue," *Am. J. Respir. Crit. Care Med.*, 2003, 167, 1496-1503.

Subauste, M.C., et al., "Infection of a human respiratory epithelial cell line with rhinovirus," *J. Clin. Invest.*, 1995, 96, 549-557.

Takekawa, M. et al., "A family of stress-inducible GADD45-like proteins mediate activation of the stress-responsive MTK1/MEKK4 MAPKKK," *Cell*, 1998, 95, 521-530.

Teran, L.M., et al., "Role of nasal interleukin-8 in neutrophil recruitment and activation in children with virus-induced asthma," *Am. J. Respir. Crit. Care Med.*, 1997, 155, 1362-1366.

Turner, R.B., et al., "Association between interleukin-8 concentration in nasal secretions and severity of symptoms of experimental rhinovirus colds," *Clin. Infec. Dis.*, 1998, 26, 840-846.

Wolfe, J.P., et al., "Scope and limitations of the Pd/BINAP-catalyzed amination of aryl bromides," *J. Org. Chem.*, 2000, 65, 1144-1157.

Zhu, Z., et al., "Rhinovirus stimulation of interleukin-6 in vivo and in vitro," *J. Clin. Invest.*, 1996, 97, 421-430.

* cited by examiner

THIENOPYRIDONE DERIVATIVES AS KINASE INHIBITORS

This invention relates to a series of thienopyridone derivatives, to compositions containing them, to processes for their preparation and to their use in medicine.

Immune and inflammatory responses involve a variety of cell types with control and co-ordination of the various interactions occurring via both cell-cell contacts (e.g. integrin interactions with their receptors) and by way of intercellular signalling molecules. A large number of different signalling molecules are involved, including cytokines, lymphocytes, chemokines and growth factors.

Cells respond to such intercellular signalling molecules by means of intracellular signalling mechanisms that include protein kinases, phosphatases and phospholipases. There are five classes of protein kinase of which the major ones are the tyrosine kinases and the serine/threonine kinases [Hunter, T., Methods in Enzymology (Protein Kinase Classification), p. 3, Hunter, T. and Sefton, B. M. eds., vol. 200, Academic Press, San Diego, 1991].

One sub-class of serine/threonine kinases is the mitogen activating protein (MAP) kinases of which there are at least three families which differ in the sequence and size of the activation loop [Adams, J. L. et al., Progress in Medicinal Chemistry, pp. 1-60, King, F. D. and Oxford, A. W. eds., vol. 38, Elsevier Science, 2001]: (i) the extracellular regulated kinases (ERKs); (ii) the c-Jun $NH_2$ terminal kinases or stress activated kinases (JNKs or SAP kinases); and (iii) the p38 kinases which have a threonine-glycine-tyrosine (TGY) activation motif. Both the JNKs and p38 MAP kinases are primarily activated by stress stimuli including, but not limited to, proinflammatory cytokines, e.g. tumour necrosis factor (TNF) and interleukin-1 (IL-1), ultraviolet light, endotoxin and chemical or osmotic shock.

Four isoforms of p38 have been described (p38α/β/γ/δ). The human p38α enzyme was initially identified as a target of cytokine-suppressive anti-inflammatory drugs (CSAIDs) and the two isoenzymes found were initially termed CSAID binding protein-1 (CSBP-1) and CSBP-2 [Lee, J. C. et al., Nature (London), 1994, 372, 739-46]. CSBP-2 is now widely referred to as p38α and differs from CSBP-1 in an internal sequence of 25 amino acids as a result of differential splicing of two exons that are conserved in both mouse and human [McDonnell, P. C. et al., Genomics, 1995, 29, 301-2]. CSBP-1 and p38α are expressed ubiquitously and there is no difference between the two isoforms with respect to tissue distribution, activation profile, substrate preference or CSAID binding. A second isoform is p38β which has 70% identity with p38α. A second form of p38β termed p38β2 is also known and of the two this is believed to be the major form. p38α and p38β2 are expressed in many different tissues. However in monocytes and macrophages p38α is the predominant kinase activity [Lee, J. C., ibid; Jing, Y. et al., J. Biol. Chem., 1996, 271, 10531-34; Hale, K. K. et al., J. Immun., 1999, 162, 4246-52]. p38γ and p38δ (also termed SAP kinase-3 and SAP kinase-4 respectively) have ~63% and ~61% homology to p38α respectively. p38γ is predominantly expressed in skeletal muscle whilst p38δ is found in testes, pancreas, prostate, small intestine and in certain endocrine tissues.

All p38 homologues and splice variants contain a 12 amino acid activation loop that includes a Thr-Gly-Tyr motif. Dual phosphorylation of both Thr-180 and Tyr-182 in the TGY motif by a dual specificity upstream kinase is essential for the activation of p38 and results in a >1000-fold increase in specific activity of these enzymes [Doza, Y. N. et al., FEBS Lett., 1995, 364, 7095-8012]. This dual phosphorylation is effected by MKK6 and under certain conditions the related enzyme MKK3 [Enslen, H. et al., J. Biol. Chem., 1998, 273, 1741-48]. MKK3 and MKK6 belong to a family of enzymes termed MAPKK (mitogen activating protein kinase kinase) which are in turn activated by MAPKKK (mitogen activating kinase kinase kinase) otherwise known as MAP3K.

Several MAP3Ks have been identified that are activated by a wide variety of stimuli including environmental stress, inflammatory cytokines and other factors. MEKK4/MTK1 (MAP or ERK kinase kinase/MAP three kinase-1), ASK1 (apoptosis stimulated kinase) and TAK1 (TGF-β-activated kinase) are some of the enzymes identified as upstream activators of MAPKKs. MEKK4/MTK1 is thought to be activated by several GADD-45-like genes that are induced in response to environmental stimuli and which eventually lead to p38 activation [Takekawa, M. and Saito, H., Cell, 1998, 95, 521-30]. TAK1 has been shown to activate MKK6 in response to transforming growth factor-β (TGF-β). TNF-stimulated activation of p38 is believed to be mediated by the recruitment of TRAF2 [TNF receptor associated factor] and the Fas adaptor protein, Daxx, which results in the activation of ASK1 and subsequently p38.

Several substrates of p38 have been identified including other kinases [e.g. MAPK activated protein kinase 2/3/5 (MAPKAP 2/3/5), p38 regulated/activated protein kinase (PRAK), MAP kinase-interacting kinase 1/2 (MNK1/2), mitogen- and stress-activated protein kinase 1 (MSK1/RLPK) and ribosomal S6 kinase-B (RSK-B)]; transcription factors [e.g. activating transcription factor 2/6 (ATF2/6), monocyte-enhancer factor-2A/C (MEF2A/C), C/EBP homologous protein (CHOP), Elk1 and Sap-1a1]; and other substrates [e.g. cPLA2, p47phox].

MAPKAP K2 is activated by p38 in response to environmental stress. Mice engineered to lack MAPKAP K2 do not produce TNF in response to lipopolysaccharide (LPS). Production of several other cytokines such as IL-1, IL-6, IFN-g and IL-10 is also partially inhibited [Kotlyarov, A. et al., Nature Cell Biol., 1999, 1, 94-7]. Further, MAPKAP K2 from embryonic stem cells from p38α null mice was not activated in response to stress and these cells did not produce IL-6 in response to IL-1 [Allen, M. et al., J. Exp. Med., 2000, 191, 859-69]. These results indicate that MAPKAP K2 is not only essential for TNF and IL-1 production but also for signalling induced by cytokines. In addition MAPKAP K2/3 phosphorylate and thus regulate heat shock proteins HSP 25 and HSP 27 which are involved in cytoskeletal reorganization.

Several small molecule inhibitors of p38 have been reported which inhibit IL-1 and TNF synthesis in human monocytes at concentrations in the low μM range [Lee, J. C. et al., Int. J. Immunopharm., 1988, 10, 835] and exhibit activity in animal models which are refractory to cyclooxygenase inhibitors [Lee, J. C. et al., Annals N. Y. Acad. Sci., 1993, 696, 149]. In addition these small molecule inhibitors are known to decrease the synthesis of a wide variety of pro-inflammatory proteins including IL-6, IL-8, granulocyte/macrophage colony-stimulating factor (GM-CSF) and cyclooxygenase-2 (COX-2). TNF-induced phosphorylation and activation of cytosolic PLA2, TNF-induced expression of VCAM-1 on endothelial cells and IL-1 stimulated synthesis of collagenase and stromelysin are also inhibited by small molecule inhibitors of p38 [Cohen, P., Trends Cell Biol., 1997, 7, 353-61].

A variety of cells including monocytes and macrophages produce TNF and IL-1. Excessive or unregulated TNF production is implicated in a number of disease states including Crohn's disease, ulcerative colitis, pyresis, rheumatoid arthritis, rheumatoid spondylitis, osteoarthritis, gouty arthritis and other arthritic conditions, toxic shock syndrome, endotoxic shock, sepsis, septic shock, gram negative sepsis, bone resorption diseases, reperfusion injury, graft vs. host reaction, allograft rejection, adult respiratory distress syndrome, chronic pulmonary inflammatory disease, silicosis, pulmonary sarcoidosis, cerebral malaria, scar tissue formation, keloid formation, fever and myalgias due to infection, such as influenza, cachexia secondary to acquired immune deficiency syndrome (AIDS), cachexia secondary to infection or malignancy, AIDS or AIDS related complex.

Excessive or unregulated IL-1 production has been implicated in rheumatoid arthritis, osteoarthritis, traumatic arthritis, rubella arthritis, acute synovitis, psoriatic arthritis, cachexia, Reiter's syndrome, endotoxemia, toxic shock syndrome, tuberculosis, atherosclerosis, muscle degeneration, and other acute or chronic inflammatory diseases such as the inflammatory reaction induced by endotoxin or inflammatory bowel disease. In addition IL-1 has been linked to diabetes and pancreatic β cell destruction [Dinarello, C. A., *J. Clinical Immunology*, 1985, 5, 287-97].

IL-8 is a chemotactic factor produced by various cell types including endothelial cells, mononuclear cells, fibroblasts and keratinocytes. IL-1, TNF and LPS all induce the production of IL-8 by endothelial cells. In vitro IL-8 has been shown to have a number of functions including being a chemoattractant for neutrophils, T-lymphocytes and basophils. IL-8 has also been shown to increase the surface expression of Mac-1 (CD11b/CD18) on neutrophils without de novo protein synthesis which may contribute to increased adhesion of neutrophils to vascular endothelial cells. Many diseases are characterised by massive neutrophil infiltration. Histamine release from basophils (in both atopic and normal individuals) is induced by IL-8 as is lysozomal enzyme release and respiratory burst from neutrophils.

The central role of IL-1 and TNF together with other leukocyte derived cytokines as important and critical inflammatory mediators is well documented. The inhibition of these cytokines has been shown or would be expected to be of benefit in controlling, alleviating or reducing many of these disease states.

The central position that p38 occupies within the cascade of signalling molecules mediating extracellular to intracellular signalling and its influence over not only IL-1, TNF and IL-8 production but also the synthesis and/or action of other pro-inflammatory proteins (e.g. IL-6, GM-CSF, COX-2, collagenase and stromelysin) make it an attractive target for inhibition by small molecule inhibitors with the expectation that such inhibition would be a highly effective mechanism for regulating the excessive and destructive activation of the immune system. Such an expectation is supported by the potent and diverse anti-inflammatory activities described for p38 kinase inhibitors [Adams, ibid; Badger et al., *J. Pharm. Exp. Ther.*, 1996, 279, 1453-61; Griswold et al., *Pharmacol. Comm.*, 1996, 7, 323-29].

We have now found a group of compounds which are potent and selective inhibitors of p38 kinase (p38α, β, δ and γ) and the isoforms and splice variants thereof, especially p38α, p38β and p38β2. The compounds are thus of use in medicine, for example in the prophylaxis and treatment of immune or inflammatory disorders as described herein.

Thus according to one aspect of the invention we provide a compound of formula (1):

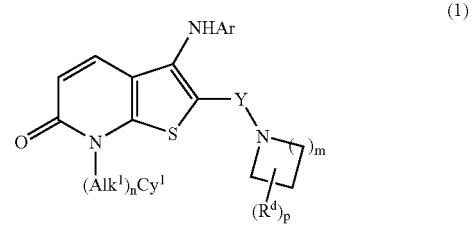

wherein:
Y is a linking group —C(O)— or —S(O)$_2$—;
n is zero or the integer 1;
m is the integer 1, 2, 3 or 4;
p is the integer 1, 2, 3 or 4;
$R^d$ is an —OH, -(Alk$^2$)OH (where Alk$^2$ is a straight or branched C$_{1-4}$ alkylene chain), —OR$^1$ (where R$^1$ is a straight or branched C$_{1-6}$ alkyl group), -(Alk$^2$)OR$^1$, —NR$^2$R$^3$ (where R$^2$ and R$^3$ may be the same or different and is each independently a hydrogen atom or a straight or branched C$_{1-6}$ alkyl group), -(Alk$^2$)NR$^2$R$^3$ or straight or branched C$_{1-6}$ alkyl group;
Alk$^1$ is a straight or branched C$_{1-4}$ alkylene chain;
Cy$^1$ is an optionally substituted cycloaliphatic, aromatic or heteroaromatic group; and
Ar is an optionally substituted aromatic or heteroaromatic group;
and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof in any proportion, including racemates. Formula (1) and the formulae hereinafter are intended to represent all individual isomers and mixtures thereof, unless stated or shown otherwise. In addition, compounds of formula (1) may exist as tautomers, for example keto (CH$_2$C=O)-enol (CH=CHOH) tautomers. Formula (1) and the formulae hereinafter are intended to represent all individual tautomers and mixtures thereof, unless stated otherwise.

The following general terms as used herein in relation to compounds of the invention and intermediates thereto have the stated meaning below unless specifically defined otherwise.

Thus as used herein the term "alkyl" whether present as a group or part of a group includes straight or branched C$_{1-6}$ alkyl groups, for example C$_{1-4}$ alkyl groups such as methyl, ethyl, n-propyl, isopropyl, n-butyl, sec-butyl, isobutyl or tert-butyl groups. Similarly, the terms "alkenyl" or "alkynyl" are intended to mean straight or branched C$_{2-6}$ alkenyl or C$_{2-6}$ alkynyl groups such as C$_{2-4}$ alkenyl or C$_{2-4}$ alkynyl groups. The optional substituents which may be present on these groups include one, two, three or more substituents where each substituent may be the same or different and is selected from halogen atoms, e.g. fluorine, chlorine, bromine or iodine atoms, or —OH, —CO$_2$H, —CO$_2$R$^4$ [where R$^4$ is an optionally substituted straight or branched C$_{1-6}$ alkyl group, and is in particular a straight or branched C$_{1-4}$ alkyl group], e.g. —CO$_2$CH$_3$ or —CO$_2$C(CH$_3$)$_3$, —CONHR$^4$, e.g. —CONHCH$_3$, —CON(R$^4$)$_2$, e.g. —CON(CH$_3$)$_2$, —COR$^4$, e.g. —COCH$_3$, C$_{1-6}$ alkoxy, e.g. methoxy or ethoxy, haloC$_{1-6}$ alkoxy, e.g. trifluoromethoxy or difluoromethoxy, thiol (—SH), —S(O)R$^4$, e.g. —S(O)CH$_3$, —S(O)$_2$R$^4$, e.g. —S(O)$_2$CH$_3$, C$_{1-6}$ alkylthio, e.g. methylthio or ethylthio, amino, —NHR⁴, e.g. —NHCH₃, or —N(R⁴)₂, e.g. —N(CH₃)₂, groups. Where two R⁴ groups are present in any of the above substituents these may be the same or different.

In addition when two R⁴ alkyl groups are present in any of the optional substituents just described these groups may be joined, together with the N atom to which they are attached, to form a heterocyclic ring. Such heterocyclic rings may be optionally interrupted by a further heteroatom or heteroatom-containing group selected from —O—, —S—, —N(R⁴)—, —C(O)— or —C(S)— groups. Particular examples of such heterocyclic rings include piperidinyl, pyrazolidinyl, morpholinyl, thiomorpholinyl, pyrrolidinyl, imidazolidinyl and piperazinyl rings.

The term halogen is intended to include fluorine, chlorine, bromine or iodine atoms.

The term "haloalkyl" is intended to include those alkyl groups just mentioned substituted by one, two or three of the halogen atoms just described. Particular examples of such groups include —CF₃, —CCl₃, —CHF₂, —CHCl₂, —CH₂F and —CH₂Cl groups.

The term "alkoxy" as used herein is intended to include straight or branched $C_{1-6}$ alkoxy, e.g. $C_{1-4}$ alkoxy such as methoxy, ethoxy, n-propoxy, isopropoxy, n-butoxy, sec-butoxy, isobutoxy and tert-butoxy. "Haloalkoxy" as used herein includes any of these alkoxy groups substituted by one, two or three halogen atoms as described above. Particular examples include —OCF₃, —OCCl₃, —OCHF₂, —OCHCl₂, —OCH₂F and —OCH₂Cl groups.

As used herein the term "alkylthio" is intended to include straight or branched $C_{1-6}$ alkylthio, e.g. $C_{1-4}$ alkylthio such as methylthio or ethylthio.

As used herein the term "alkylamino" or "dialkylamino" is intended to include the groups —NHR$^{1a}$ and —N(R$^{1a}$)(R$^{1b}$) where R$^{1a}$ and R$^{1b}$ is each independently an optionally substituted straight or branched alkyl group or both together with the N atom to which they are attached form an optionally substituted heterocycloalkyl group which may contain a further heteroatom or heteroatom-containing group such as an —O— or —S— atom or —N(R$^{1a}$)— group. Particular examples of such optionally substituted heterocycloalkyl groups include optionally substituted pyrrolidinyl, piperidinyl, morpholinyl, thiomorpholinyl and N'-$C_{1-6}$alkylpiperazinyl groups. The optional substituents which may be present on such heterocycloalkyl groups include those optional substituents as described above in relation to the term "alkyl".

Particular examples of alkylene chains represented by Alk¹ and/or Alk² when each is present in compounds of the invention include —CH₂—, —CH₂CH₂—, —CH(CH₃)CH₂—, —(CH₂)₂CH₂—, —C(CH₃)₂—, —(CH₂)₃CH₂—, —CH₂CH(CH₃)CH₂—, —C(CH₃)₂CH₂— or —CH(CH₃)CH₂CH₂— chains.

Optionally substituted cycloaliphatic groups represented by the group Cy¹ in compounds of the invention include optionally substituted $C_{3-10}$ cycloaliphatic groups. Particular examples include optionally substituted $C_{3-10}$ cycloalkyl, e.g. $C_{3-7}$ cycloalkyl, or $C_{3-10}$ cycloalkenyl, e.g. $C_{3-7}$ cycloalkenyl, groups.

Particular examples of cycloaliphatic groups represented by the group Cy¹ include optionally substituted cyclopropyl, cyclobutyl, cyclopentyl, cyclohexyl, cycloheptyl, 2-cyclobuten-1-yl, 2-cyclopenten-1-yl and 3-cyclopenten-1-yl groups, especially cyclopropyl.

The optional substituents which may be present on the cycloaliphatic groups represented by the group Cy₁ include one, two, three or more substituents selected from halogen atoms, or $C_{1-6}$ alkyl, e.g. methyl or ethyl, halo$C_{1-6}$alkyl, e.g. halomethyl or haloethyl such as difluoromethyl or trifluoromethyl, optionally substituted by hydroxyl, e.g. —C(OH)(CF₃)₂, $C_{1-6}$ alkoxy, e.g. methoxy or ethoxy, halo$C_{1-6}$alkoxy, e.g. halomethoxy or haloethoxy such as difluoromethoxy or trifluoromethoxy, thiol, $C_{1-6}$ alkylthiol, e.g. methylthiol or ethylthiol, carbonyl (═O), thiocarbonyl (═S), imino (═NR$^{4a}$) [where R$^{4a}$ is an —OH group or a $C_{1-6}$ alkyl group], or -(Alk³)ᵥR⁵ groups in which Alk³ is a straight or branched $C_{1-3}$alkylene chain, v is zero or the integer 1 and R⁵ is a $C_{3-8}$ cycloalkyl, —OH, —SH, —N(R⁶)(R⁷) [in which R⁶ and R⁷ is each independently selected from a hydrogen atom or an optionally substituted alkyl or $C_{3-8}$ cycloalkyl group], —OR⁶, —SR⁶, —CN, —NO₂, —CO₂R⁶, —SOR⁶, —SO₂R⁶, —SO₃R⁶, —OCO₂R⁶, —C(O)R⁶, —OC(O)R⁶, —C(S)R⁶, —C(O)N(R⁶)(R⁷), —OC(O)N(R⁶)(R⁷), —N(R⁶)C(O)R⁷, —C(S)N(R⁶)(R⁷), —N(R⁶)C(S)R⁷, —SO₂N(R⁶)(R⁷), —N(R⁶)SO₂R⁷, —N(R⁶)C(O)N(R⁷)(R⁸) [where R⁸ is as defined for R⁶], —N(R⁶)C(S)N(R⁷)(R⁸), —N(R⁶)SO₂N(R⁷)(R⁸) or an optionally substituted aromatic or heteroaromatic group.

Particular examples of Alk³ chains include —CH₂—, —CH₂CH₂—, —CH₂CH₂CH₂— and —CH(CH₃)CH₂— chains.

When R⁵, R⁶, R⁷ and/or R⁸ is present as a $C_{3-8}$ cycloalkyl group it may be for example a cyclopropyl, cyclobutyl, cyclopentyl or cyclohexyl group. Optional substituents which may be present on such groups include for example one, two or three substituents which may be the same or different selected from halogen atoms, for example fluorine, chlorine, bromine or iodine atoms, or hydroxy or $C_{1-6}$ alkoxy, e.g. methoxy, ethoxy or isopropoxy, groups.

When the groups R⁶ and R⁷ or R⁷ and R⁸ are both alkyl groups these groups may be joined, together with the N atom to which they are attached, to form a heterocyclic ring. Such heterocyclic rings may be optionally interrupted by a further heteroatom or heteroatom-containing group selected from —O—, —S—, —N(R⁷)—, —C(O)— or —C(S)— groups. Particular examples of such heterocyclic rings include piperidinyl, pyrazolidinyl, morpholinyl, thiomorpholinyl, pyrrolidinyl, imidazolidinyl and piperazinyl rings.

When R⁵ is an optionally substituted aromatic or heteroaromatic group it may be any such group as described hereinafter in relation to Cy¹.

In general, optionally substituted aromatic groups represented by the group Cy¹ include for example monocyclic or bicyclic fused ring $C_{6-12}$ aromatic groups, such as phenyl, 1- or 2-naphthyl, 1- or 2-tetrahydronaphthyl, indanyl or indenyl groups, especially phenyl.

Heteroaromatic groups represented by the group Cy¹ include for example $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—$C_{1-6}$ alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,5-oxadiazolyl, 1,3,4-oxadiazolyl, 1,3,4-thiadiazolyl, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, [2,3-dihydro]benzothienyl, benzotriazolyl, indolyl, indolinyl, indazolinyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, imidazo[1,5-a]pyridinyl, imidazo[1,5-a]pyrazinyl, imidazo[1,5-c]pyrimidinyl, pyrido[3,4-b]pyridyl, pyrido[3,2-b]pyridyl, pyrido[4,3-b]pyridyl, quinolinyl, isoquinolinyl, phthalazinyl, tetrazolyl, 5,6,7,8-tetrahydroquinolinyl, 5,6,7,8-tetrahydroisoquinolinyl, imidyl, e.g. succinimidyl, phthalimidyl or naphthalimidyl such as 1,8-naphthalimidyl, pyrazolo[4,3-d]pyrimidinyl, furo[3,2-c]pyrimidinyl, thieno[3,2-d]pyrimidinyl, pyrrolo[3,2-d]pyrimidinyl, pyrazolo[3,2-b]pyridinyl, furo[3,2-b]pyridinyl, thieno[3,2-b]pyridinyl, pyrrolo[3,2-b]pyridinyl, thiazolo[3,2-a]pyridinyl, pyrido[1,2-a]pyrimidinyl, tetrahydroimidazo[1,2-a]pyrimidinyl and dihydroimidazo[1,2-a]pyrimidinyl groups.

Optional substituents which may be present on aromatic or heteroaromatic groups represented by the group $Cy^1$ include one, two, three or more substituents, each selected from an atom or group $R^{10}$ in which $R^{10}$ is $R^{10a}$ or -$L^6Alk^5(R^{10a})_r$, where $R^{10a}$ is a halogen atom, or an amino (—$NH_2$), substituted amino, nitro, cyano, hydroxyl (—OH), substituted hydroxyl, formyl, carboxyl (—$CO_2H$), esterified carboxyl, thiol (—SH), substituted thiol, —$COR^{11}$ [where $R^{11}$ is an -$L^6Alk^3(R^{10a})_r$, aryl or heteroaryl group], —$CSR^{11}$, —$SO_3H$, —$SOR^{11}$, —$SO_2R^{11}$, —$SO_3R^{11}$, —$SO_2NH_2$, —$SO_2NHR^{11}$, —$SO_2N(R^{11})_2$, —$CONH_2$, —$CSNH_2$, —$CONHR^{11}$, —$CSNHR^{11}$, —$CON(R^{11})_2$, —$CSN(R^{11})_2$, —$N(R^{12})SO_2R^{11}$ [where $R^{12}$ is a hydrogen atom or a straight or branched alkyl group], —$N(SO_2R^{11})_2$, —$N(R^{12})SO_2NH_2$, —$N(R^{12})SO_2NHR^{11}$, —$N(R^{12})SO_2N(R^{11})_2$, —$N(R^{12})COR^{11}$, —$N(R^{12})CONH_2$, —$N(R^{12})CONHR^{11}$, —$N(R^{12})CON(R^{11})_2$, —$N(R^{12})CSNH_2$, —$N(R^{12})CSNHR^{11}$, —$N(R^{12})CSN(R^{11})_2$, —$N(R^{12})CSR^{11}$, —$N(R^{12})C(O)OR^{11}$, —C=$NR^{12}(NR^{12})$, —$SO_2NHet^1$ [where —$NHet^1$ is an optionally substituted $C_{3-7}$ cyclicamino group optionally containing one or more other —O— or —S— atoms or —$N(R^{12})$, —C(O)— or —C(S)— groups], —$CONHet^1$, —$CSNHet^1$, —$N(R^{12})SO_2NHet^1$, —$N(R^{12})CONHet^1$, —$N(R^{12})CSNHet^1$, —$SO_2N(R^{12})Het$ [where -Het is an optionally substituted monocyclic $C_{3-7}$ carbocyclic group optionally containing one or more other —O— or —S— atoms or —$N(R^{12})$—, —C(O)—, —S(O)— or —$S(O)_2$— groups], -Het, —$CON(R^{12})Het$, —$CSN(R^{12})Het$, —$N(R^{12})CON(R^{12})Het$, —$N(R^{12})CSN(R^{12})Het$, —$N(R^{12})SO_2N(R^{12})Het$, aryl or heteroaryl groups; $L^6$ is a covalent bond or a linker atom or group; $Alk^5$ is an optionally substituted straight or branched $C_{1-6}$ alkylene, $C_{2-6}$ alkenylene or $C_{2-6}$ alkynylene chain, optionally interrupted by one, two or three —O— or —S— atoms or —$S(O)_k$— [where k is an integer 1 or 2] or —$N(R^{12})$—, e.g. —$N(CH_3)$—, groups; and r is zero or the integer 1, 2, or 3. It will be appreciated that when two $R^{11}$ or $R^{12}$ groups are present in one of the above substituents the $R^{11}$ and $R^{12}$ groups may be the same or different.

When $L^6$ in the group -$L^6Alk^5(R^{10a})_r$ is a linker atom or group it may be for example any divalent linking atom or group. Particular examples include —O— or —S— atoms or —C(O)—, —C(O)O—, —OC(O)—, —C(S)—, —S(O)—, —$S(O)_2$—, —$N(R^3)$— [where $R^3$ is a hydrogen atom or a straight or branched alkyl group], —$N(R^3)O$—, —$N(R^3)N$—, —$CON(R^3)$—, —$OC(O)N(R^3)$—, —$CSN(R^3)$—, —$N(R^3)CO$—, —$N(R^3)C(O)O$—, —$N(R^3)CS$—, —$S(O)_2N(R^3)$—, —$N(R^3)S(O)_2$—, —$N(R^3)CON(R^3)$—, —$N(R^3)CSN(R^3)$— or —$N(R^3)SO_2N(R^3)$— groups. Where $L^6$ contains two $R^3$ groups these may be the same or different.

When in the group -$L^6Alk^5(R^{10a})_r$ is an integer 1, 2 or 3, it is to be understood that the substituent or substituents $R^{10a}$ may be present on any suitable carbon atom in -$Alk^5$. Where more than one $R^{10a}$ substituent is present these may be the same or different and may be present on the same or different atom in -$Alk^5$. Clearly, when r is zero and no substituent $R^{10a}$ is present the alkylene, alkenylene or alkynylene chain represented by $Alk^5$ becomes an alkyl, alkenyl or alkynyl group.

When $R^{10a}$ is a substituted amino group it may be for example a group —$NHR^{11}$ [where $R^{11}$ is as defined above] or a group —$N(R^{11})_2$ wherein each $R^{11}$ group is the same or different.

When $R^{10a}$ is a halogen atom it may be for example a fluorine, chlorine, bromine, or iodine atom.

When $R^{10a}$ is a substituted hydroxyl or substituted thiol group it may be for example a group —$OR^{11}$ or —$SR^{12}$ respectively.

Esterified carboxyl groups represented by the group $R^{10a}$ include groups of formula —$CO_2Alk^6$ wherein $Alk^6$ is a straight or branched, optionally substituted $C_{1-8}$ alkyl group such as a methyl, ethyl, n-propyl, isopropyl, n-butyl, isobutyl, sec-butyl or tert-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^6$ group include $R^{10a}$ atoms and groups as described above.

When $Alk^5$ is present in or as a substituent it may be for example a —$CH_2$—, —$CH(CH_3)$—, —$C(CH_3)_2$—, —$CH_2CH_2$—, —$CH_2CH_2CH_2$—, —$CH(CH_3)CH_2$—, —$CH_2CH_2CH_2CH_2$—, —$CH_2CH(CH_3)CH_2$—, —CH($CH_3$)$CH_2CH_2$—, —$C(CH_3)_2CH_2$—, —CH=CH—, —CH=CHCH$_2$—, —$CH_2$CH=CH—, —CH=CHCH$_2$CH$_2$—, —$CH_2$CH=CHCH$_2$—, —$CH_2$CH$_2$CH=CH—, —C≡C—, —C≡CCH$_2$—, —$CH_2$C≡C—, —C≡CCH$_2$CH$_2$—, —$CH_2$C≡CCH$_2$— or —$CH_2$CH$_2$C≡C— chain, optionally interrupted by one, two, or three —O— or —S— atoms or —S(O)—, —$S(O)_2$— or —$N(R^{12})$—, e.g. —$N(CH_3)$—, groups. The aliphatic chains represented by $Alk^5$ may be optionally substituted by one, two or three halogen atoms in addition to any $R^{10a}$ groups that may be present.

Aryl or heteroaryl groups represented by the groups $R^{10a}$ or $R^{11}$ include mono- or bicyclic optionally substituted $C_{6-12}$ aromatic or $C_{1-9}$ heteroaromatic groups as described above for the group $Cy^1$. The aromatic and heteroaromatic groups may be attached to the group $Cy^1$ in compounds of formula (1) by any carbon atom or heteroatom, e.g. nitrogen atom, as appropriate.

It will be appreciated that when —$NHet^1$ or -Het forms part of a substituent $R^{10}$ the heteroatoms or heteroatom-containing groups that may be present within the ring —$NHet^1$ or -Het take the place of carbon atoms within the parent carbocyclic ring.

Thus when —$NHet^1$ or -Het forms part of a substituent $R^{10}$ each may be for example an optionally substituted pyrrolidinyl, imidazolidinyl, pyrazolidinyl, piperazinyl, morpholinyl, thiomorpholinyl, piperidinyl or thiazolidinyl group. Additionally Het may represent, for example, an optionally substituted cyclopentyl or cyclohexyl group. Optional substituents which may be present on —NHet$^1$ include those substituents described above when Cy$^1$ is a heterocycloaliphatic group.

Particularly useful atoms or groups represented by R$^{10}$ include fluorine, chlorine, bromine or iodine atoms, or $C_{1-6}$ alkyl, e.g. methyl, ethyl, n-propyl, isopropyl, n-butyl or tert-butyl, optionally substituted phenyl, pyridyl, pyrimidinyl, pyrrolyl, furyl, thiazolyl, or thienyl, $C_{1-6}$ hydroxyalkyl, e.g. hydroxymethyl or hydroxyethyl, carboxy$C_{1-6}$alkyl, e.g. carboxyethyl, $C_{1-6}$ alkylthio, e.g. methylthio or ethylthio, carboxy$C_{1-6}$alkylthio, e.g. carboxymethylthio, 2-carboxyethylthio or 3-carboxy-propylthio, $C_{1-6}$ alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{3-7}$ cycloalkyl, e.g. cyclobutyl or cyclopentyl, $C_{5-7}$ cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$ alkylamino, e.g. methylamino or ethylamino, —CH(CH$_3$)NH$_2$ or —C(CH$_3$)$_2$NH$_2$, halo$C_{1-6}$alkylamino, e.g. fluoro$C_{1-6}$ alkylamino, —CH(CF$_3$)NH$_2$ or —C(CF$_3$)$_2$NH$_2$, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkyl-amino$C_{1-6}$alkoxy, e.g. dimethylaminoethoxy, diethylaminoethoxy, diisopropylaminoethoxy or dimethylaminopropoxy, imido, such as phthalimido or naphthalimido, e.g. 1,8-naphthalimido, nitro, cyano, hydroxyl (—OH), formyl [HC(O)—], carboxyl (—CO$_2$H), —CO$_2$Alk$^6$ [where Alk$^6$ is as defined above], $C_{1-6}$ alkanoyl, e.g. acetyl, optionally substituted benzoyl, thiol (—SH), thio$C_{1-6}$alkyl, e.g. thiomethyl or thioethyl, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)NH$_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino, e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or tert-butoxycarbonylamino, or optionally substituted benzyloxy, pyridylmethoxy, thiazolylmethoxy, benzyloxycarbonylamino, benzyloxycarbonylamino$C_{1-6}$alkyl, e.g. benzyloxycarbonylaminoethyl, benzothio, pyridylmethylthio or thiazolylmethylthio groups.

A further particularly useful group of substituents represented by R$^{10}$ when present on aromatic or heteroaromatic groups includes substituents of formula -L$^6$Alk$^5$R$^{10a}$ where L$^6$ is preferably a covalent bond or an —O— or —S— atom or —N(R$^3$)—, —C(O)—, —C(O)O—, —O—C(O)—, —N(R$^3$)CO—, —CON(R$^3$)— or —N(R$^3$)S(O)$_2$— group, Alk$^5$ is an optionally substituted $C_{1-6}$alkyl group optionally interrupted by one or two —O— or —S— atoms or —N(R$^{12}$)—, —C(O)—, —C(S)—, —CON(R$^{12}$— or —N(R$^{12}$)CO— groups, and R$^{10a}$ is an optionally substituted Het group as herein defined or an optionally substituted heteroaromatic group as hereinbefore described in relation to Cy$^1$.

Where desired, two R$^{10}$ substituents may be linked together to form a cyclic group such as a cyclic ether, e.g. a $C_{1-6}$ alkylenedioxy group such as methylenedioxy or ethylenedioxy.

It will be appreciated that where two or more R$^{10}$ substituents are present, these need not necessarily be the same atoms and/or groups. In general, the substituent(s) may be present at any available ring position on the aromatic or heteroaromatic group represented by the group Cy$^1$.

The substituted aromatic or heteroaromatic group represented by Ar in compounds of the invention may be any aromatic or heteroaromatic group as hereinbefore described for Cy$^1$. Optional substituents which may be present include those R$^{10}$ atoms and groups as generally or particularly described in relation to Cy$^1$ aromatic and heteroaromatic groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulfonates, e.g. methanesulfonates, ethanesulfonates, or isothionates, arylsulfonates, e.g. p-toluenesulfonates, besylates or napsylates, phosphates, sulphates, hydrogensulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In one embodiment, Y is —C(O)—. In another embodiment, Y is —S(O)$_2$—.

In one class of compounds of formula (1) n is the integer 1. When in compounds of formula (1) n is the integer 1, Alk$^1$ is preferably a —CH$_2$CH$_2$— chain or more especially is —CH$_2$—.

In one class of compounds of formula (1) n is zero.

Particularly preferred $Cy^1$ optionally substituted cycloaliphatic groups include optionally substituted $C_{3-7}$ cycloalkyl groups, especially cyclopropyl, cyclobutyl, cyclopentyl or cyclohexyl groups. $Cy^1$ is in particular a cyclopropyl group.

Each of these preferred $Cy^1$ cycloalkyl groups may be unsubstituted. When substituents are present these may in particular include halogen atoms, especially fluorine, chlorine or bromine atoms, or $C_{1-6}$ alkyl groups, especially $C_{1-3}$ alkyl groups, most especially a methyl group, or halo$C_{1-6}$ alkyl groups, especially fluoro$C_{1-6}$alkyl groups, most especially a —$CF_3$ group, or $C_{1-6}$ alkoxy groups, especially a methoxy, ethoxy, propoxy or isopropoxy group, or halo$C_{1-6}$alkoxy groups, especially fluoro$C_{1-6}$alkoxy groups, most especially a —$OCF_3$ group, or a cyano (—CN), esterified carboxyl, especially —$CO_2CH_3$ or —$CO_2C(CH_3)_3$, nitro (—$NO_2$), amino (—$NH_2$), substituted amino, especially —$NHCH_3$ or —$N(CH_3)_2$, —$C(O)R^6$, especially —$C(O)CH_3$, or —$N(R^6)C(O)R^7$, especially —$NHCOCH_3$, group.

Particularly preferred $Cy^1$ aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl and triazinyl groups. In a further preference, the heteroaromatic group may be an eight- to thirteen-membered bicyclic fused ring containing one or two oxygen, sulphur or nitrogen atoms. Particularly useful groups of this type include optionally substituted indolyl groups.

Particularly preferred optional substituents which may be present on $Cy^1$ aromatic or heteroaromatic groups include one, two or three atoms or groups —$R^{10a}$ or -$L^6Alk^5(R^{10a})_r$ as hereinbefore defined. Particularly useful optional substituents include halogen atoms, especially fluorine, chlorine or bromine atoms, or $C_{1-6}$ alkyl groups, especially $C_{1-3}$ alkyl groups, most especially a methyl group, or halo$C_{1-6}$alkyl groups, especially fluoro$C_{1-6}$alkyl groups, most especially a —$CF_3$ group, or $C_{1-6}$alkoxy groups, especially a methoxy, ethoxy, propoxy or isopropoxy group, or halo$C_{1-6}$alkoxy groups, especially fluoro$C_{1-6}$alkoxy groups, most especially a —$OCF_3$ group, or a cyano (—CN), carboxyl (—$CO_2H$), esterified carboxyl (—$CO_2Alk^6$), especially —$CO_2CH_3$, —$CO_2CH_2CH_3$, or —$CO_2C(CH_3)_3$, nitro (—$NO_2$), amino (—$NH_2$), substituted amino, especially —$NHCH_3$ or —$N(CH_3)_2$, —$COR^{11}$, especially —$COCH_3$, or —$N(R^{12})COR^{11}$, especially —$NHCOCH_3$, group.

Further preferred optional substituents which may be present on $Cy^1$ aromatic or heteroaromatic groups include groups of formula -$L^6Alk^5(R^{10a})_r$ in which r is the integer 1 or 2, $L^6$ is a covalent bond or an —O— or —S— atom or a —$N(R^3)$—, especially —NH— or —$N(CH_3)$—, —C(O)—, —C(S)—, —C(O)O—, —OC(O)—, —$N(R^3)CO$—, especially —NHCO—, or —$CON(R^3)$—, especially —CONH—, group, $Alk^5$ is a $C_{1-6}$alkylene chain, especially a —$CH_2$—, —$CH_2CH_2$—, —$CH_2CH_2CH_2$— or —$CH_2CH_2CH_2CH_2$— chain, and $R^{10a}$ is a hydroxyl or substituted hydroxyl group, especially a —$OCH_3$, —$OCH_2CH_3$ or —$OCH(CH_3)_2$ group, or a —$NH_2$ or substituted amino group, especially a —$N(CH_3)_2$ or —$N(CH_2CH_3)_2$ group, or a -Het group, especially an optionally substituted monocyclic $C_{5-7}$ carbocyclic group containing one, two or three —O—, —S—, —$N(R^{12})$—, especially —NH— or —$N(CH_3)$—, or —C(O)— groups within the ring structure as previously described, most especially an optionally substituted pyrrolidinyl, imidazolidinyl, piperidinyl, e.g. N-methylpiperidinyl, morpholinyl, thiomorpholinyl or piperazinyl group, or $R^{10a}$ is an optionally substituted heteroaromatic group, especially a five- or six-membered monocyclic heteroaromatic group containing one, two, three or four heteroatoms selected from oxygen, sulphur or nitrogen atoms, such as optionally substituted pyrrolyl, furyl, thienyl, imidazolyl, triazolyl, pyridyl, pyrimidinyl, triazinyl, pyridazinyl, or pyrazinyl group. Particularly preferred optional substituents on the -Het groups just described include hydroxyl (—OH) and carboxyl (—$CO_2H$) groups or those preferred optional substituents just described in relation to the group $Cy^1$, especially when $Cy^1$ is a cycloalkyl group.

In one particularly preferred group of compounds of formula (1) $Cy^1$ is an optionally substituted phenyl group, especially a phenyl group optionally substituted by one, two or three substituents where at least one, and preferably two, substituents are located ortho to the bond joining $Cy^1$ to the remainder of the compound of formula (1). Particularly preferred ortho substituents include halogen atoms, especially fluorine or chlorine atoms, or $C_{1-3}$ alkyl groups, especially methyl, $C_{1-3}$ alkoxy groups, especially methoxy, halo$C_{1-3}$ alkyl groups, especially —$CF_3$, halo$C_{1-3}$alkoxy groups, especially —$OCF_3$, or cyano (—CN), groups. In this class of compounds a second or third optional substituent when present in a position other than the ortho positions of the ring $Cy^1$ may be preferably an atom or group —$R^{10a}$ or -$L^6Alk^5(R^{10a})_r$ as herein generally and particularly described. In another preference, the $Cy^1$ phenyl group may have a substituent para to the bond joining $Cy^1$ to the remainder of the compound of formula (1). Particular para substituents include those particularly preferred ortho substituents just described. Where desired, the pare substituent may be present with other ortho or meta substituents as just mentioned.

Examples of specific substituents on $Cy^1$ include halogen (especially fluoro or chloro) and $C_{1-4}$ alkyl (especially methyl).

Specific $Cy^1$ groups include phenyl, fluorophenyl, chlorophenyl, methylphenyl and cyclopropyl.

Particularly preferred Ar aromatic groups in compounds of formula (1) include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl and triazinyl groups.

Particularly preferred optional substituents which may be present on Ar aromatic or heteroaromatic groups include atoms or groups —$R^{10a}$ or -$L^6Alk^5(R^{10a})_r$ as hereinbefore defined. Particularly useful optional substituents include halogen atoms, especially fluorine, chlorine or bromine atoms, or $C_{1-6}$ alkyl groups, especially $C_{1-3}$ alkyl groups, most especially a methyl group, or halo$C_{1-6}$alkyl groups, especially fluoro$C_{1-6}$alkyl groups, most especially a —$CF_3$ group, or $C_{1-6}$ alkoxy groups, especially a methoxy, ethoxy, propoxy or isopropoxy group, or halo$C_{1-6}$alkoxy groups, especially fluoro$C_{1-6}$alkoxy groups, most especially a —$OCF_3$ group, or a cyano (—CN), esterified carboxyl, especially —$CO_2CH_3$ or —$CO_2C(CH_3)_3$, nitro (—$NO_2$), amino (—$NH_2$), substituted amino, especially —$NHCH_3$ or —$N(CH_3)_2$, —$COR^{11}$, especially —$COCH_3$, or —$N(R^{12})COR^{11}$, especially —$NHCOCH_3$, group.

Particularly useful Ar groups in compounds of formula (1) include phenyl and mono- or disubstituted phenyl groups in which each substituent is in particular a —$R^{10a}$ or -$L^6Alk^5$($R^{10a}$)$_r$ atom or group as just defined and is especially a halogen atom or a $C_{1-3}$ alkyl, $C_{1-3}$ alkoxy or —CN group.

Examples of specific substituents on Ar include halogen (especially fluoro or chloro), cyano and $C_{1-4}$ alkyl (especially methyl).

Specific Ar groups include phenyl, difluorophenyl, (chloro)(fluoro)phenyl, (fluoro)(methyl)phenyl, chlorophenyl, cyanophenyl and methylphenyl.

Particular examples of $Alk^2$ when present in compounds of the invention include —$CH_2$—, —$CH_2CH_2$—, —$C(CH_3)_2$— and —$CH(CH_3)CH_2$—. In one embodiment, $Alk^2$ is —$CH_2$—. In another embodiment, $Alk^2$ is —$C(CH_3)_2$—.

Suitably, $R^1$ is methyl.

Suitably, $R^2$ is hydrogen or methyl. Suitably, $R^3$ is hydrogen or methyl. In one embodiment, $R^2$ and $R^3$ are both hydrogen. In another embodiment, $R^2$ and $R^3$ are both methyl.

In compounds of the invention, m may be selected to vary the ring size from a ring having, in addition to the nitrogen atom, a minimum of 3 carbon atoms up to 6 carbon atoms. Particularly advantageous rings are those wherein m is the integer 1 or 2.

In a preferred embodiment, m is the integer 2. In another embodiment, m is the integer 1. In a further embodiment, m is the integer 3.

In a particular embodiment, p is the integer 1. In another embodiment, p is the integer 2.

Each substituent $R^d$ may be present on any ring carbon atom. In one particular class of compounds of the invention one or two $R^d$ substituents are present.

Suitable values of $R^d$ include —OH, -($Alk^2$)OH, -($Alk^2$)$OR^1$, —$NR^2R^3$ and -($Alk^2$)$NR^2R^3$.

Detailed values of $R^d$ include —OH, —$CH_2$OH, —$C(CH_3)_2$OH, —$CH_2OCH_3$, —$NH_2$, —$N(CH_3)_2$ and —$CH_2NH_2$.

Representative values of $R^d$ include —OH, -($Alk^2$)OH and -($Alk^2$)$OR^1$.

Illustrative values of $R^d$ include —OH, —$CH_2$OH, —$C(CH_3)_2$OH and —$CH_2OCH_3$.

Particular $R^d$ substituents include —OH, —$CH_2$OH, —$CH(CH_3)$OH and —$C(CH_3)_2$OH groups.

Particularly useful compounds of the invention include each of the compounds described in the Examples hereinafter, and the salts, solvates, hydrates and N-oxides thereof.

Compounds according to the invention are potent and selective inhibitors of p38 kinases, including all isoforms and splice variants thereof. More specifically the compounds of the invention are inhibitors of p38α, p38β and p38β2. The ability of the compounds to act in this way may be simply determined by employing tests such as those described in the Examples hereinafter.

The compounds of formula (1) are of use in modulating the activity of p38 kinases and in particular are of use in the prophylaxis and treatment of any p38 kinase mediated diseases or disorders in a human, or other mammal. The invention extends to such a use and to the use of the compounds for the manufacture of a medicament for treating such diseases or disorders. Further the invention extends to the administration to a human of an effective amount of a p38 inhibitor for treating any such disease or disorder.

The invention also extends to the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further the invention extends to the administration to a human of an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, inflammatory diseases, destructive bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation and conditions associated with prostaglandin endoperoxidase synthetase-2 (COX-2).

Autoimmune diseases which may be prevented or treated include but are not limited to rheumatoid arthritis, inflammatory bowel disease, ulcerative colitis, Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs host disease and psoriasis.

The invention further extends to the particular autoimmune disease rheumatoid arthritis.

Inflammatory diseases which may be prevented or treated include but are not limited to asthma, allergies, respiratory distress syndrome and acute or chronic pancreatitis.

Destructive bone disorders which may be prevented or treated include but are not limited to osteoporosis, osteoarthritis and multiple myeloma-related bone disorder.

Proliferative diseases which may be prevented or treated include but are not limited to acute or chronic myelogenous leukemia, Kaposi's sarcoma, metastatic melanoma and multiple myeloma.

Neurodegenerative diseases which may be prevented or treated include but are not limited to Parkinson's disease, Alzheimer's disease, cerebral ischemias and neurodegenerative disease caused by traumatic injury.

Viral diseases which may be prevented or treated include but are not limited to acute hepatitis infection (including hepatitis A, hepatitis B and hepatitis C), HIV infection and CMV retinitis.

Infectious diseases which may be prevented or treated include but are not limited to septic shock, sepsis and Shigellosis.

In addition, p38 inhibitors of this invention also exhibit inhibition of expression of inducible pro-inflammatory proteins such as prostaglandin endoperoxidase synthetase-2, otherwise known as cyclooxygenase-2 (COX-2), and are therefore of use in therapy. Pro-inflammatory mediators of the cyclooxygenase pathway derived from arachidonic acid are produced by inducible COX-2 enzyme. Regulation of COX-2 would regulate these pro-inflammatory mediators such as prostaglandins, which affect a wide variety of cells and are important and critical inflammatory mediators of a wide variety of disease states and conditions. In particular these inflammatory mediators have been implicated in pain, such as in the sensitization of pain receptors, or edema. Accordingly additional p38 mediated conditions which may be prevented or treated include edema, analgesia, fever and pain such as neuromuscular pain, headache, dental pain, arthritis pain and pain caused by cancer.

As a result of their p38 inhibitory activity, compounds of the invention have utility in the prevention and treatment of diseases associated with cytokine production including but not limited to those diseases associated with TNF, IL-1, IL-6 and IL-8 production.

Thus, TNF mediated diseases or conditions include for example rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoidosis, bone resorption disease, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis, pyresis, viral infections such as HIV, CMV, influenza and herpes; and veterinary viral infections, such as lentivirus infections, including but not limited to equine infectious anemia virus, caprine arthritis virus, visna virus or maedi virus; or retrovirus infections, including feline immunodeficiency virus, bovine immunodeficiency virus and canine immunodeficiency virus.

Compounds of the invention may also be used in the treatment of viral infections, where such viruses elicit TNF production in vivo or are sensitive to upregulation by TNF. Such viruses include those that produce TNF as a result of infection and those that are sensitive to inhibition, for instance as a result of decreased replication, directly or indirectly by the TNF inhibiting compounds of the invention. Such viruses include, but are not limited to, HIV-1, HIV-2 and HIV-3, Cytomegalovirus (CMV), Influenza, adenovirus and the Herpes group of viruses such as Herpes Zoster and Herpes Simplex.

IL-1 mediated diseases or conditions include for example rheumatoid arthritis, osteoarthritis, psoriatic arthritis, traumatic arthritis, rubella arthritis, inflammatory bowel disease, stroke, endotoxemia and/or toxic shock syndrome, inflammatory reaction induced by endotoxin, diabetes, pancreatic β-cell disease, Alzheimer's disease, tuberculosis, atherosclerosis, muscle degeneration and cachexia.

IL-8 mediated diseases and conditions include for example those characterized by massive neutrophil infiltration such as psoriasis, inflammatory bowel disease, asthma, cardiac, brain and renal reperfusion injury, adult respiratory distress syndrome, thrombosis and glomerulonephritis. The increased IL-8 production associated with each of these diseases is responsible for the chemotaxis of neutrophils into inflammatory sites. This is due to the unique property of IL-8 (in comparison to TNF, IL-1 and IL-6) of promoting neutrophil chemotaxis and activation. Therefore, inhibition of IL-8 production would lead to a direct reduction in neutrophil infiltration.

It is also known that both IL-6 and IL-8 are produced during rhinovirus (HRV) infections and contribute to the pathogenesis of the common cold and exacerbation of asthma associated with HRV infection [Turner et al., Clin. Infec. Dis., 1997, 26, 840; Grunberg et al., Am. J. Crit. Care Med., 1997, 155, 1362; Zhu et al., J. Clin. Invest., 1996, 97, 421]. It has also been demonstrated in vitro that infection of pulmonary epithelial cells (which represent the primary site of infection by HRV) with HRV results in production of IL-6 and IL-8 [Sabauste et al., J. Clin. Invest., 1995, 96, 549]. Therefore, p38 inhibitors of the invention may be used for the treatment or prophylaxis of the common cold or respiratory viral infection caused by human rhinovirus infection (HRV), other enteroviruses, coronavirus, influenza virus, parainfluenza virus, respiratory syncytial virus or adenovirus infection.

For the prophylaxis or treatment of a p38 or pro-inflammatory cytokine mediated disease the compounds according to the invention may be administered to a human or mammal as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long-acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds for use according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively the compounds for use according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds for use according to the present invention may be conveniently formulated as microionized suspensions in isotonic, pH adjusted sterile saline, either with or without a preservative such as a bactericidal or fungicidal agent, for example phenylmercuric nitrate, benzylalkonium chloride or chlorhexidine acetate. Alternatively for ophthalmic administration compounds may be formulated in an ointment such as petrolatum.

For rectal administration the compounds for use according to the present invention may be conveniently formulated as suppositories. These can be prepared by mixing the active component with a suitable non-irritating excipient which is solid at room temperature but liquid at rectal temperature and so will melt in the rectum to release the active component. Such materials include for example cocoa butter, beeswax and polyethylene glycols.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg, e.g. around 0.01 mg/kg to 40 mg/kg body weight, for oral or buccal administration, from around 10 ng/kg to 50 mg/kg body weight for parenteral administration, and around 0.05 mg to around 1000 mg, e.g. around 0.5 mg to around 1000 mg, for nasal administration or administration by inhalation or insufflation.

The compounds of the invention may be prepared by a number of processes as generally described below and more specifically in the Examples hereinafter. In the following process description, the symbols Ar, $Cy^1$, $Alk^1$, n, $R^d$, p, m and Y when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Greene, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups.

Thus, according to a further aspect of the invention a compound of formula (1) in which Y is a —C(O)— group may be prepared from a carboxylic acid of formula (2) or ester of formula (5) according to amide bond forming reactions well known to those skilled in the art. Such reactions are set forth in references such as March's *Advanced Organic Chemistry* (John Wiley and Sons 1992), Larock's *Comprehensive Organic Transformations* (VCH Publishers Inc., 1992) and *Comprehensive Organic Functional Group Transformations*, ed. Katritzky et al., volumes 1-8, 1984, and volumes 1-11, 1994 (Pergamon). Examples of such methods that may be employed to give compounds of formula (1a) are set out, but not limited to the reactions, in Scheme 1 and Scheme 2 below.

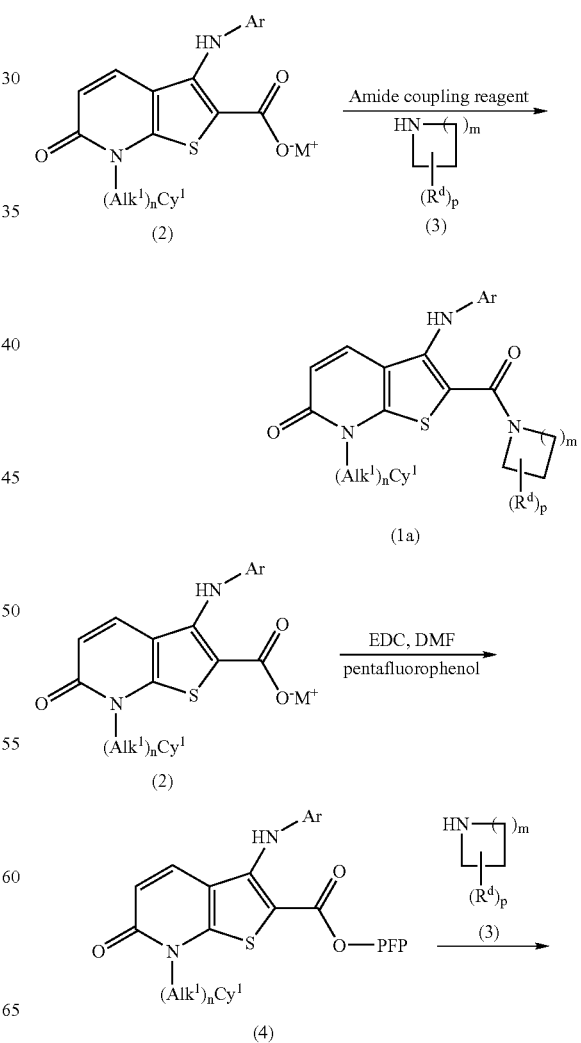

Scheme 1

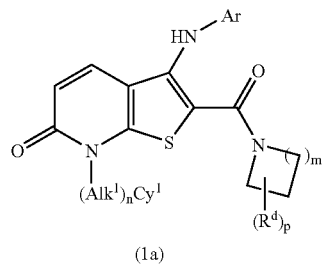

(1a)

Thus, amides of formula (1a) may be formed by reaction of a carboxylate salt of formula (2) [where M⁺ is metal counterion such as a sodium or lithium ion or is alternatively an ammonium or trialkylammonium counterion] with an amine of formula (3) in the presence of a coupling reagent such as a carbodiimide, e.g. 1-(3-dimethylaminopropyl)-3-ethylcarbodiimide (EDC) or N,N'-dicyclohexylcarbodiimide, optionally in the presence of a base such as an amine, e.g. triethylamine or N-methylmorpholine. These reactions may be performed in a solvent such as an amide solvent, e.g. N,N-dimethyl-formamide (DMF), or an ether, e.g. a cyclic ether such as tetrahydrofuran or 1,4-dioxane, or a halogenated solvent such as dichloromethane, at around ambient temperature to 60° C. In another procedure a pentafluorophenyl ester of formula (4) may be prepared by reaction of a carboxylic acid of formula (2) with pentafluorophenol in the presence of a coupling reagent such as 1-(3-dimethylaminopropyl)-3-ethylcarbodiimide in a solvent such as an amide solvent, e.g. DMF, at around ambient temperature. Amides of formula (1a) can then be prepared by reaction of the pentafluorophenyl ester with amines of formula (3) in an organic solvent such as a halogenated hydrocarbon, e.g. dichloromethane, at around ambient temperature, optionally in the presence of a tertiary amine base such as triethylamine or diisopropylethylamine. The intermediate acids of formula (2) may be prepared by hydrolysis of esters of formula (5) using a base such as an alkali metal hydroxide, e.g. sodium hydroxide or lithium hydroxide, in water and a solvent such as tetrahydrofuran or an alcohol such as ethanol at a temperature from around ambient to reflux.

Amides of formula (1a) can also be prepared directly from esters of formula (5) by heating with an amine of formula (3) up to the reflux temperature of the amine optionally in the presence of a solvent such as 2-ethoxyethanol either at atmospheric pressure or under pressure in a sealed tube (Scheme 2).

Scheme 2

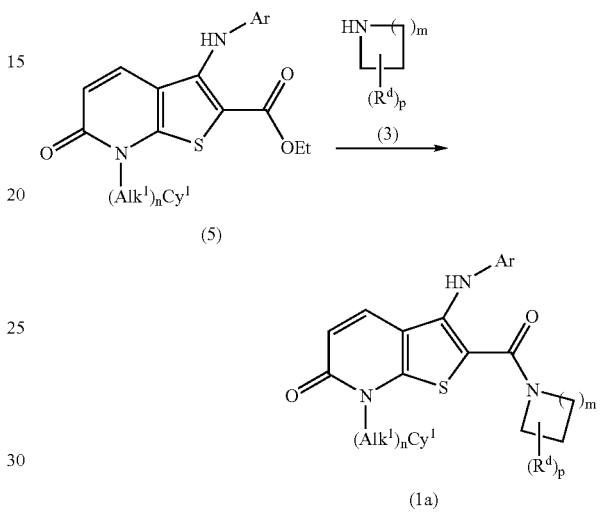

The intermediate esters of formula (5) may be prepared by the methods set out in Scheme 3 below. In the Scheme the preparation of an ethyl ester is specifically shown, but it will be appreciated that other esters may be obtained by simply varying the ester starting material and if appropriate any reaction conditions.

Scheme 3

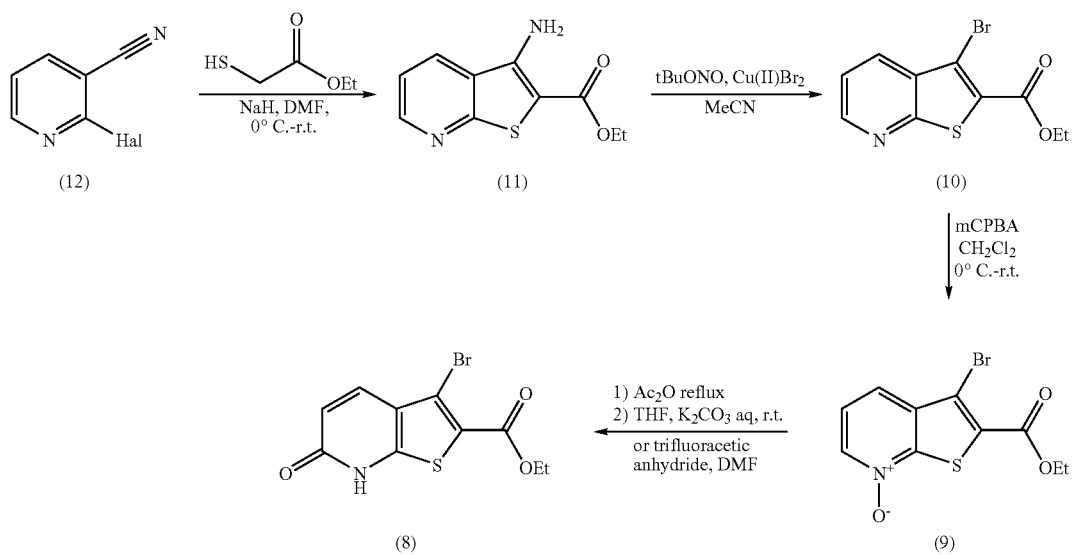

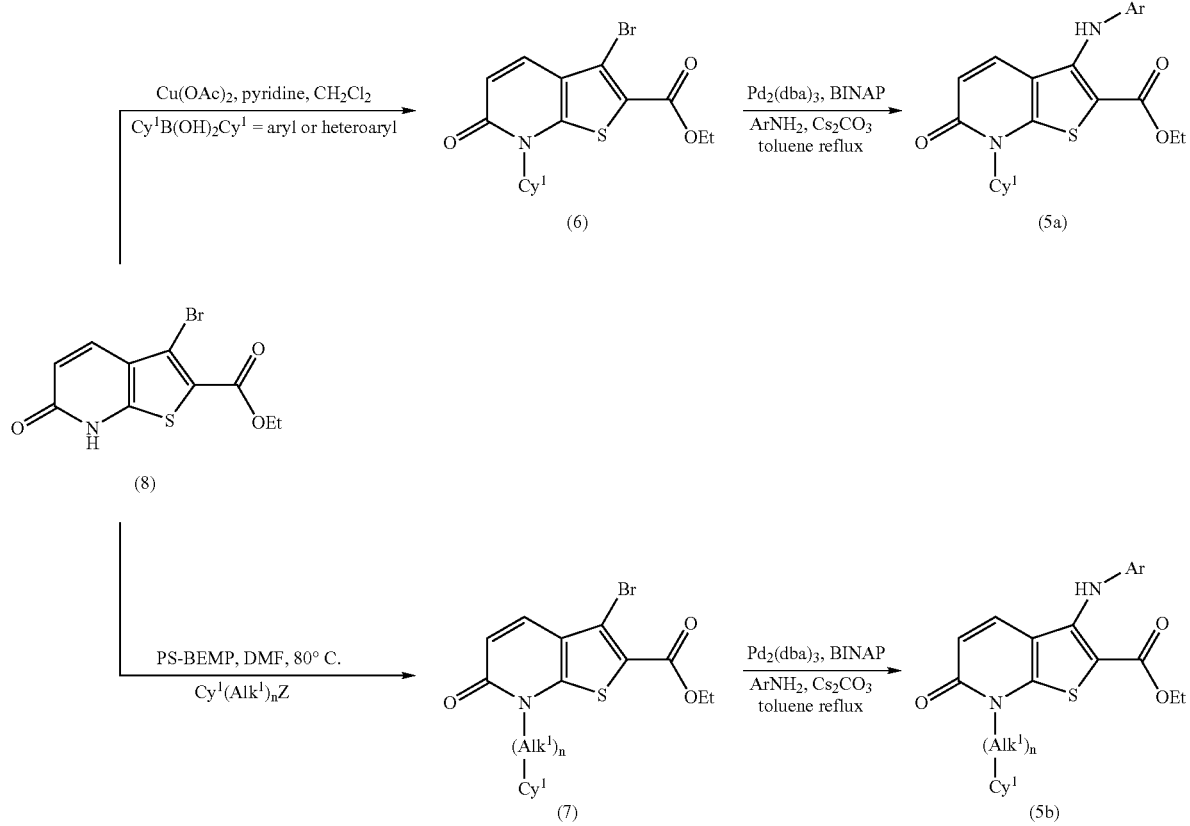

Thus, in Scheme 3 a compound of formula (5a) or (5b) may be prepared by reaction of a compound of formula (6) or (7) with an amine $ArNH_2$ in the presence of a palladium catalyst. The reaction may be conveniently carried out in a solvent such as toluene at an elevated temperature, e.g. the reflux temperature, using a catalyst such as tris(dibenzylideneacetone)-dipalladium(0), a phosphine ligand such as 2,2'-bis(diphenylphosphino)-1,1'-binaphthyl, and a base such as caesium carbonate. Where desired, alternative reaction conditions may be used, for example as described in the literature [Luker et al., *Tetrahedron Lett.*, 2001, 41, 7731; Buchwald, S. L., *J. Org. Chem.*, 2000, 65, 1144; Hartwig, J. F., *Angew. Chem. Int. Ed. Engl.*, 1998, 37, 2046].

Intermediates of formula (7) may be prepared by reaction of a compound of formula (8) with an alkylating agent of formula $Cy^1(Alk^1)_nZ$, where Z is a leaving group such as a halogen atom, e.g. a chlorine, bromine or iodine atom, or a sulphonyloxy group such as an alkylsulphonyloxy, e.g. trifluoromethylsulphonyloxy, or arylsulphonyloxy, e.g. phenylsulphonyloxy, group.

The reaction may be performed in the presence of a solvent, for example a substituted amide such as N,N-dimethylformamide, optionally in the presence of a base, for example an inorganic base such as sodium hydride, or an organic base such as an organic amine, e.g. a cyclic amine such as 1,5-diazabicyclo[4.3.0]non-5-ene, or a resin-bound organic amine such as resin-bound 2-tert-butylimino-2-diethylamino-1,3-dimethylperhydro-1,3,2-diaza-phosphorine (PS-BEMP), at an elevated temperature, for example 80 to 100° C.

Intermediates of formula (6) may be prepared by the reaction of a compound of formula (8) with a boronic acid of formula $Cy^1B(OH)_2$ in which $Cy^1$ is an aryl or heteroaryl group. The reaction may be performed in an organic solvent, for example a halogenated hydrocarbon such as dichloromethane or dichloroethane, in the presence of a copper reagent, for example a copper(I) salt such as CuI, or for example a copper(II) reagent such as copper(II) acetate, optionally in the presence of an oxidant, for example 2,2,6,6-tetramethylpiperidine-1-oxide or pyridine-N-oxide, optionally in the presence of a base, for example an organic amine such as an alkylamine, e.g. triethylamine, or an aromatic amine, e.g. pyridine, at a temperature from around ambient to the reflux temperature [see for example Chan, D. T. et al., *Tetrahedron Letters*, 1998, 2933; Lam, P. Y. S. et al., *Tetrahedron Letters*, 2001, 3415].

Intermediates of formula (6) where $Cy^1$ is an aryl or heteroaryl group may also be prepared by nucleophilic aromatic substitution of a suitably activated aryl or heteroaryl halide with a compound of formula (8). The reaction may be performed in a dialkylamide solvent such as DMF in the presence of a base such as a metal hydride, e.g. sodium hydride, at a temperature from around ambient to 100° C. Suitably activated aryl or heteroaryl halides are those with an electron-withdrawing substituent such as a nitro, cyano or ester group, e.g. a chloro- or fluoro-nitrobenzene or 2-chloro-5-nitropyridine. Alternatively a nitrogen-containing heteroaryl halide can be activated to nucleophilic substitution by N-oxidation, e.g. 2-chloropyridine N-oxide.

It will be appreciated that if desired the reactions just described may be carried out in the reverse order so that the amination using $ArNH_2$ is performed first with the intermediate of formula (8) followed by alkylation/arylation to yield the compound of formula (5). It may be necessary to protect the nitrogen function of compounds of formula (8) during the course of these reactions. Such protection may be achieved by O-alkylation with an alkyl halide, e.g. cyclopropylmethyl bromide, or an arylalkyl bromide, e.g. benzyl bromide, as shown in Scheme 4.

N,N-dimethylformamide from 0° C. to ambient temperature conditions [see for example Konno et al., *Heterocycles*, 1986, 24, 2169].

Pyridine N-oxides of formula (9) may be formed by oxidation of pyridines of formula (10) using an oxidising agent such as hydrogen peroxide in the presence of an acid such as

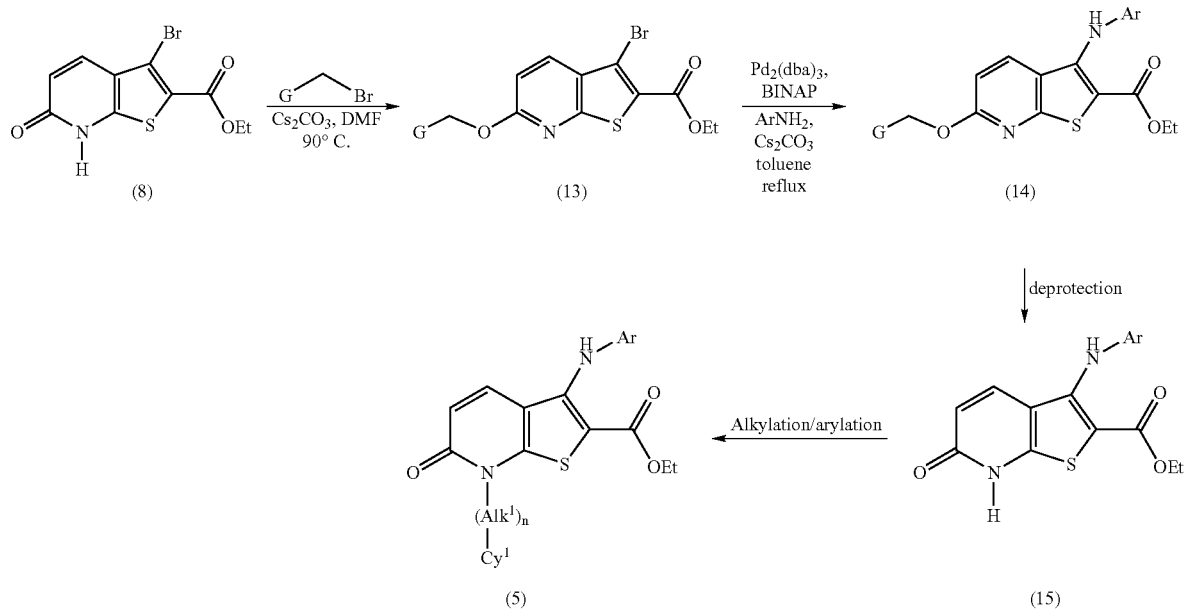

Where G = Aryl or alkyl group

The O-alkylation reaction may be performed in an organic solvent such as DMF in the presence of a base, for example an inorganic base such as $Cs_2CO_3$ or an organic base such as an amine, e.g. a cyclic amine such as 1,5-diazabicyclo[4.3.0]non-5-ene, at an elevated temperature, e.g. 80 to 100° C., to give a compound of formula (13). Reaction of the protected compound (13) with $ArNH_2$ under palladium catalysis can then be performed as previously described to give a compound of formula (14). Deprotection can then be achieved by treating a solution of this compound in an alcohol, e.g. MeOH, with a mineral acid such as concentrated HCl at an elevated temperature, e.g. the reflux temperature, to give a compound of formula (15). Alternatively when benzyl protection is employed then this group may be removed reductively by treating a solution of compound (14) in an organic solvent such as EtOH using a palladium or platinum catalyst, e.g. palladium on carbon or $PtO_2$, under an elevated pressure of hydrogen at a temperature from around ambient to 60° C. Compounds of formula (15) can then undergo alkylation/arylation reactions as previously described to give compounds of formula (5).

Intermediate pyridinones of formula (8) may be prepared from pyridine N-oxides of formula (9) by sequential reaction with an anhydride, for example acetic anhydride, at an elevated temperature, for example the reflux temperature, followed by reaction with an inorganic base, for example a carbonate such as aqueous potassium carbonate, in a solvent such as an ether, for example a cyclic ether, e.g. tetrahydrofuran, at around ambient temperature. Alternatively the reaction may be performed using trifluoroacetic anhydride in acetic acid, at an elevated temperature, for example around 70° C. to 80° C., or alternatively by reaction with a peracid such as peracetic acid or m-chloroperoxybenzoic acid in a solvent such as a halogenated hydrocarbon, e.g. dichloromethane, or an alcohol, e.g. tert-butanol, at a temperature from the ambient temperature to the reflux temperature.

Intermediate pyridines of formula (10) in Scheme 3 may be obtained by standard methods such as for example by the Sandmeyer reaction. Thus, for example, a bromide of formula (10) may be prepared by treatment of an aryl amine of formula (11) with an alkyl nitrite, for example tert-butyl nitrite, and a copper salt, for example copper(II) bromide, in the presence of a solvent, for example a nitrile such as acetonitrile, at a temperature from about 0° to around 65° C.

Amines of formula (11) may be formed from 2-halopyridine-3-carbonitriles of formula (12) by reaction with a reagent such as ethyl 2-mercaptoacetate. The reaction may be performed in the presence of a solvent such as a substituted amide, for example N,N-dimethylformamide, or an ether, e.g. a cyclic ether such as tetrahydrofuran, or an alcohol such as ethanol, in the presence of a base, for example an inorganic base such as sodium carbonate or a hydride, e.g. sodium hydride, or an organic base such as 1,5-diazabicyclo[4.3.0]non-5-ene or a trialkylamine such as triethylamine, at a temperature between about 0° C. and 100° C. The carbonitrile starting materials are readily available or may be obtained from known compounds using standard procedures.

In another process intermediate esters of formula (5a) may be prepared by the reactions set out in Scheme 5. In the Scheme below $R^{20}$ represents an ester or nitrile and LG represents a leaving group such as a halogen atom, e.g. chlorine or bromine, or a sulfonyloxy group such as an alkylsulfonyloxy group, e.g. trifluoromethylsulfonyloxy, or an arylsulfonyloxy group, e.g. p-toluenesulfonyloxy.

methodology. For example, they may be prepared in situ by reaction of an acetate, e.g. ethyl acetate, with a base such as sodium methoxide followed by addition of a formate, e.g. methyl formate.

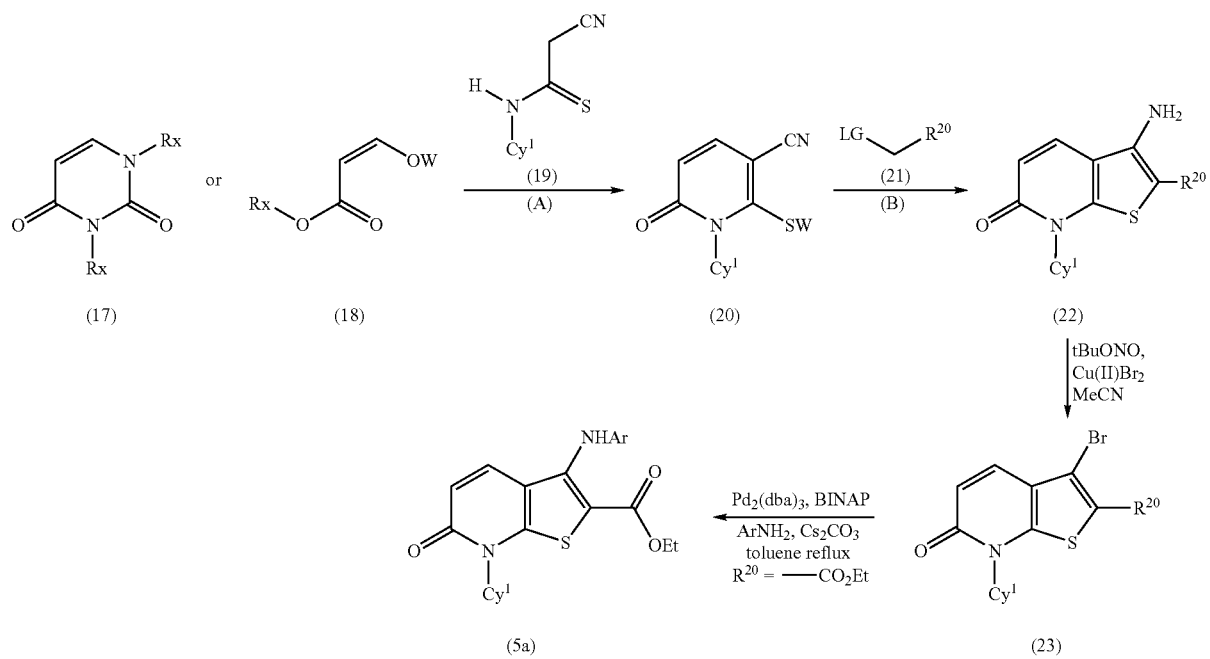

LG = leaving group e.g. Br or Cl
$R^{20}$ = Ester or nitrile

Thus, in step (A) of the reaction scheme a compound of formula (17) or (18), where Rx is an optionally substituted alkyl group, e.g. methyl, and W is a hydrogen atom, metal ion or amine salt, may be reacted with a thioamide of formula (19). The reaction may be performed in the presence of a base. Appropriate bases may include, but are not limited to, lithium bases such as n-butyl- or tert-butyllithium or lithium diisopropylamide (LDA), silazanes, e.g. lithium hexamethyldisilazane (LiHMDS) or sodium hexamethyldisilazane (NaHMDS), carbonates, e.g. potassium carbonate, alkoxides, e.g. sodium ethoxide, sodium methoxide or potassium tert-butoxide, hydroxides, e.g. NaOH, hydrides, e.g. sodium hydride, and organic amines, e.g. triethylamine or diisopropylethylamine or a cyclic amine such as N-methylmorpholine or pyridine. The reaction may be performed in an organic solvent such as an amide, e.g. a substituted amide such as N,N-dimethylformamide, an ether, e.g. a cyclic ether such as tetrahydrofuran or 1,4-dioxane, an alcohol, e.g. methanol, ethanol or propanol, or acetonitrile, at a temperature from ambient to the reflux temperature. In one particular aspect of the process the reaction is achieved using an alkoxide base, especially sodium ethoxide or sodium methoxide, in an alcoholic solvent, especially ethanol, at reflux temperature.

Intermediates of formula (17), where not commercially available, may be prepared using standard methodology (see, for example, Mir Hedayatullah, *J. Heterocyclic Chem.*, 1981, 18, 339). Similarly, intermediates of formula (18), where not commercially available, may be prepared using standard In a similar manner, intermediates of formula (19), if not commercially available, may be prepared using methods known to those skilled in the art (see, for example, Adhikari et al., *Aust. J. Chem.*, 1999, 52, 63-67). For example, an isothiocyanate of formula $Cy^1NCS$ may be reacted with acetonitrile in the presence of a base, e.g. NaHMDS, in a suitable solvent, e.g. tetrahydrofuran, optionally at a low temperature, e.g. around −78° C. According to the nature of the group $Cy^1$, the intermediate of formula (19) may be prepared in situ, for example using the methods as described herein, followed by subsequent addition of a compound of formula (17) or (18).

During the course of this process an intermediate of formula (20) may be formed. If desired the intermediate may be isolated at the end of step (A) and subsequently reacted with intermediate (21) to form the desired amine (22). In some instances, however, it may advantageous not to isolate the intermediate of formula (20) and reaction (B) may be carried out directly with the reaction mixture of step (A).

If a different solvent is used during the second stage of the process, it may be necessary to evaporate the solvent, in vacuo, from the first stage of the process before proceeding with the second stage. Once evaporated, the crude solids from step (A) may be used in the next stage or they may be purified, for example by crystallisation, to yield an isolated intermediate, such as a compound of formula (20).

During step (B) of the process an intermediate of formula (21) may then be added to the reaction mixture or to the crude solids or purified product from step (A) in a suitable solvent. Suitable solvents include, but are not limited to, amides, e.g. a substituted amide such as N,N-dimethylformamide, alcohols, e.g. ethanol, methanol or isopropyl alcohol, ethers, e.g. a cyclic ether such as tetrahydrofuran or 1,4-dioxane, and acetonitrile. The reaction may be performed at a temperature from ambient up to the reflux temperature.

During the course of step (B) an intermediate of formula (24):

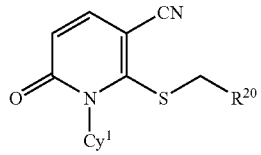

(24)

may be observed or even isolated, depending upon the nature of the group $R^{20}$. The intermediate of formula (24) may be converted to a compound of formula (22) using the methods described above. In this situation it may be necessary to add a base, in order for the reaction to proceed to completion. Appropriate bases include carbonates, e.g. caesium or potassium carbonate, alkoxides, e.g. potassium tert-butoxide, hydrides, e.g. sodium hydride, or organic amines, e.g. triethylamine or diisopropylethylamine or cyclic amines such as N-methylmorpholine or pyridine.

Amines of formula (22) can be converted to bromides of formula (23) by standard methods such as for example by the Sandmeyer reaction as previously described for compounds of formula (11). Compounds of formula (5a) can then be prepared from these bromides by the palladium-catalysed amination reactions already described.

It will be appreciated that intermediates of formula (21), where not commercially available, may be prepared using standard methods known to those skilled in the art. For example, alcohol groups may be converted into leaving groups, such as halogen atoms or sulfonyloxy groups, using conditions known to the skilled artisan. For example, an alcohol may be reacted with thionyl chloride in a halogenated hydrocarbon, e.g., dichloromethane, to yield the corresponding chloride. A base, e.g. triethylamine, may also be used in the reaction.

The nitriles of formula (23a), which may be prepared from the reaction scheme depicted in Scheme 5 by providing that $R^{20}$ is —CN, are useful intermediates in the synthesis of intermediate carboxylic acids of formula (25a). This reaction may be performed by hydrolysis of the nitrile (23a) with a base such as an alkali metal hydroxide, e.g. a 2M aqueous solution of sodium hydroxide in an alcoholic solvent such as methanol or ethanol at reflux.

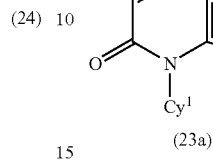

(23a)

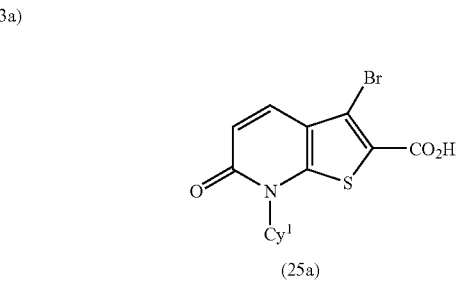

(25a)

It will be appreciated that intermediates, such as intermediates (17), (18), (19) or (21), if not available commercially, may also be prepared by methods known to those skilled in the art following procedures set forth in references such as Rodd's *Chemistry of Carbon Compounds*, volumes 1-15 and Supplementals (Elsevier Science Publishers, 1989), Fieser and Fieser's *Reagents for Organic Synthesis*, volumes 1-19 (John Wiley and Sons, 1999), *Comprehensive Heterocyclic Chemistry*, ed. Katritzky et al., volumes 1-8, 1984, and volumes 1-11, 1994 (Pergamon), *Comprehensive Organic Functional Group Transformations*, ed. Katritzky et al., volumes 1-7, 1995 (Pergamon), *Comprehensive Organic Synthesis*, ed. Trost and Fleming, volumes 1-9 (Pergamon, 1991), *Encyclopedia of Reagents for Organic Synthesis*, ed. Paquette, volumes 1-8 (John Wiley and Sons, 1995), Larock's *Comprehensive Organic Transformations* (VCH Publishers Inc., 1989) and March's *Advanced Organic Chemistry* (John Wiley and Sons, 1992).

In another process amides of formula (1a) may be prepared by the reactions detailed in Scheme 6 below.

Scheme 6

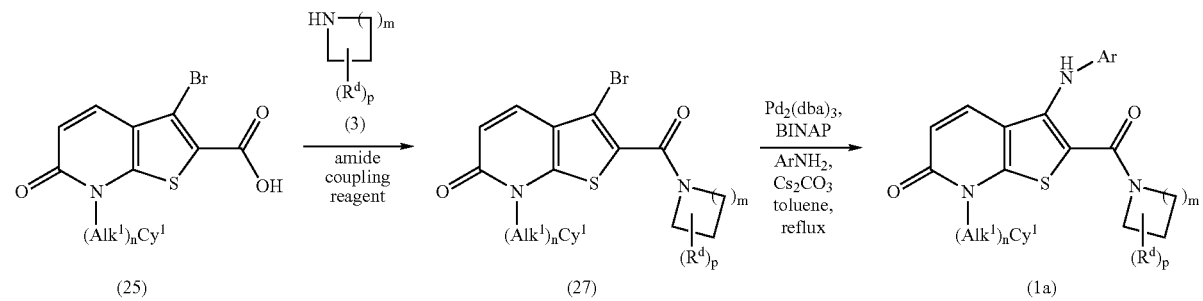

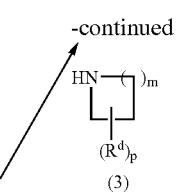
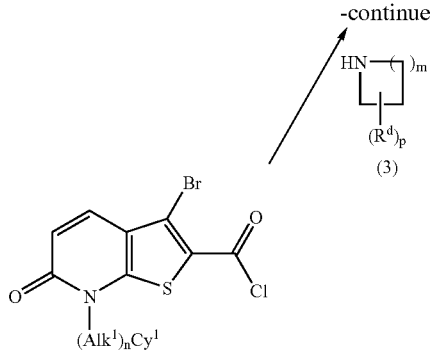

(26)

Thus, acids of formula (25) or (25a) may be converted to amides of formula (27) by reaction with amines of formula (3) in the presence of coupling reagents in the same way as previously described for the conversion of compounds (2) to amides of formula (1a). Alternatively, the carboxylic acids may be converted to acid chlorides of formula (26) by reaction with a chlorinating agent such as oxalyl chloride optionally in the presence of a catalytic amount of DMF in a solvent such as a halogenated hydrocarbon, e.g. dichloromethane, or an ether, e.g. a cyclic ether such as tetrahydrofuran, at around ambient temperature; or with a chlorinating agent such as thionyl chloride, typically in a solvent such as toluene, at the reflux temperature. The resultant acid chlorides may then be reacted with amines of formula (3) in a solvent such as a halogenated hydrocarbon, e.g. dichloromethane, in the presence of an amine base such as triethylamine at around ambient temperature to give amides of formula (27). Amides of formula (1a) may then be prepared from amides of formula (27) using a palladium-catalysed arylation procedure previously described in Scheme 1. During the course of the reactions described above it may be advantageous or necessary to protect the $R^d$ substituents that may be present. Conventional protecting groups may be used in accordance with standard practice [see, for example, Greene, T. W. in "Protective Groups in Organic Synthesis", John Wiley and Sons, 1999]. In some instances, deprotection may be the final step in the synthesis of a compound of formula (1a) and the processes according to the invention described hereinafter are to be understood to extend to such removal of protecting groups.

According to a further aspect of the invention a compound of formula (1) in which Y is an —S(O)$_2$— group may be prepared by the route set out in Scheme 7.

Scheme 7

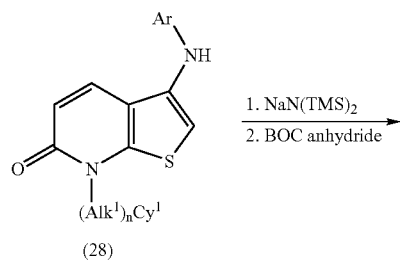

(28)

1. NaN(TMS)$_2$
2. BOC anhydride

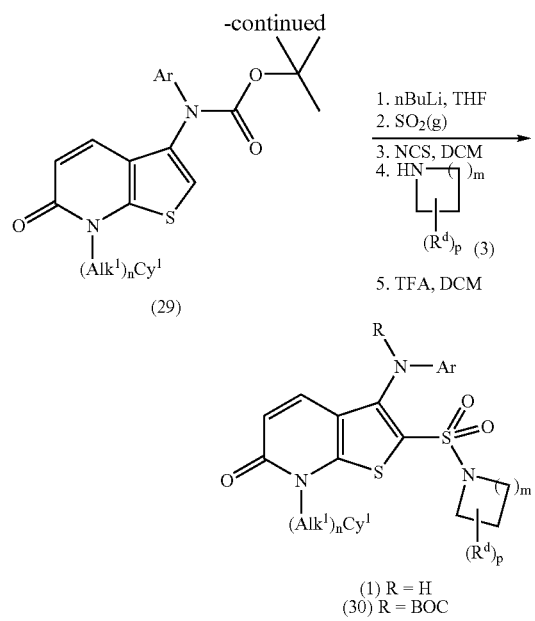

(1) R = H
(30) R = BOC

Thus, a compound of formula (29) can be obtained by reaction of a compound of formula (28) with a metal amide base such as sodium bis(trimethylsilyl)amide in a solvent such as an ether, e.g. a cyclic ether such as tetrahydrofuran, at a temperature of around 0° C. and then adding di-tert-butyl dicarbonate in a solvent such as tetrahydrofuran and stirring at ambient temperature. A compound of formula (1) can then be prepared by the following reaction sequence. A compound of formula (29) is treated with a base such as an alkyl lithium, e.g. n-butyllithium, in a solvent such as an ether, e.g. a cyclic ether such as tetrahydrofuran, at a temperature of around −78° C. Sulfur dioxide gas is bubbled through the reaction mixture before allowing the reaction to warm to room temperature. Solvents are removed in vacuo and the crude material dissolved in a solvent such as a halogenated hydrocarbon, e.g. dichloromethane, and the mixture treated with a chlorinating reagent such as N-chlorosuccinimide at around ambient temperature. An amine of formula (3) can then be added to the reaction mixture to produce a compound of formula (30), where R=tert-butoxycarbonyl. A sulphonamide of formula (1) can then be prepared by treating a compound of formula (30) with an acid, e.g. a mineral acid such as HCl or an organic acid such as trifluoroacetic acid, in a solvent such as a halogenated hydrocarbon, e.g. dichloromethane. Intermediates of formula (28) may be obtained by decarboxylation of compounds of formula (2) with an acid such as a mineral acid, e.g. HCl, in a solvent such as an ether, e.g. a cyclic ether such as tetrahydrofuran or 1,4-dioxane, at a temperature from 50° C. up to the reflux temperature.

Where in the general processes described above intermediates such as alkylating agents of formula $Cy^1(Alk^1)_nZ$, reagents of formula $HSCH_2CO_2Et$ and any other intermediates required in the synthesis of compounds of the invention are not available commercially or known in the literature, they may be readily obtained from simpler known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other intermediates and in particular compounds of formula (1) where appropriate functional groups exist in these compounds. Particular examples of such methods are given in the Examples hereinafter.

Thus for example aromatic halogen substituents in the compounds may be subjected to halogen-metal exchange with a base, for example a lithium base such as n-butyl- or tert-butyllithium, optionally at a low temperature, e.g. around −78° C., in a solvent such as tetrahydrofuran and then quenched with an electrophile to introduce a desired substituent. Thus, for example, a formyl group may be introduced by using N,N-dimethylformamide as the electrophile, a thiomethyl group may be introduced by using dimethyldisulphide as the electrophile, an alcohol group may be introduced by using an aldehyde as the electrophile, and an acid may be introduced by using carbon dioxide as the electrophile. Aromatic acids of formula $ArCO_2H$ may also be generated by quenching Grignard reagents of formula $ArMgHal$ with carbon dioxide.

Aromatic acids of formula $ArCO_2H$ generated by this method and acid-containing compounds in general may be converted to activated derivatives, e.g. acid halides, by reaction with a halogenating agent such as a thionyl halide, e.g. thionyl chloride, a phosphorus trihalide such as phosphorus trichloride, or a phosphorus pentahalide such as phosphorus pentachloride, optionally in an inert solvent such as an aromatic hydrocarbon, e.g. toluene, or a chlorinated hydrocarbon, e.g. dichloromethane, at a temperature from about 0° C. to the reflux temperature, or may be converted into Weinreb amides of formula $ArC(O)N(OMe)Me$ by conversion to the acid halide as just described and subsequent reaction with an amine of formula $HN(OMe)Me$ or a salt thereof, optionally in the presence of a base such as an organic amine, e.g. triethylamine, in an inert solvent such as an aromatic hydrocarbon, e.g. toluene, or a chlorinated hydrocarbon, e.g. dichloromethane, at a temperature from about 0° C. to ambient temperature.

Ester groups such as $—CO_2Alk^6$ and $—CO_2R^4$ in the compound of formula (1) and intermediates thereto may be converted to the corresponding acid [$—CO_2H$] by acid- or base-catalysed hydrolysis depending on the nature of the group $Alk^6$ or $R^4$. Acid- or -base-catalysed hydrolysis may be achieved for example by treatment with an organic or inorganic acid, e.g. trifluoroacetic acid, in an organic solvent, e.g. dichloromethane, or a mineral acid such as hydrochloric acid in a solvent such as 1,4-dioxane, or an alkali metal hydroxide, e.g. lithium hydroxide, in an aqueous alcohol, e.g. aqueous methanol.

In a further example, $—OR^6$ [where $R^6$ represents an alkyl group such as methyl] in compounds of formula (1) and intermediates thereto may be cleaved to the corresponding alcohol $—OH$ by reaction with boron tribromide in a solvent such as a halogenated hydrocarbon, e.g. dichloromethane, at a low temperature, e.g. around −78° C.

Alcohol [$—OH$] groups may also be obtained by hydrogenation of a corresponding $—OCH_2R^{31}$ group (where $R^{31}$ is an aryl group) using a metal catalyst, for example palladium, on a support such as carbon in a solvent such as ethanol in the presence of ammonium formate, cyclohexadiene or hydrogen, from around ambient to the reflux temperature. In another example, $—OH$ groups may be generated from the corresponding ester [e.g. $—CO_2Alk^6$] or aldehyde [$—CHO$] by reduction, using for example a complex metal hydride such as lithium aluminium hydride or sodium borohydride in a solvent such as methanol.

In another example, alcohol [$—OH$] groups in the compounds may be converted to a corresponding $—OR^6$ group by coupling with a reagent $R^6OH$ in a solvent such as tetrahydrofuran in the presence of a phosphine, e.g. triphenylphosphine, and an activator such as diethyl, diisopropyl or dimethyl azodicarboxylate.

Aminosulphonylamino [$—NHSO_2NH_2$] groups in the compounds may be obtained, in another example, by reaction of a corresponding amine [$—NH_2$] with sulphamide in the presence of an organic base such as pyridine at an elevated temperature, e.g. the reflux temperature.

In another example, compounds containing a $—NHCSR^7$ or $—CSNHR^7$ group may be prepared by treating a corresponding compound containing a $—NHCOR^7$ or $—CONHR^7$ group with a thiation reagent, such as Lawesson's Reagent or $P_2S_5$, in an anhydrous solvent, for example a cyclic ether such as tetrahydrofuran, at an elevated temperature such as the reflux temperature.

In a further example, amine [$—NH_2$] groups may be alkylated using a reductive alkylation process employing an aldehyde and a reducing agent. Suitable reducing agents include borohydrides, for example sodium triacetoxyborohyride or sodium cyanoborohydride. The reduction may be carried out in a solvent such as a halogenated hydrocarbon, e.g. dichloromethane, a ketone such as acetone, or an alcohol, e.g. ethanol, where necessary in the presence of an acid such as acetic acid at around ambient temperature. Alternatively, the amine and aldehyde may be initially reacted in a solvent such as an aromatic hydrocarbon, e.g. toluene, and then subjected to hydrogenation in the presence of a metal catalyst, for example palladium, on a support such as carbon, in a solvent such as an alcohol, e.g. ethanol.

In a further example, amine [$—NH_2$] groups in compounds of formula (1) and intermediates thereto may be obtained by hydrolysis from a corresponding imide by reaction with hydrazine in a solvent such as an alcohol, e.g. ethanol, at ambient temperature.

In another example, a nitro [$—NO_2$] group may be reduced to an amine [$—NH_2$], for example by catalytic hydrogenation using for example hydrogen in the presence of a metal catalyst, for example palladium, on a support such as carbon in a solvent such as an ether, e.g. tetrahydrofuran, or an alcohol, e.g. methanol, or by chemical reduction using for example a metal, e.g. tin or iron, in the presence of an acid such as hydrochloric acid.

In a further example, amine [$—CH_2NH_2$] groups in compounds of formula (1) and intermediates thereto may be obtained by reduction of nitriles [$—CN$], for example by catalytic hydrogenation using for example hydrogen in the presence of a metal catalyst, for example palladium on a support such as carbon, or Raney® nickel, in a solvent such as an ether, e.g. a cyclic ether such as tetrahydrofuran, or an alcohol, e.g. methanol or ethanol, optionally in the presence of ammonia solution at a temperature from ambient to the reflux temperature, or by chemical reduction using for example a metal hydride, e.g. lithium aluminium hydride, in a solvent such as an ether, e.g. a cyclic ether such as tetrahydrofuran, at a temperature from 0° C. to the reflux temperature.

In another example, sulphur atoms in the compounds, for example when present in a group $L^1$ or $L^2$, may be oxidised to the corresponding sulphoxide or sulphone using an oxidising agent such as a peroxyacid, e.g. 3-chloroperoxybenzoic acid, in an inert solvent such as a halogenated hydrocarbon, e.g. dichloromethane, at around ambient temperature.

In a further example N-oxides of compounds of formula (1) may in general be prepared for example by oxidation of the corresponding nitrogen base as described above in relation to the preparation of intermediates of formula (5).

Salts of compounds of formula (1) may be prepared by reaction of compounds of formula (1) with an appropriate base in a suitable solvent or mixture of solvents, e.g. an organic solvent such as an ether, e.g. diethyl ether, or an alcohol, e.g. ethanol, using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt.

In another resolution process a racemate of formula (1) may be separated using chiral High Performance Liquid Chromatography. Alternatively, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in 0° C.

The following abbreviations are used:

NMM - N-methylmorpholine;
MeOH - methanol;
DCM - dichloromethane;
DIPEA - diisopropylethylamine;
Pyr - pyridine;
DMSO - dimethylsulphoxide;
Et$_2$O - diethyl ether;
THF - tetrahydrofuran;
MCPBA - 3-chloroperoxybenzoic acid;
FMOC - 9-fluorenylmethoxycarbonyl;
DBU - 1,8-diazabicyclo[5,4,0]undec-7-ene;
EtOAc - ethyl acetate;
BOC - tert-butoxycarbonyl;
AcOH - acetic acid;
EtOH - ethanol;
Ar - aryl;
iPr - isopropyl;
Me - methyl;
h - hour;
NBS - N-bromosuccinimide;
r.t. - room temperature;
dba - dibenzylideneacetone;

-continued

EDC - 1-[3-(dimethylamino)propyl]-3-ethylcarbodiimide hydrochloride;
HOBT - 1-hydroxybenzotriazole hydrate;
BINAP - 2,2'-bis(diphenylphosphino)-1-1'-binaphthyl;
DMF - N,N-dimethylformamide;
DME - ethylene glycol dimethyl ether;
p.s.i. - pounds per square inch;
MTBE - methyl tert-butyl ether;
m.p. - melting point.

All NMRs were obtained either at 300 MHz or 400 MHz.

Compounds were named with the aid of either Beilstein Autonom supplied by MDL Information Systems GmbH, Theodor-Heuss-Allee 108, D-60486 Frankfurt, Germany, or ACD Labs Name (v.6.0) supplied by Advanced Chemical Development, Toronto, Canada.

LCMS retention times (RT) quoted were generated on a Hewlett Packard 1100 LC/MS using the following method: Phenomenex Luna 3 $\mu C_{18}(2)$ 50×4.6 mm column; mobile phase A=0.1% formic acid in water; mobile phase B=0.1% formic acid in MeCN; flow rate of 0.9 mLmin$^{-1}$, column temperature 40° C.

Gradient:

| Time (minutes) | % B | % A |
| --- | --- | --- |
| Initial | 5 | 95 |
| 2.0 | 95 | 5 |
| 3.0 | 95 | 5 |
| 5.0 | 5 | 95 |
| 5.5 | end | end |

Where stated alternative LCMS conditions (Conditions B) were used:

LCMS retention times (RT) quoted were generated on a Hewlett Packard 1100/ThermoFinnigan LCQ Duo LC/MS system using Electrospray ionisation and the following LC method: Phenomenex Luna C$_{18}$(2) 5µ 100 mm×4.6 mm column; mobile phase A=0.08% formic acid in water; mobile phase B=0.08% formic acid in MeCN; flow rate of 3.0 mLmin$^{-1}$, column temperature 35° C.

Gradient:—

| Time (min) | % A | % B |
| --- | --- | --- |
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Intermediate 1

Ethyl 3-aminothieno[2,3-b]pyridine-2-carboxylate

A mixture of 2-chloro-3-cyanopyridine (330 g, 2.3 mol), ethyl 2-mercaptoacetate (361.2 g, 3.0 mol), sodium carbonate (265 g, 2.5 mol) and EtOH (1.2L) was heated to reflux for 4.5 hours. The reaction mixture was cooled to ambient temperature and added to water (15L). The resultant precipitate was stirred for 30 minutes and then filtered. The filter cake was washed with two portions of water (2×2.5L) and dried to constant weight under vacuum at 45° C. to yield the title compound as a brown solid (493.1 g, 93.2%). δH (CDCl$_3$) 8.68 (1H, dd, J 4.7, 1.2 Hz), 7.93 (1H, dd, J 8.5, 1.2 Hz), 7.29 (1H, dd, J 8.5, 4.7 Hz), 5.90 (2H, b), 4.38 (2H, q, J 7.0 Hz), 1.40 (3H, t, J 7.0 Hz). LCMS RT 2.9 minutes, 223 (M+H)$^+$.

Intermediate 2

Ethyl 3-bromothieno[2,3-b]pyridine-2-carboxylate

Intermediate 1 (363.6 g) was added in portions over two hours to a mixture of copper(II) bromide (403.3 g), tert-butyl nitrite (220.6 g) and acetonitrile (3.6L) stirred at a temperature of 20 to 25° C. The mixture was stirred at 20° C. for 2 hours before it was slowly added to 2M HCl(aq) (4.2L). The reaction mixture slurry was filtered and the solids were washed with water (500 mL). The combined filtrate was extracted with ethyl acetate (8L); this ethyl acetate solution was washed with 2M HCl(aq) (2.2L). The solids were dissolved in ethyl acetate (6L); this solution was washed twice with 2M HCl(aq) (4.4L and 2.2L). The two ethyl acetate solutions were then combined and washed with 2M HCl(aq) (2.2L) and twice with water (2×2L). The ethyl acetate solution was then dried (MgSO$_4$), filtered and concentrated in vacuo at 40 mbar and 60° C. to give a solid residue. This was broken up and dried to constant weight under vacuum at 45° C. to yield the title compound as a brown solid (458.5 g, 97.9%). δH (DMSO-d6) 8.89 (1H, d, J 4.7 Hz), 8.47 (1H, d, J 8.6 Hz), 7.71 (1H, dd, J 8.6, 4.7 Hz), 4.46 (2H, q, J 7.2 Hz), 1.40 (3H, t, J 7.2 Hz). LCMS RT 3.8 minutes, 288 (M+H)$^+$.

Intermediate 3

Ethyl 3-Bromothieno[2,3-b]pyridine-2-carboxylate N-oxide

To a slurry of Intermediate 2 (214 g, 0.747 mol) in DCM (2140 mL) under nitrogen was added 70% mCPBA (240 g, 0.97 mol) portionwise over 0.5 h. The reaction was then stirred at room temperature for 18 h. The reaction mixture was quenched with water (800 mL) and pH adjusted to 8.5 with 10% w/v sodium carbonate solution (1250 mL). The basic aqueous layer was removed and the organic layer washed with water until pH 7. The organic layer was concentrated in vacuo and the crude title product was recovered as a tan solid. The crude product was purified by slurrying in MTBE (600 mL) for 1 h at 0-5° C. to give the title compound (174 g, 77%). δH (CDCl$_3$) 8.44 (1H, dd, J 6.2, 0.8 Hz), 7.87 (1H, dd, J 8.3, 0.8 Hz), 7.48 (1H, dd, J 8.3, 6.2 Hz), 4.49 (2H, q, J 7.1 Hz), 1.48 (3H, t, J 7.1 Hz). LCMS (ES$^+$) RT 2.61 minutes, 302 (M+H)$^+$.

Intermediate 4

Ethyl 3-bromo-6-oxo-6,7-dihydrothieno[2,3-b]pyridine-2-carboxylate

To a suspension of Intermediate 3 (95 g, 0.32 mol) in DMF (950 mL) and stirred at room temperature was added trifluoroacetic anhydride (198 g, 131 mL, 0.94 mol) dropwise over a 30 minute period (slight exotherm observed). After complete addition the reaction was stirred for a further 45 minutes at room temperature. The excess trifluoroacetic anhydride was removed under vacuum and the reaction mixture concentrated to approximately half the original volume. The resulting dark coloured solution was then poured onto a mixture of water (1L) and toluene (400 mL). The mixture was left to stand for around 10 minutes and then the precipitate was collected by filtration. The precipitate was washed with toluene (3×50 mL) and then dried in a vacuum oven at 50-60° C. This gave the title compound as a beige coloured solid (68.5 g, 72.1%). δH (DMSO-d6) 12.20 (1H, brs), 7.75 (1H, d, J 9.0 Hz), 6.50 (1H, d, J 9.0 Hz), 4.15 (2H, q, J 7.1 Hz), 1.12 (3H, t, J 7.1 Hz). LCMS (ES$^+$) RT 2.86 minutes, 302 (M+H)$^+$. m.p. 261.7-268.1° C.

Intermediate 5

Ethyl 3-bromo-6-oxo-7-phenyl-6,7-dihydrothieno[2,3-b]pyridine-2-carboxylate

Method A

A 3L jacketed vessel was charged with Intermediate 4 (100 g, 0.332 mol), CuI (15.8 g, 0.083 mol), phenylboronic acid (80 g, 0.664 mol), pyridine (104 g, 1.32 mol) and acetonitrile (2.0L) and the mixture stirred at 40° C. Compressed air was vigorously blown through the reaction mixture for 6 hours. The compressed air was then turned off and the reaction mixture left to stir at 40° C. overnight. The next day the same process was repeated. After approximately 36 hours, HPLC indicated >97% conversion of starting material to the product. The resulting dark coloured reaction mixture was poured onto a mixture of water (1.2L) and concentrated hydrochloric acid (300 mL). The mixture was extracted with dichloromethane (2×1.5L) and the combined organics washed with 2M HCl (aq) (2×1.5L). The organic layer was separated, passed through a pad of MgSO$_4$, and concentrated in vacuo. The crude residue was recrystallised from toluene (600 ml) to give the title compound as a beige solid (93.85 g, 75.0%). δH (CDCl$_3$) 7.82 (1H, d, J 8.5 Hz), 7.70-7.62 (3H, m), 7.54-7.42 (2H, m), 6.70 (1H, d, J 8.5 Hz), 4.15 (2H, q, J 7.1 Hz), 1.14 (3H, t, J 7.1 Hz). LCMS (ES$^+$) RT 3.75 minutes, 378 (M+H)$^+$. MP=201.6-206.0° C.

Method B (Alternative Procedure)

To a 2 necked round bottomed flask was added in sequence Intermediate 4 (302 mg, 1.00 mmol), copper(II) acetate (278 mg, 1.50 mmol), phenylboronic acid (488 mg, 4.00 mmol), DCM (5 mL) and pyridine (158 mg, 2.00 mmol). The reaction was stirred at room temperature for 18 h with the exclusion of moisture. The reaction was then diluted with DCM (50 mL), washed with 2M HCl(aq) (50 mL), the aqueous was re-extracted with DCM (50 mL). The combined organics were then washed with water (50 mL), dried (MgSO$_4$) and concentrated in vacuo. The crude product was purified by a slurry in methanol (12 mL), to give the title compound as a beige solid (270 mg, 72%). δH (CDCl$_3$) 7.82 (1H, d, J 8.5 Hz), 7.70-7.62 (3H, m), 7.54-7.42 (2H, m), 6.70 (1H, d, J 8.5 Hz), 4.15 (2H, q, J 7.1 Hz), 1.14 (3H, t, J 7.1 Hz). LCMS (ES$^+$) RT 3.75 minutes, 378 (M+H)$^+$.

Intermediate 6

Ethyl 3-bromo-7-(4-methylphenyl)-6-oxo-6,7-dihydrothieno[2,3-b]pyridine-2-carboxylate A flask was charged with Intermediate 4 (15.1 g, 0.05 mol), copper(II) acetate (13.62 g, 0.075 mol), 4-tolylboronic acid (14.0 g, 0.1 mol), DCM (500 mL) and pyridine (25 mL, 0.3 mol) and the mixture stirred at r.t. for 24 h. The reaction mixture was washed with 2M HCl (2×200 mL), 5% NaOH (aq) (200 mL), brine (200 mL) and dried (MgSO$_4$). Solvent was removed in vacuo and the resultant solid triturated with methanol to give the title compound as a solid (15.7 g). δH (CDCl$_3$) 7.76 (1H, d, J 9.7 Hz), 7.33 (2H, d, J 8.3 Hz), 7.18 (2H, d, J 8.3 Hz), 6.64 (1H, d, J 9.7 Hz), 4.24 (2H, q, J 7.1 Hz), 2.39 (3H, s), 1.26 (3H, t, J 7.1 Hz). LCMS (ES$^+$) RT 3.86 minutes, 394 (M+H)$^+$.

Intermediate 7

Ethyl 3-bromo-7-(4-fluorophenyl)-6-oxo-6,7-dihydrothieno[2,3-b]pyridine-2-carboxylate From Intermediate 4 and 4-fluorophenylboronic acid by the method of Intermediate 6. White solid. δH (CDCl$_3$) 7.84 (1H, d, J 9.7 Hz), 7.41-7.37 (2H, m), 7.32-7.25 (2H, m), 6.72 (1H, d, J 9.7 Hz), 4.33 (2H, q, J 7.1 Hz), 1.34 (3H, t, J 7.1 Hz). LCMS (ES$^+$) RT 3.729 minutes, 397.8 (M+H)$^+$.

Intermediate 8

Ethyl 3-bromo-7-(4-chlorophenyl)-6-oxo-6,7-dihydrothieno[2,3-b]pyridine-2-carboxylate From Intermediate 4 and 4-chlorophenylboronic acid by the method of Intermediate 6. δH (CDCl$_3$) 7.86 (1H, d, J 9.6 Hz), 7.60 (2H, d, J 8.5 Hz), 7.37 (2H, d, J 8.5 Hz), 6.74 (1H, d, J 9.6 Hz), 4.35 (2H, q, J 7.1 Hz), 1.36 (3H, t, J 7.1 Hz). LCMS (ES$^+$) RT 3.937 minutes, 413 (M+H)$^+$.

Intermediate 9

Ethyl 3-bromo-7-(3-methylphenyl)-6-oxo-6,7-dihydrothieno[2,3-b]pyridine-2-carboxylate From Intermediate 4 and 3-methylphenylboronic acid by the method of Intermediate 6. δH (CDCl$_3$) 7.85 (1H, d, J 9.6 Hz), 7.51-7.48 (1H, m), 7.38-7.27 (1H, m), 7.29 (2H, br m), 6.75 (1H, d, J 9.6 Hz), 4.34 (2H, q, J 7.1 Hz), 2.46 (3H, s), 1.35 (3H, t, J 7.1 Hz). LCMS (ES$^+$) RT 3.865 minutes, 393 (M+H)$^+$.

Intermediate 11

Ethyl 3-bromo-7-(cyclopropylmethyl)-6-oxo-6,7-dihydrothieno[2,3-b]pyridine-2-carboxylate Sodium hydride (60% in mineral oil) (3.27 g, 81.4 mmol) was added in portions to a solution of Intermediate 4 (22.3 g, 74 mmol) in DMF (300 mL) at 0° C. The mixture was stirred at r.t. for 30 min then cyclopropylmethyl bromide (10 g, 74 mmol) was added slowly and the mixture heated at 60° C. overnight. The DMF was removed in vacuo and the residue partitioned between EtOAc and brine. The organic phase was dried (MgSO$_4$) and concentrated in vacuo. Purification by column chromatography (silica, 0% to 10% EtOAc in DCM) gave the title compound as a yellow solid (12.5 g, 47%). δH (CDCl$_3$) 7.57 (1H, d, J 9.5 Hz), 6.47 (1H, d, J 9.5 Hz), 4.22 (2H, q, J 7.0 Hz), 3.87 (2H, d, J 7.1 Hz), 1.26-1.19 (4H, m), 0.43-0.37 (4H, m). LCMS (ES$^+$) RT 3.80 minutes, 357 (M+H)$^+$.

Intermediate 12

Ethyl 3-[(4-fluoro-3-methylphenyl)amino]-6-oxo-7-phenyl-6,7-dihydrothieno[2,3-b]pyridine-2-carboxylate Intermediate 5 (1.00 g, 2.64 mmol), tris(dibenzylideneacetone)dipalladium(0) (0.121 g, 0.132 mmol) and BINAP (0.164 g, 0.264 mmol) were stirred in toluene (12 mL) for 5 min. 4-Fluoro-3-methylaniline (0.397 g, 3.172 mmol) and cesium carbonate (1.205 g, 3.701 mmol) were added and the mixture was heated at reflux under N$_2$ for 24 h. The mixture was dissolved in THF (100 mL) and washed with water. The combined organics were dried (Na$_2$SO$_4$) and concentrated in vacuo. The residue was triturated with MeOH to produce the title compound as a white solid (0.754 g). δH (DMSO-d6) 8.72 (1H, s), 7.67-7.60 (3H, m), 7.51-7.49 (2H, m), 7.18-7.10 (3H, m), 7.09-6.99 (1H, m), 6.39 (1H, d, J 9.7 Hz), 4.15 (2H, q, J 7.07 Hz), 2.22 (3H, s), 1.72 (3H, t, J 7.08 Hz). LCMS (ES$^+$) 423 (M+H)$^+$.

Intermediate 13

Ethyl 3-[(2,4-difluorophenyl)amino]-6-oxo-7-phenyl-6,7-dihydrothieno[2,3-b]pyridine-2-carboxylate Tris(dibenzylideneacetone)dipalladium(0) (1.21 g, 1.32 mmol) was added to a mixture of Intermediate 5 (10 g, 26.4 mmol), caesium carbonate (12.05 g, 37.0 mmol), 2,4-difluoroaniline (4.1 g, 3.23 mL, 31.7 mmol) and BINAP (1.65 g, 2.64 mmol) in anhydrous toluene (80 mL) and the reaction heated to reflux under nitrogen for 4 days. The reaction was cooled, partitioned between DCM and water and the organic phase dried (MgSO$_4$) and evaporated in vacuo. The crude residue was triturated with methanol to give the title compound as a white solid (9.87 g). δH (CDCl$_3$) 8.49 (1H, bs), 7.58-7.40 (3H, m), 7.32-7.25 (2H, m), 7.13-7.04 (1H, m), 7.01 (1H, d, J 9.8 Hz), 6.93-6.86 (1H, m), 6.82-6.75 (1H, m), 6.31 (1H, d, J, 9.8 Hz), 4.20 (2H, q, J 7.1 Hz), 1.23 (3H, J 7.1 Hz). LCMS (ES$^+$) RT 4.06 minutes, 427 (M+H)$^+$.

General Procedure for the Preparation of ethyl 3-anilino-6-oxo-7-phenyl-6,7-dihydrothieno[2,3-b] pyridine-2-carboxylate intermediates The Intermediate esters 14-26 were prepared following a procedure similar to that described for Intermediate 13. Therefore to an oven dried reaction flask was added a magnetic stirrer, the appropriate substituted aniline (1.2 equiv.), anhydrous toluene, Intermediate 5 (1.0 equiv.), caesium carbonate (1.4 equiv.), tris(dibenzylideneacetone)dipalladium (0) (5 mol %) and BINAP (10 mol %). The reactions were heated to reflux under nitrogen and with magnetic stirring for 24-48 h. Each reaction was then diluted with DCM, washed with water, dried (MgSO$_4$) and concentrated in vacuo. The crude products were either purified on silica eluting with a gradient of EtOAc in DCM or alternatively by trituration with methanol or ethyl acetate to give the title compounds as solids.

Intermediate 14

Ethyl 3-anilino-6-oxo-7-phenyl-6,7-dihydrothieno[2,3-b]pyridine-2-carboxylate

From Intermediate 5 and aniline to give the title compound as a white solid. δH (CDCl$_3$) 8.70 (1H, bs), 7.57-7.47 (3H, m), 7.33-7.25 (4H, m), 7.20-7.10 (4H, m), 6.27 (1H, d, J 9.7 Hz), 4.19 (2H, q, J 7.1 Hz), 1.22 (3H, t, J 7.1 Hz). LCMS (ES$^+$) RT 4.10 minutes, 391 (M+H)$^+$.

Intermediate 15

Ethyl 3-[(2-chlorophenyl)amino]-6-oxo-7-phenyl-6,7-dihydrothieno[2,3-b]pyridine-2-carboxylate From 2-chloroaniline and Intermediate 5 to give the title compound as a solid. δH (CDCl$_3$) 8.60 (1H, bs), 7.56-7.48 (3H, m), 7.40-7.38 (1H, m), 7.36-7.32 (2H, m), 7.20-7.15 (2H, m), 7.14-7.05 (1H, m), 7.05-6.98 (1H, m), 6.35 (1H, d, J 9.8 Hz), 4.21 (2H q, J 7.1 Hz), 1.23 (3H, t, J 7.1 Hz). LCMS (ES⁺) RT 4.38 minutes, 425 (M+H)⁺.

Intermediate 16

Ethyl 3-[(3-cyanophenyl)amino]-6-oxo-7-phenyl-6,7-dihydrothieno[2,3-b]pyridine-2-carboxylate From 3-cyanoaniline and Intermediate 5 to give the title compound an off-white solid. δH (CDCl₃) 8.58 (1H, bs), 7.61-7.43 (3H, m), 7.40-7.20 (6H, m), 7.14 (1H, d, J 9.8 Hz), 6.38 (1H, d, J 9.8 Hz), 4.19 (2H, q, J 7.1 Hz), 1.23 (3H, t, J 7.1 Hz). LCMS (ES⁺) RT 3.78 minutes, 416 (M+H)⁺.

Intermediate 17

Ethyl 3-[(2-cyanophenyl)amino]-6-oxo-7-phenyl-6,7-dihydrothieno[2,3-b]pyridine-2-carboxylate From 2-cyanoaniline and Intermediate 5 to give the title compound. δH (CDCl₃) 8.72 (1H, bs), 7.61-7.47 (4H, m), 7.43-7.40 (1H, m), 7.36-7.31 (2H, m), 7.22-7.15 (1H, m), 7.11-7.00 (2H, m), 6.40 (1H, d, J 9.8 Hz), 4.22 (2H, q, J 7.1 Hz), 1.24 (3H, t, J 7.1 Hz). LCMS (ES⁺) RT 3.80 minutes, 416 (M+H)⁺.

Intermediate 20

Ethyl 3-[(3-chloro-4-fluorophenyl)amino]-6-oxo-7-phenyl-6,7-dihydrothieno[2,3-b]pyridine-2-carboxylate From Intermediate 5 and 3-chloro-4-fluoroaniline to give the title compound as a solid. δH (CDCl₃) 8.70 (1H, s), 7.67-7.59 (3H, m), 7.44-7.41 (2H, m), 7.24-7.02 (4H, m), 6.43 (1H, d, J 9.8 Hz), 4.28 (2H, q, J 7.1 Hz), 1.31 (3H, t, J 7.1 Hz). LCMS (ES⁺) RT 4.245 minutes, 443 (M+H)⁺.

Intermediate 22

Ethyl 3-[(4-fluoro-3-methylphenyl)amino]-7-(4-chlorophenyl)-6-oxo-6,7-dihydrothieno[2,3-b]pyridine-2-carboxylate From Intermediate 8 and 4-fluoro-3-methylaniline to give the title compound as a solid. δH (CDCl₃) 8.72 (1H, br s), 7.58-7.38 (2H, m), 7.35-7.28 (2H, m), 6.99-6.98 (4H, m), 6.34 (1H, d, J 9.8 Hz), 4.28 (2H, q, J 7.1 Hz), 2.29 (3H, s), 1.32 (3H, t, J 7.1 Hz). LCMS (ES⁺) RT 4.57 minutes, 457 (M+H)⁺.

Intermediate 23

Ethyl 3-[(4-fluoro-3-methylphenyl)amino]-7-(3-methylphenyl)-6-oxo-6,7-dihydrothieno[2,3-b]pyridine-2-carboxylate From Intermediate 9 and 4-fluoro-3-methylaniline to give the title compound as a solid. δH (CDCl₃) 8.63 (1H, br s), 7.40-7.15 (1H, m), 7.30-7.27 (1H, m), 7.18-7.10 (2H,m), 7.04-6.90 (4H, m), 6.27 (1H, d, J 9.7 Hz), 4.18 (2H, q, J 7.1 Hz), 2.21 (3H, s), 2.20 (3H, s), 1.21 (3H, t, J 7.1 Hz). LCMS (ES⁺) RT 4.469 minutes, 437 (M+H)⁺.

Intermediate 24

Ethyl 3-[(3-methylphenyl)amino]-7-(3-methylphenyl)-6-oxo-6,7-dihydrothieno[2,3-b]pyridine-2-carboxylate From Intermediate 9 and 3-methylaniline to give the title compound as a solid. δH (CDCl₃) 8.55 (1H, br s), 7.32-7.28 (1H, m), 7.27-7.17 (1H, m), 7.08-7.00 (4H, m), 7.88-7.75 (3H, m), 6.15 (1H, d, J 9.8 Hz), 4.08 (2H, q, J 7.1 Hz), 2.27 (3H, s), 2.17 (3H, s), 1.12 (3H, t, J 7.1 Hz). LCMS (ES⁺) RT 4.543 minutes, 419 (M+H)⁺.

Intermediate 26

Ethyl 3-anilino-7-(cyclopropylmethyl)-6-oxo-6,7-dihydrothieno[2,3-b]pyridine-2-carboxylate From Intermediate 11 and aniline to give the title compound. Pale yellow solid. δH (CDCl₃) 8.71 (1H, br s), 7.29-7.22 (2H, m), 7.10-6.97 (4H, m), 6.18 (1H, d, J 9.7 Hz), 4.27 (2H, q, J 7.1 Hz), 3.94 (2H, d, J 7.2 Hz), 1.40-1.33 (1H, m), 1.32 (3H, t, J 7.1 Hz), 0.53-0.48 (4H, m). LCMS (ES⁺) RT 3.79 minutes, 369.0 (M+H)⁺.

Intermediate 27

Lithium 3-[(4-fluoro-3-methylphenyl)amino]-6-oxo-7-phenyl-6,7-dihydrothieno[2,3-b]pyridine-2-carboxylate Intermediate 12 (0.494 g, 1.170 mmol) was dissolved in EtOH/THF/H₂O (2:1:1) (20 mL), heated to 80° C. and treated with LiOH.H₂O (0.054 g, 1.287 mmol). Reaction was continued until no starting material remained (as judged by TLC). The solvent was removed in vacuo and the residue azeotroped with toluene to give the title compound as a beige solid (0.284 g). δH (DMSO-d6) 7.81-7.75 (3H, m), 7.64-7.62 (2H, m), 7.41-7.38 (1H, d, J 9.55 Hz), 7.20-7.15 (1H, t, J 9.01 Hz), 7.04-7.03 (1H, br m), 6.93-6.90 (1H, br m), 6.48-6.46 (1H, d, J 9.54 Hz), 2.35 (3H, s). LCMS (ES⁺) 395 (M+H)⁺.

Intermediate 28

Lithium 3-[(2,4-difluorophenyl)amino]-6-oxo-7-phenyl-6,7-dihydrothieno[2,3-b]pyridine-2-carboxylate The title compound was prepared from Intermediate 13 (6.34 g, 14.9 mmol) and lithium hydroxide monohydrate (686 mg, 16.4 mmol) following the method of intermediate 27. δH (DMSO-d6) 10.04 (1H, bs), 7.81 (3H, m), 7.69 (2H, m), 7.50 (1H, m), 7.48 (1H, d, J 9.6 Hz), 7.16 (2H, m), 7.56 (1H, d, J 9.6 Hz).

Intermediate 29

Ammonium 6-oxo-3-(phenylamino)-7-phenyl-6,7-dihydrothieno[2,3-b]pyridine-2-carboxylate A solution of sodium hydroxide (339 mg, 8.5 mmol, 1.1 equiv.) in water (20 mL) was added to a suspension of Intermediate 14 (3.0 g, 7.7 mmol, 1.0 equiv.) in ethanol (50 mL) and the mixture heated at reflux for 2 h. The bulk of the ethanol was removed in vacuo and the residue treated with sat. ammonium chloride solution(aq) (30 mL). The resultant solid was collected by filtration, washed with water (2×20 mL), Et$_2$O (2×20 mL) and dried in vacuo at room temperature to give the title compound as a white solid in quantitative yield. δH (DMSO-d6) 9.60 (1H, bs), 7.65-7.57 (3H, m), 7.49-7.46 (2H, m), 7.29-7.18 (3H, m), 6.97-6.91 (3H, m), 6.34 (1H, d, J 9.6 Hz). LCMS (ES$^+$) RT 3.24 minutes, 363 (M+H)$^+$.

Intermediate 30

Sodium 7-(4-chlorophenyl)-3-[(4-fluoro-3-methylphenyl)amino]-6-oxo-6,7-dihydrothieno[2,3-b]pyridine-2-carboxylate The title compound was prepared from Intermediate 22 (1.0 g, 2.1 mmol) and sodium hydroxide (100 mg, 2.6 mmol, 1.2 equiv.) following a procedure analogous to that used for Intermediate 29. Instead of treating with a saturated ammonium chloride solution the volatiles were removed in vacuo and the residue was triturated with EtOAc to give the title compound as a solid (800 mg). δH (DMSO-d6) 9.74 (1H, bs), 7.67 (2H, dd, J 6.6, 2.1 Hz), 7.54 (2H, dd, J 6.6, 2.1 Hz), 7.24 (1H, d, J 9.6 Hz), 7.20-7.01 (1H, m), 6.90-6.80 (1H, m), 6.85-6.75 (1H, m), 6.31 (1H, d, J 9.5 Hz), 4.68 (3H, s). LCMS (ES$^+$) RT 3.51 minutes, 429 (M+H)$^+$.

Intermediate 31

Sodium 3-[(4-fluoro-3-methylphenyl)amino]-7-(3-methylphenyl)-6-oxo-6,7-dihydrothieno[2,3-b]pyridine-2-carboxylate The title compound was prepared from Intermediate 23 (1.0 g, 2.2 mmol) and sodium hydroxide (183 mg, 4.4 mmol) following the procedure of Intermediate 30 to give the title compound as a solid (1.0 g). δH (DMSO-d6) 7.56 (1H, t, J 7.7 Hz), 7.44 (1H, d, J 7.7 Hz), 7.38-7.24 (3H, m), 7.07 (1H, t, J 9.1 Hz), 6.96-6.91 (1H, m), 6.88-6.75 (1H, m), 6.37 (1H, d, J 9.6 Hz), 2.47 (3H, s), 2.25 (3H, s).

Intermediate 32

Sodium 3-[(3-methylphenyl)amino]-7-(3-methylphenyl)-6-oxo-6,7-dihydrothieno[2,3-b]pyridine-2-carboxylate The title compound was prepared from Intermediate 24 (1.0 g, 2.3 mmol) and sodium hydroxide (140 mg, 3.5 mmol) following the procedure of Intermediate 30 to give the title compound as a solid (842 mg). δH (DMSO-d6) 9.81 (1H, bs), 7.55 (1H, t, J 7.6 Hz), 7.47 (1H, d, J 12 Hz), 7.42-7.24 (3H, m), 7.18 (1H, t, J 7.7 Hz), 6.80-6.75 (3H, m), 6.37 (1H, J 9.5 Hz), 2.46 (3H, s), 2.31 (3H, s).

Intermediate 33

Sodium 3-[(3-Chloro-4-fluorophenyl)amino]-6-oxo-7-phenyl-6,7-dihydrothieno[2,3-b]pyridine-2-carboxylate The title compound was prepared from Intermediate 20 (1.0 g, 2.2 mmol) and sodium hydroxide (100 mg, 2.69 mmol) following the procedure of Intermediate 30 to give the title compound as a solid (680 mg). δH (DMSO-d6) 9.78 (1H, bs), 7.61-7.59 (3H, m), 7.55-7.46 (2H, m), 7.30-7.24 (2H, m), 7.09-7.06 (1H, m), 6.90-6.88 (1H, m), 6.34 (1H, d, J 9.4 Hz). LCMS (ES$^+$) RT 3.41 minutes, 414 (M+H)$^+$.

Intermediate 34

Pentafluorophenyl 3-[(4-fluoro-3-methylphenyl)amino]-6-oxo-7-phenyl-6,7-dihydrothieno[2,3-b]pyridine-2-carboxylate EDC (0.163 g, 0.852 mmol) was added to a solution of Intermediate 27 (0.284 g, 0.710 mmol) in DMF (10 mL) and the mixture stirred at r.t. for 30 min. Pentafluorophenol (0.196 g, 1.065 mmol) was added and the mixture stirred at r.t. for 24 h. The solvent was removed in vacuo and the residue was dissolved in DCM which was then washed with water, dried (MgSO$_4$) and concentrated in vacuo. Purification by column chromatography (silica, 50% Hexane/EtOAc) to produce the title compound as a white solid (0.226 g). δH (DMSO-d6) 8.96 (1H, s), 7.07-6.95 (5H, br m), 7.55-7.39 (4H, br m), 6.29 (1H, d, J 9.86 Hz), 2.08 (3H, s). LCMS (ES$^+$) 561 (M+H)$^+$.

Intermediate 35

Pentafluorophenyl 3-[(2,4-difluorophenyl)amino]-6-oxo-7-phenyl-6,7-dihydrothieno[2,3-b]pyridine-2-carboxylate The title compound was prepared from Intermediate 28 following the method of Intermediate 34 to give the product as a white solid. δH (CDCl$_3$) 8.66 (1H, bs), 7.76 (3H, m), 7.58 (2H, m), 7.47 (1H, m), 7.14 (3H, m), 6.54 (1H, d, J 9.9 Hz). LCMS (ES$^+$) RT 4.57 minutes, 565 (M+H)$^+$.

Intermediate 36

3-Bromo-6-oxo-7-phenyl-6,7-dihydrothieno[2,3-b]pyridine-2-carboxylic acid

Sodium hydroxide (1.83 g, 45.8 mmol, 1.1 equiv.) was added to a suspension of Intermediate 5 (15.75 g, 41.6 mmol, 1.0 equiv.) in ethanol (78 mL) and water (78 ml) at room temperature. The reaction mixture was then heated to reflux. Once reflux was attained the solid material had gone into solution and analysis by HPLC indicated complete conversion to the acid. The reaction mixture was then cooled to ~70° C. and c.hydrochloric acid (46 ml) added over a 10 minute period. The reaction was allowed to cool to room temperature and the resultant solid collected by filtration, washed with water (3×25 ml) and dried in vacuo to give the title compound as a beige solid (13.81 g, 97%). δH (DMSO-d6) 8.13 (1H, d, J 9.6 Hz), 7.92-7.80 (3H, m), 7.78-7.74 (2H, m), 6.92 (1H, d, J 9.6 Hz).

Intermediate 37

3-Bromo-7-(4-methylphenyl)-6-oxo-6,7-dihydrothieno[2,3-b]pyridine-2-carboxylic acid The title compound was prepared from Intermediate 6 (16.0 g, 40.3 mmol) following the method of Intermediate 36 to give the product as a solid (13.84 g). δH (DMSO-d6) 7.85 (1H, d, J 9.6 Hz), 7.45-7.38 (4H, m), 6.65 (1H, d, J 9.6 Hz), 2.42 (3H, s).

Intermediate 38

3-Bromo-7-(4-fluorophenyl)-6-oxo-6,7-dihydrothieno[2,3-b]pyridine-2-carboxylic acid A solution of lithium hydroxide monohydrate (0.87 g, 20.8 mmol) in water (30 mL) was added to a solution of Intermediate 7 (5.5 g, 13.9 mmol) in dioxane (100 mL) and the reaction stirred at r.t. for 4 h. Concentrated hydrochloric acid was added dropwise until the product had precipitated. The resultant solid was collected by filtration, washed with water (2×30 mL), diethyl ether (2×30 mL) and dried in a vacuum oven to give the title compound as a solid (4.65 g, 91%). δH (DMSO-d6) 7.66 (1H, d, J 9.6 Hz), 7.43-7.38 (2H, m), 7.30-7.24 (2H, m), 6.46 (1H, d, J 9.6 Hz).

Intermediate 39

3-Bromo-2-{[(2R)-2-(hydroxymethyl)pyrrolidin-1-yl]carbonyl}-7-phenylthieno[2,3-b]pyridin-6(7H)-one To a solution of Intermediate 36 (10.0 g, 28.6 mmol) and DMF (2 drops) in THF (150 mL) was added oxalyl chloride (3.26 mL, 37.4 mmol), via syringe, over a 30 minute period. The reaction mixture was stirred for a further 30 minutes at room temperature before removing solvent and excess reagent in vacuo to give the intermediate acid chloride as a beige solid. This acid chloride was dissolved in DCM (150 mL) and added over 45 minutes to a mixture of (R)-2-pyrrolidinemethanol (2.88 g, 28.5 mmol) and triethylamine (4.36 mL, 31.3 mmol) in 100 mL of dichloromethane. After complete addition the reaction was stirred for 1 h at ambient temperature. The reaction mixture was poured onto water (200 mL), the DCM layer separated and the aqueous re-extracted with DCM (100 mL). The combined organic layers were then washed with water (200 mL), dried (MgSO$_4$) and evaporated to give the title compound as a light brown solid (12.83 g). δH (CDCl$_3$) 7.70 (1H, d, J 9.6 Hz), 7.50-7.60 (3H, m), 7.35-7.45 (2H, m), 6.75 (1H, d, J 9.6 Hz), 4.25-4.35 (1H, m), 4.00 (1H, br s), 3.45-3.80 (4H, m), 1.52-2.55 (4H, m). LCMS (ES$^+$) RT 2.52 minutes, 433.1 (M+H)$^+$.

Intermediate 40

3-Bromo-2-{[(2R)-2-(hydroxymethyl)pyrrolidin-1-yl]carbonyl}-7-(4-methylphenyl)thieno[2,3-b]pyridin-6(7H)-one To a suspension of Intermediate 37 (6.4 g, 17.5 mmol) in DCM (80 mL) was added EDC (5.04 g, 26 mmol) and the reaction stirred at r.t. for 1 h. (R)-2-pyrrolidinemethanol (2.6 mL, 26 mmol) was added and the reaction stirred for 18 h at room temperature. The reaction was diluted with DCM (10 mL), washed with brine, dried (MgSO$_4$) and concentrated in vacuo. The crude residue was purified by chromatography (silica, 30-50% EtOAc in DCM) to give the title compound as a white solid (3.44 g, 43%). δH (CDCl$_3$) 7.65 (1H, d, J 9.6 Hz), 7.37 (2H, d, J 8.2 Hz), 7.20-7.19 (2H, m), 6.66 (1H, d, J 9.6 Hz), 4.25-4.23 (1H, m), 3.80-3.40 (4H, m), 2.37 (3H, s), 2.13-2.04 (1H, m), 1.79-1.53 (3H, m). LCMS (ES$^+$) RT 2.92 minutes, 449 (M+H)$^+$.

Intermediate 41

3-Bromo-7-(4-fluorophenyl)-2-{[(2R)-2-(hydroxymethyl)pyrrolidin-1-yl]carbonyl}-thieno[2,3-b]pyridin-6(7H)-one The title compound was prepared from Intermediate 38 and (R)-2-pyrrolidinemethanol following the method described for Intermediate 40 to give the product as a solid. LCMS (ES$^+$) RT 2.83 minutes, 452 (M+H)$^+$.

Intermediate 42

3-Bromo-7-phenyl-2-({(2R)-2-[(tetrahydro-2H-pyran-2-yloxy)methyl]pyrrolidin-1-yl}carbonyl)thieno[2,3-b]pyridin-6(7H)-one To a 1 L round bottomed flask was added the Intermediate 39 (12.5 g, 28.8 mmol), dihydropyran (12.1 g, 144.8 mmol), p-toluenesulphonic acid (55 mg, 0.29 mmol) and dichloromethane (5000 mL). The reaction mixture was then stirred at room temperature for 5 hours. The reaction mixture was poured onto water (200 mL), saturated brine (100 mL) and sodium bicarbonate solution (100 mL). The layers were separated and the aqueous layer re-extracted with dichloromethane (100 mL). The combined organic layers were then washed with the above aqueous mixture, dried (MgSO$_4$) and evaporated to dryness. Purification by column chromatography (270 g silica gel) eluting with ethyl acetate gave the title compound as a light brown solid/foam (12.73 g). δH (DMSO-d6) 7.80 (1H, d, J 9.6 Hz), 7.70-7.45 (5H, m), 6.60 (1H, d, J 9.6 Hz), 4.50 (1H, m), 4.15 (1H, br s), 3.35-3.80 (5H, m), 1.30-2.00 (10H, m). LCMS (ES$^+$) RT 3.65 minutes, 519.1 (M+H)$^+$.

Intermediate 43

3-Bromo-7-(4-methylphenyl)-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 40 (3.44 g, 7.6 mmol) following the procedure used for Intermediate 42. This gave the title compound as a light brown solid (4.85 g). δH (CDCl$_3$) 7.63 (1H, d, J 9.6 Hz), 7.28 (2H, d, J 7.8 Hz), 7.17 (2H, m), 6.63 (1H, d, J 9.6 Hz), 4.48-4.28 (2H, m), 3.85-3.30 (6H, m), 2.36 (3H, s), 2.15-1.70 (7H, m), 1.48-1.46 (3H, m). LCMS (ES$^+$) RT 3.69 minutes, 533 (M)$^+$.

Intermediate 44

3-Bromo-7-(4-fluorophenyl)-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 41 (1.0 g, 2.21 mmol) following the procedure used for Intermediate 42. This gave the title compound as a light brown oil (0.95 g). δH (CDCl$_3$) 7.90 (1H, d, J 9.6 Hz), 7.69 (2H, m), 7.56 (2H, t, J 8.7 Hz), 6.73 (1H, d, J 9.6 Hz), 4.61-4.57 (1H, m), 3.97-3.37 (8H, m), 1.97-1.50 (9H, m). LCMS (ES$^+$) RT 3.51 minutes, 560 (M+Na)$^+$.

Intermediate 45

3-[(2,4-Difluorophenyl)amino]-7-phenyl-2-({(2R)-2-[(tetrahydro-2H-pyran-2-yloxy)methyl]pyrrolidin-1-yl}carbonyl)thieno[2,3-b]pyridin-6(7H)-one To a dry 500 ml 2 necked round bottomed flask, fitted with nitrogen inlet/outlet, was added Cs$_2$CO$_3$ (11.2 g, 31.7 mmol), (+/−)-BINAP (1.53 g, 2.46 mmol), Intermediate 42 (12.73 g, 24.6 mmol) and Pd$_2$(dba)$_3$ (1.12 g, 1.22 mmol). To this mixture was added anhydrous toluene (200 mL), which had been thoroughly degassed, and then 2,4-difluoroaniline (3.49 g, 27.0 mmol) and the reaction heated at reflux under nitrogen for 48 h. The reaction mixture was cooled to ambient and then poured onto 1.0 M HCl(aq) (300 mL). This was extracted with dichloromethane (2×100 mL) and the combined organics washed with 1.0 M HCl(aq) (2×300 mL), dried (MgSO$_4$) and concentrated in vacuo to give a brown oil. The crude product was purified by column chromatography (silica, 3:2 ethyl acetate:heptane) to give the title compound as a light yellow solid (7.32 g). δH (DMSO-d6) 8.75 (1H, s), 7.75 (1H, d, J 8.3 Hz), 7.70-7.60 (3H, m), 7.55-7.43 (2H, m), 7.35-7.22 (1H, m), 7.05-6.88 (2H, m), 6.50 (1H, d, J 9.6 Hz), 4.62 (1H, bs), 4.45-4.30 (1H, m), 3.65-2.75 (6H, m), 1.90-1.20 (10H, m). LCMS (ES$^+$) RT 3.01 minutes, 566 (M+H)$^+$.

Intermediate 46

3-[(3-Methylphenyl)amino]-7-phenyl-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 42 (2.5 g, 4.84 mmol) and m-toluidine (0.62 mL, 5.8 mmol) following the method of Intermediate 45 to give the product as an orange solid (2.27 g). δH (CDCl$_3$) 7.76 (3H, m), 7.66 (3H, m), 7.30 (1H, m), 7.00 (3H, m), 6.54 (1H, d, J 9.7 Hz), 4.68 (1H, m), 4.65 (1H, m), 3.90-3.50 (6H, m), 2.46 (3H, s), 2.10-1.50 (10H, m). LCMS (ES$^+$) RT 3.99 minutes, 544 (M+H)$^+$.

Intermediate 47

3-[(3-chlorophenyl)amino]-7-phenyl-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 42 (1.7 g, 3.3 mmol) and 3-choroaniline (0.42 mL, 3.9 mmol) following the method of Intermediate 45 to give the product as a brown solid (900 mg). δH (CDCl$_3$) 7.66 (3H, m), 7.35 (3H, m), 7.19 (1H, m), 6.94 (2H, m), 6.93 (1H, m), 6.42 (1H, d, J 9.67 Hz), 4.53 (1H, m), 4.48 (1H, m), 3.75-3.36 (6H, m), 2.00-1.4 (10H, m). LCMS (ES$^+$) RT 3.90 minutes, 564 (M+H)$^+$.

Intermediate 48

3-[(2,4-Difluorophenyl)amino]-7-(4-methylphenyl)-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 43 (1.5 g, 2.8 mmol) and 2,4-difluoroaniline (0.35 mL, 3.3 mmol) following the method of Intermediate 45 to give the product as a solid (1.14 g, 69%). δH (CDCl$_3$) 9.33 (1H, bs), 7.39-7.30 (2H, m), 7.19-7.14 (3H, m), 6.96 (1H, dd, J 14.6, 9.1 Hz), 6.84 (1H, t, J 2.6 Hz), 6.73 (1H, t, J 8.2 Hz), 6.35 (1H, d, J 9.8 Hz), 4.48-4.38 (2H, m), 3.75-3.30 (6H, m), 2.39 (3H, s), 1.97-1.50 (4H, m), 1.49-1.25 (6H, m).

Intermediate 49

3-[(4-Fluoro-3-methylphenyl)amino]-7-(4-methylphenyl)-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 43 (1.5 g, 2.8 mmol) and 4-fluoro-3-methylaniline (0.42 mL, 3.3 mmol) following the method of Intermediate 45 to give the product as a solid (879 mg). δH (CDCl$_3$) 9.41 (1H, bs), 7.48-7.38 (2H, m), 7.28-7.13 (4H, m), 6.84-6.74 (3H, m), 6.30 (1H, d, J 9.8 Hz), 4.46-4.36 (2H, m), 3.71-3.25 (6H, m), 2.37 (3H, s), 2.15 (3H, s), 1.96-1.54 (6H, m), 1.45-1.40 (3H, m). LCMS (ES$^+$) RT 4.21 minutes, 576 (M+H)$^+$.

Intermediate 50

7-(4-Methylphenyl)-3-[(3-methylphenyl)amino]-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 43 (1.5 g, 2.8 mmol) and m-toluidine (0.37 mL, 3.3 mmol) following the method of Intermediate 45 to give the product as a solid (1.0 g, 63%). δH (CDCl$_3$) 9.29 (1H, m), 7.30-7.19 (5H, m), 7.09 (1H, t, J 8.3 Hz), 6.78-6.76 (3H, m), 6.32 (1H, d, J 9.7 Hz), 4.48-4.36 (2H, m), 3.76-3.32 (6H, m), 2.39 (3H, s), 2.23 (3H, s), 1.97-1.58 (6H, m), 1.54-1.42 (4H, m).

Intermediate 51

3-[(2,4-Difluorophenyl)amino]-7-(4-fluorophenyl)-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 44 (0.48 g, 0.896 mmol) and 2,4-difluoroaniline (0.11 mL, 1.08 mmol) following the method of Intermediate 45 to give the product as a yellow solid (206 mg, 39%). LCMS RT 3.87 minutes, 606 (M+Na)$^+$.

Intermediate 52

3-[(4-Fluoro-3-methylphenyl)amino]-7-(4-fluorophenyl)-2-({(2R)-2-[(tetrahydro-2H-pyran-2-yloxy)methyl]pyrrolidin-1-yl}carbonyl)thieno[2,3-b]pyridin-6(7H)-one The title compound was prepared from Intermediate 44 (0.48 g, 0.896 mmol) and 3-methyl-4-fluoroaniline (0.135 g, 1.08 mmol) following the method of Intermediate 45 to give the product as a solid (90 mg). δH (CDCl$_3$) LCMS RT 3.94 minutes, 581 (M+H)$^+$.

Intermediate 53

3-Amino-7-(2-chlorophenyl)-6-oxo-6,7-dihydrothieno[2,3-b]pyridine-2-carbonitrile Acetonitrile (10 mL) was added to a solution of sodium bis(trimethylsilyl)amide (100 mL, 1.0M in THF, 100 mmol) in THF (50 mL) at −78° C. to give a thick white precipitate. 2-Chlorophenyl isothiocyanate (7.72 g, 45.45 mmol) was added to give a brown solution. The mixture was allowed to warm to r.t. over 1 h then diluted with EtOH (50 mL). N,N-Dimethyluracil (6.4 g, 45 mmol) was added and the mixture heated at reflux for 24 h. Volatiles were removed in vacuo and the residue dissolved in acetonitrile (100 mL). Chloroacetonitrile (2.85 mL, 45 mmol) was added and the mixture heated at 50° C. for 1 h, a second charge of chloroacetonitrile (2.85 mL, 45 mmol) was added and heating continued for 1.5 h. Some of the acetonitrile (~50 mL) was removed in vacuo and water was added to precipitate the product. The brown solid was filtered off, washed with water (50 mL) and Et$_2$O (50 mL)

Intermediate 54

3-Bromo-7-(2-chlorophenyl)-6-oxo-6,7-dihydrothieno[2,3-b]pyridine-2-carbonitrile Intermediate 53 (1.17 g, 3.88 mmol) was suspended in acetonitrile (20 mL). Copper(II) bromide (953 mg, 4.27 mmol) was added followed by tert-butyl nitrite (0.64 mL, 5.43 mmol). The mixture was stirred at r.t. for 3 h then partitioned between 2M HCl aq (100 mL) and EtOAc (100 mL). The organic layer was washed with 2M HCl aq (50 mL), 2M NaOH aq (50 mL) and water (25 mL), dried ($Na_2SO_4$) and concentrated in vacuo. Purification by column chromatography (silica, 0 to 5% EtOAc in DCM) gave the title compound as a pale brown solid (980 mg, 67%). δH ($CDCl_3$) 7.70 (1H, d, J 9.7 Hz), 7.61 (1H, dd, J 1.7, 7.7 Hz), 7.52-7.44 (2H, m), 7.34 (1H, dd, J 1.7, 7.7 Hz), 6.70 (1H, d, J 9.7 Hz). LCMS ($ES^+$) RT 3.56 minutes, 365 $(M+H)^+$.

Intermediate 55

3-Bromo-7-(2-chlorophenyl)-6-oxo-6,7-dihydrothieno[2,3-b]pyridine-2-carboxylic acid A mixture of Intermediate 54 (1.86 g, 5.0 mmol) in methanol (50 mL) and 2M NaOH aq (30 mL) was heated at reflux for 1.5 h. Volatiles were removed in vacuo and the residue treated with 2M HCl aq (75 mL). The mixture was stirred at r.t. overnight to give a fine off-white precipitate. The solid was filtered off and dried to give the title compound as an off-white solid (1.80 g, 92%). δH (DMSO-d6) 13.53 (1H, br s), 7.75 (1H, d, J 9.7 Hz), 7.64-7.62 (1H, m), 7.56-7.54 (1H, m), 7.51-7.42 (2H, m), 6.52 (1H, d, J 9.7 Hz). LCMS ($ES^+$) RT 3.13 minutes, 384 ($^{35}Cl^{79}Br$) $(M+H)^+$.

Intermediate 56

3-Bromo-7-(2-chlorophenyl)-2-{[(2R)-2-(hydroxymethyl)pyrrolidin-1-yl]carbonyl}thieno[2,3-b]pyridin-6(7H)-one Thionyl chloride (0.66 mL, 9.1 mmol) was added to a suspension of Intermediate 55 (1.75 g, 4.55 mmol) in chloroform (50 mL). The mixture was heated at 50° C. for 1 h. A second charge of thionyl chloride (0.66 mL, 9.1 mmol) was added and the mixture heated at 50° C. for a further 1 h then stirred at r.t. overnight and finally heated at reflux for a further 1 h to give a solution. Volatiles were removed in vacuo and the residue dissolved in DCM (30 mL). Triethylamine (0.25 mL, 9.1 mmol) and (R)-2-pyrrolidinemethanol (0.540 mL, 5.46 mmol) were added and the solution stirred at r.t. for 3 h. DCM (50 mL) was added and the mixture washed with 2M HCl aq (100 mL) and 2M NaOH aq (100 mL). The organic phase was dried ($Na_2SO_4$) and concentrated in vacuo to give the title compound as a pale brown foam (2.15 g, quant.). δH ($CDCl_3$) 7.70 (1H, d, J 9.6 Hz), 7.60-7.55 (1H, m), 7.48-7.32 (3H, m), 6.66 (1H, d, J 9.6 Hz), 4.28-4.16 (1H, br s), 3.70-3.48 (5H, m), 2.13-2.09 (1H, m), 1.92-1.81 (1H, m), 1.79-1.59 (2H, m). LCMS ($ES^+$) RT 2.91 minutes, 467 $(M+H)^+$.

Intermediate 57

3-Bromo-7-(2-chlorophenyl)-2-({(2R)-2-[(tetrahydro-2H-pyran-2-yloxy)methyl]pyrrolidin-1-yl}carbonyl)thieno[2,3-b]pyridin-6(7H)-one 3,4-Dihydro-2H-pyran (2.0 mL, 22.4 mmol) and p-toluenesulfonic acid monohydrate (45 mg, 5 mol %) were added to a solution of Intermediate 56 (2.10 g, 4.48 mmol) in DCM (25 mL). The mixture was stirred at r.t. for 48 h then diluted with DCM (50 mL) and washed with a mixture of $Na_2CO_3$ aq (50 mL) and brine (50 mL). The organic phase was dried ($Na_2SO_4$) and concentrated in vacuo. Purification by column chromatography (silica, 70% EtOAc in hexane) gave the title compound as a yellow solid (2.08 g, 84%). δH ($CDCl_3$) 7.69 (1H, m), 7.60-7.55 (1H, m), 7.50-7.32 (3H, m), 6.65 (1H, m), 4.50 (1H, br m), 4.29 (1H, br m), 3.70-3.31 (6H, m), 2.06-1.80 (4H, m), 1.69-1.40 (6H, m). LCMS ($ES^+$) RT 3.61 minutes, 551 $(M+H)^+$.

Intermediate 58

7-(2-Chlorophenyl)-3-[(4-fluoro-3-methylphenyl)amino]-2-({(2R)-2-[(tetrahydro-2H-pyran-2-yloxy)methyl]pyrrolidin-1-yl}carbonyl)thieno[2,3-b]pyridin-6(7H)-one From Intermediate 57 and 4-fluoro-3-methylaniline by the method of Intermediate 45. Yellow solid. δH ($CDCl_3$) 9.57 (1H, br s), 7.67-7.63 (1H, m), 7.54-7.40 (3H, m), 7.25 (1H, dd, J 1.0, 9.8 Hz), 6.95-6.85 (3H, m), 6.37 (1H, dd, J 1.0, 9.8 Hz), 4.56-4.50 (1H, m), 4.48-4.43 (1H, m), 3.84-3.40 (6H, m), 2.24 (3H, s), 2.02-1.45 (10H, m). LCMS ($ES^+$) RT 4.05 minutes, 596 $(M+H)^+$.

Intermediate 59

7-(2-Chlorophenyl)-3-[(2,4-difluorophenyl)amino]-2-({(2R)-2-[(tetrahydro-2H-pyran-2-yloxy)methyl]pyrrolidin-1-yl}carbonyl)thieno[2,3-b]pyridin-6(7H)-one From Intermediate 57 and 2,4-difluoroaniline by the method of Intermediate 45. Off-white solid. δH ($CDCl_3$) 9.45-9.40 (1H, m), 7.64-7.61 (1H, m), 7.52-7.39 (3H, m), 7.26 (1H, d, J 9.8 Hz), 7.07-7.01 (1H, m), 6.92-6.87 (1H, m), 6.82-6.77 (1H, m), 6.40 (1H, d, J 9.8 Hz), 4.53-4.41 (2H, m), 3.81-3.37 (6H, m), 2.00-1.85 (3H, m), 1.82-1.67 (1H, m), 1.65-1.32 (6H, m). LCMS ($ES^+$) RT 4.017 minutes, 622.1 $(M+Na)^+$.

Intermediate 60

3-[(2,4-Difluorophenyl)amino]-7-phenylthieno[2,3-b]pyridin-6(7H)-one

To a solution of Intermediate 28 (~4.20 g) in 1,4-dioxane (10 mL) was added 2M HCl(aq) (10 mL) and the reaction mixture heated at 70° C. for 1 h. The reaction was diluted with water (30 mL), extracted with EtOAc (3×30 mL) and the EtOAc extracts dried ($MgSO_4$) and concentrated in vacuo. The crude residue was purified by chromatography on silica (0-5% EtOAc in DCM) to give the title compound as a pale yellow solid (2.13 g). δH ($CDCl_3$) 7.94 (1H, d, J 9.4 Hz), 7.64-7.53 (3H, m), 7.46 (2H, m), 7.45 (1H, m), 7.20 (1H, m), 6.99 (1H, m), 6.48 (1H, d, J 9.4 Hz), 5.74 (1H, s). LCMS ($ES^+$) RT 3.54 minutes, 354.9 $(M+H)^+$.

Starting content on page 47:

and dried to give the title compound as a brown solid (14.3 g, quant.). δH (DMSO-d6) 8.10 (1H, d, J 9.7 Hz), 7.75-7.73 (1H, m), 7.65-7.54 (3H, m), 7.14 (2H, br s, $NH_2$), 6.54 (1H, d, J 9.7 Hz). LCMS ($ES^+$) RT 2.97 minutes, 302 $(M+H)^+$.

Intermediate 61 tert-Butyl (2,4-difluorophenyl)(6-oxo-7-phenyl-6,7-dihydrothieno[2,3-b]pyridin-3-yl)carbamate Sodium bis(trimethylsilyl)amide (6.0 mL, 1.0M in THF, 6 mmol) was added to a solution of Intermediate 60 (2.0 g, 5.65 mmol) in THF (50 mL) at 0° C. After 30 min, di-tert-butyl dicarbonate (1.36 g, 6.22 mmol) was added and the mixture stirred at r.t. for 1 h. The reaction mixture was partitioned between EtOAc and brine. The aqueous phase was extracted with EtOAc (×3), the combined organic extracts washed with brine, dried (MgSO$_4$) and concentrated in vacuo. Purification by column chromatography (silica, 10% EtOAc in DCM) gave the title compound (1.2 g, 47%). δH (CDCl$_3$) 7.45 (1H, d, J 9.5 Hz), 7.43-7.30 (3H, m), 7.22-7.19 (2H, m), 7.08-7.03 (1H, m), 6.76-6.65 (2H, m), 6.49-6.45 (2H, m), 1.26 (9H, s). LCMS (ES$^+$) RT 3.79 minutes, 455 (M+H)$^+$.

Intermediate 62 tert-Butyl (2,4-difluorophenyl)(2-{[(2R)-2-(hydroxymethyl)pyrrolidin-1-yl]sulfonyl}-6-oxo-7-phenyl-6,7-dihydrothieno[2,3-b]pyridin-3-yl)carbamate n-Butyllithium (0.54 mL of a 2.5M solution in hexanes, 1.35 mmol) was added to a solution of Intermediate 61 (600 mg, 1.32 mmol) in THF (30 mL) at −78° C. After 20 min, sulfur dioxide gas was bubbled through the solution for 5 min. The reaction mixture was allowed to warm to r.t. and solvents were removed in vacuo. The residue was dissolved in DCM (40 mL) and N-chlorosuccinimide (210 mg, 1.45 mmol) was added. After 90 min at r.t. a solution of (R)-2-pyrrolidinemethanol (146 mg, 1.45 mmol) in DCM (5 mL) was added and the mixture stirred for a further 30 min. The mixture was diluted with DCM and washed with brine. The organic phase was dried (MgSO$_4$) and concentrated in vacuo. Purification by column chromatography (silica, 5% to 15% EtOAc in DCM) gave the title compound (340 mg, 42%). δH (CDCl$_3$) 7.40-7.34 (4H, m), 7.18-7.10 (3H, m), 6.74-6.67 (1H, m), 6.65-6.58 (1H, m), 6.49 (1H, d, J 9.7 Hz), 3.95 (1H, br m), 3.92-3.24 (4H br m), 1.77-1.58 (5H, br m), 1.27 (9H, s). LCMS (ES$^+$) RT 3.55 minutes, 618 (M+H)$^+$.

Intermediate 63

Sodium 3-[(2-Chlorophenyl)amino]-6-oxo-7-phenyl-6,7-dihydrothieno[2,3-b]pyridine-2-carboxylate The title compound was prepared from Intermediate 15 (1.5 g, 3.52 mmol) and sodium hydroxide (150 mg) following the procedure of Intermediate 30 to give the title compound as a solid (1.47 g). δH (DMSO-d6) 9.97 (1H, bs), 9.56 (1H, d, J 9.6 Hz), 7.23-7.01 (2H, m), 7.26 (1H, t, J 7.0 Hz), 7.34 (1H, d, J 9.5 Hz), 7.47-7.13 (3H, m), 7.72-7.64 (3H, m). LCMS (ES$^+$) RT 3.42 minutes, 399 (M+H)$^+$.

Intermediate 64 rac-tert-Butyl [1-({3-[(2,4-difluorophenyl)amino]-6-oxo-7-phenyl-6,7-dihydrothieno[2,3-b]pyridin-2-yl}carbonyl)pyrrolidin-3-yl]carbamate To a solution of Intermediate 35 (300 mg, 0.53 mmol) in DCM (5 mL) was added tert-butyl pyrrolidin-3-ylcarbamate (300 mg, 1.6 mmol) and the reaction mixture stirred at r.t. for 18 h. The reaction mixture was concentrated in vacuo and the crude product purified by column chromatography (silica, 60% ethyl acetate in isohexane) to give the title compound as a yellow gum (277 mg). NMR δH (CDCl$_3$) 7.53 (3H, m), 7.19 (2H, m), 7.17 (1H, d, J 9.5 Hz), 6.98 (1H, m), 6.85 (1H, m), 6.73 (1H, m), 6.38 (1H, d, J 9.7 Hz), 4.50 (1H, bm), 3.76 (1H, m), 3.61 (2H, m), 3.58 (1H, m), 2.10 (1H, m), 1.80 (1H, m), 1.35 (9H, s). LCMS (ES$^+$) RT 3.50 minutes, 567 (M+H)$^+$.

Intermediate 65 tert-Butyl [(3S)-1-({3-[(2,4-difluorophenyl)amino]-6-oxo-7-phenyl-6,7-dihydrothieno[2,3-b]pyridin-2-yl}carbonyl)pyrrolidin-3-yl]carbamate To a solution of Intermediate 35 (1 g, 1.77 mmol) in DCM (30 mL) was added tert-butyl (S)-pyrrolidin-3-ylcarbamate (363 mg, 1.95 mmol) and the reaction mixture stirred at r.t. for 18 h. The reaction mixture was concentrated in vacuo and the crude product purified by column chromatography (silica, ethyl acetate) to give the title compound as a white solid (700 mg). LCMS (ES$^+$) RT 3.56 minutes, 567 (M+H)$^+$.

Intermediate 66 tert-Butyl [(3S)-1-({3-[(4-fluoro-3-methylphenyl)amino]-6-oxo-7-phenyl-6,7-dihydrothieno[2,3-b]pyridin-2-yl}carbonyl)pyrrolidin-3-yl]carbamate To a solution of Intermediate 34 (1.0 g, 1.79 mmol) in DCM (30 mL) was added tert-butyl (S)-pyrrolidin-3-ylcarbamate (372 mg, 2.0 mmol) and the reaction mixture stirred at r.t. for 18 h. The reaction mixture was concentrated in vacuo and the crude product purified by column chromatography (silica, 20% EtOAc in DCM) to give the title compound as an off white solid (1.2 g). NMR δH (CDCl$_3$) 9.61 (1H, bs), 7.65-7.55 (3H, m), 7.44-7.41 (2H, m), 7.25 (1H, d, J 9.7 Hz), 6.99-6.85 (3H, m), 6.40 (1H, d, J 9.7 Hz), 4.62 (1H, m), 4.23 (1H, m), 3.86-3.81 (1H, m), 3.70-3.66 (2H, m), 3.47 (1H, dd, J 10.3, 4.2 Hz), 2.27 (3H, d, J 1.9 Hz), 2.18-2.12 (1H, m), 1.91-1.85 (1H, m), 1.44 (9H, s). LCMS (ES$^+$) RT 3.64 minutes, 563 (M+H)$^+$.

Intermediate 67

Pentafluorophenyl 3-[(2-cyanophenyl)amino]-6-oxo-7-phenyl-6,7-dihydrothieno[2,3-b]pyridine-2-carboxylate A solution of LiOH monohydrate (390 mg, 9.27 mmol) in water (50 mL) was added to a suspension of Intermediate 17 (3.5 g, 8.42 mmol) in THF (50 mL) and EtOH (100 mL) and the mixture heated to reflux for 5 h. Solvent was removed in vacuo and the residue co-evaporated with toluene (×3) to give the intermediate lithium 3-[(2-cyanophenyl)amino]-6-oxo-7-phenyl-6,7-dihydrothieno[2,3-b]pyridine-2-carboxylate as a brown solid. This solid was dissolved in DMF (100 mL) and EDC (2.41 g, 12.6 mmol) added. The reaction was stirred for 20 minutes at r.t. before adding pentafluorophenol (2.89 g, 15.7 mmol) and then stirred for a further 18 h. DMF was removed in vacuo and the residue partitioned between DCM and water. The organic layer was separated, dried (MgSO$_4$) and concentrated in vacuo. The crude product was purified by column chromatography (silica, 30-100% EtOAc in isohexane) to give the title compound as a solid (1.35 g). LCMS (ES+) RT 4.06 minutes, 554 (M+H)+.

Intermediate 68

3-Bromo-7-(4-fluorophenyl)-6-oxo-6,7-dihydrothieno[2,3-b]pyridine-2-carbonyl chloride Thionyl chloride (5.2 mL, 71 mmol) was added dropwise to a suspension of Intermediate 38 (5.2 g, 14 mmol) in toluene (150 mL). The reaction was then heated at reflux for 3 h before allowing the reaction to cool to room temperature. The solvent and residual thionyl chloride were removed in vacuo and the resultant solid co-evaporated with toluene (×3). This gave the title compound as an orange solid (4.9 g) and was used without further purification. NMR δH (CDCl$_3$) 7.77 (1H, d, J 9.7 Hz), 7.29 (4H, m), 6.68 (2H, d, J 9.7 Hz).

Intermediate 69

3-Bromo-7-(4-fluorophenyl)-2-{[(3R)-3-hydroxypyrrolidin-1-yl]carbonyl}thieno[2,3-b]pyridin-6(7H)-one To a solution of Intermediate 68 (2.5 g, 6.5 mmol) and diisopropylethylamine (1.7 mL, 9.7 mmol) in DCM (100 mL) was added (R)-3-hydroxypyrrolidine (850 mg, 9.7 mmol) and the reaction stirred at r.t. for 18 h. The reaction mixture was washed with water and brine, the DCM layer separated, dried (MgSO$_4$) and then concentrated in vacuo to give the title compound as an orange solid (2.65 g). LCMS RT 2.67 minutes, 439 (M+H)+.

Intermediate 70

3-Bromo-7-(4-fluorophenyl)-2-{[(3S)-3-hydroxypyrrolidin-1-yl]carbonyl}thieno[2,3-b]pyridin-6(7H)-one To a solution of Intermediate 68 (2.5 g, 6.5 mmol) and diisopropylethylamine (1.7 mL, 9.7 mmol) in DCM (10 mL) was added (S)-3-hydroxypyrrolidine (850 mg, 9.7 mmol) and the reaction stirred at r.t. for 18 h. The reaction mixture was washed with water and brine, the DCM layer separated, dried (MgSO$_4$) and then concentrated in vacuo to give the title compound as an orange solid (2.84 g). LCMS RT 2.67 minutes, 439 (M+H)+.

Intermediate 71

3-Bromo-7-(4-fluorophenyl)-2-{[(3R)-3-(tetrahydro-2H-pyran-2-yloxy)pyrrolidin-1-yl]carbonyl}thieno[2,3-b]pyridin-6(7H)-one To a solution of Intermediate 69 (2.65 g, 6.0 mmol) in DCM (80 mL) was added p-toluenesulphonic acid (10 mg, 0.06 mmol) and 3,4-dihydro-2H-pyran (2.8 mL, 30 mmol) and the reaction stirred at r.t. for 3 h. The reaction mixture was washed with sat. NaHCO$_3$(aq) (×2), then brine, dried (MgSO$_4$) and concentrated in vacuo. The crude product was purified by column chromatography (silica, 80% EtOAc in isohexane) to give the title compound as a white solid (2.40 g). LCMS RT 3.28 minutes, 523 (M+H)+.

Intermediate 72

3-Bromo-7-(4-fluorophenyl)-2-{[(3S)-3-(tetrahydro-2H-pyran-2-yloxy)pyrrolidin-1-yl]carbonyl}thieno[2,3-b]pyridin-6(7H)-one To a solution of Intermediate 70 (2.65 g, 6.0 mmol) in DCM (80 mL) was added p-toluenesulphonic acid (10 mg, 0.06 mmol) and 3,4-dihydro-2H-pyran (2.8 mL, 30 mmol) and the reaction stirred at r.t. for 3 h. The reaction mixture was washed with sat. NaHCO$_3$(aq) (×2), then brine, dried (MgSO$_4$) and concentrated in vacuo. The crude product was purified by column chromatography (silica, 80% EtOAc in isohexane) to give the title compound as a white solid (2.74 g). LCMS RT 3.28 minutes, 523 (M+H)+.

Intermediate 73

3-[(2,4-Difluorophenyl)amino]-7-(4-fluorophenyl)-2{[(3R)-3-(tetrahydro-2H-pyran-2-yloxy)pyrrolidin-1-yl]carbonyl}thieno[2,3-b]pyridin-6(7H)-one To a de-gassed solution of Intermediate 71 (1.2 g, 2.30 mmol), tris(dibenzylideneacetone)dipalladium(0) (210 mg, 0.23 mmol) and (+/−)-BINAP (290 mg, 0.46 mmol) in toluene (15 mL) was added 2,4-difluoroaniline (281 µL, 2.76 mmol) and caesium carbonate (1.0 g, 3.22 mmol). The reaction was heated at 110° C. under nitrogen for two days. The reaction mixture was diluted with EtOAc (80 mL), washed with water, brine (×2), dried (MgSO$_4$) and concentrated in vacuo. The crude product was purified by column chromatography (silica, 50% EtOAc in isohexane) to give the title compound as a brown solid (876 mg). LCMS RT 3.76 minutes, 570 (M+H)+.

Intermediate 74

3-[(2,4-Difluorophenyl)amino]-7-(4-fluorophenyl)-2{[(3S)-3-(tetrahydro-2H-pyran-2-yloxy)pyrrolidin-1-yl]carbonyl}thieno[2,3-b]pyridin-6(7H)-one To a de-gassed solution of Intermediate 72 (1.37 g, 2.63 mmol), tris(dibenzylideneacetone)dipalladium(0) (120 mg, 0.13 mmol) and (+/−)-BINAP (160 mg, 0.26 mmol) in toluene (15 mL) was added 2,4-difluoroaniline (321 µL, 3.16 mmol) and caesium carbonate (1.20 g, 3.68 mmol). The reaction was heated at 110° C. under nitrogen for 18 h. Additional equivalents of Pd$_2$(dba)$_3$ (60 mg, 0.065 mmol) and (+/−)-BINAP (80 mg, 0.13 mmol) were added and the reaction heated at reflux for a further 2 days. The reaction mixture was diluted with EtOAc (80 mL), washed with water, brine (×2), dried (MgSO$_4$) and concentrated in vacuo. The crude product was purified by column chromatography (silica, 50% EtOAc in isohexane) to give the title compound as a brown solid (767 mg). LCMS RT 3.74 minutes, 570 (M+H)+.

Intermediate 75

3-[(4-Fluoro-3-methylphenyl)amino]-7-(4-fluorophenyl)-2-{[(3S)-3-(tetrahydro-2H-pyran-2-yloxy) pyrrolidin-1-yl]carbonyl}thieno[2,3-b]pyridin-6(7H)-one To a de-gassed solution of Intermediate 72 (1.37 g, 2.63 mmol), tris(dibenzylideneacetone)dipalladium(0) (120 mg, 0.13 mmol) and (+/−-BINAP (160 mg, 0.26 mmol) in toluene (15 mL) was added 4-fluoro-3-methylaniline (400 mg, 3.16 mmol) and caesium carbonate (1.20 g, 3.68 mmol). The reaction was heated at 110° C. under nitrogen for 18 h. Additional equivalents of $Pd_2(dba)_3$ (60 mg, 0.065 mmol) and (+/−)-BINAP (80 mg, 0.13 mmol) were added and the reaction heated at reflux for a further 2 days. The reaction mixture was diluted with EtOAc (80 mL), washed with water, brine (×2), dried ($MgSO_4$) and concentrated in vacuo. The crude product was purified by column chromatography (silica, 50% EtOAc in isohexane) to give the title compound as a brown solid (980 mg). LCMS RT 3.84 minutes, 566 $(M+H)^+$.

Intermediate 76

3-Bromo-7-(2-chlorophenyl)-2-{[(3S)-3-hydroxy-pyrrolidin-1-yl]carbonyl}thieno[2,3-b]pyridin-6(7H)-one The title compound was prepared from Intermediate 55 and (S)-3-hydroxypyrrolidine following the method of Intermediate 56.

Intermediate 77

3-Bromo-7-(2-chlorophenyl)-2-{[(3S)-3-(tetrahydro-2H-pyran-2-yloxy)pyrrolidin-1-yl]carbonyl}thieno[2,3-b]pyridin-6(7H)-one The title compound was prepared from Intermediate 76 and 3,4-dihydro-2H-pyran following the method of Intermediate 57. NMR δH ($CDCl_3$) 7.77 (1H, d, J 9.6 Hz), 7.66-7.61 (1H, m), 7.54-7.41 (3H, m), 6.73 (1H, d, J 9.6 Hz), 4.69-4.53 (1H, m), 4.45-4.43 (1H, m), 3.86-3.49 (6H, m), 2.17-2.14 (2H, m), 1.87-1.69 (2H, m), 1.55-1.40 (4H, m). LCMS $(ES^+)$ RT 3.45 minutes, 539 $(M+H)^+$.

Intermediate 78

7-(2-Chlorophenyl)-3-[(4-fluoro-3-methylphenyl)amino]-2-{[(3S)-3-(tetrahydro-2H-pyran-2-yloxy)pyrrolidin-1-yl]carbonyl}thieno[2,3-b]pyridin-6(7H)-one The title compound was prepared from Intermediate 77 (883 mg, 1.64 mmol) and 4-fluoro-3-methylaniline (267 mg, 2.13 mmol) following the method of Intermediate 75. The crude product was purified by column chromatography (silica, 10% EtOAc in DCM) to give the title compound as a yellow solid (623 mg). NMR δH ($CDCl_3$) 9.70 (1H, s), 7.68-7.64 (1H, m), 7.55-7.41 (3H, m), 7.27-7.24 (1H, m), 6.96-6.85 (3H, m), 6.37 (1H, d, J 9.8 Hz), 4.65-4.63 (1H, m), 4.42-4.40 (1H, m), 3.84-3.64 (5H, m), 3.51-3.47 (1H, m), 2.24 (3H, s), 2.16-2.01 (1H, m), 1.99-1.92 (1H, m), 1.80-1.70 (1H, m), 1.68-1.67 (1H, m), 1.56-1.49 (4H, m). LCMS $(ES^+)$ RT 3.94 minutes, 582 $(M+H)^+$.

Intermediate 79

7-(2-Chlorophenyl)-3-[(3-methylphenyl)amino]-2-{[(3S)-3-(tetrahydro-2H-pyran-2-yloxy)pyrrolidin-1-yl]carbonyl}thieno[2,3-b]pyridin-6(7H)-one The title compound was prepared from Intermediate 77 (883 mg, 1.64 mmol) and m-toluidine (0.28 mL, 2.62 mmol) following the method of Intermediate 75. The crude product was purified by column chromatography (silica, 10% EtOAc in DCM) to give the title compound as a pale yellow solid (509 mg). NMR δH ($CDCl_3$) 9.65 (1H, m), 7.68-7.65 (3H, m), 7.39 (1H, d, J 9.7 Hz), 7.11 (1H, t, J 7.5 Hz), 6.90-6.84 (3H, m), 6.40 (1H, d, J 9.8 Hz), 4.63-4.60 (1H, m), 4.40-4.38 (1H, m), 3.81-3.67 (5H, m), 3.65-3.63 (1H, m), 2.31 (3H, s), 2.17-1.57 (5H, m), 1.53 (3H, s). LCMS $(ES^+)$ RT 3.91 minutes, 564 $(M+H)^+$.

Intermediate 80

7-(2-Chlorophenyl)-3-[(2,4-difluorophenyl)amino]-2-{[(3S)-3-(tetrahydro-2H-pyran-2-yloxy)pyrrolidin-1-yl]carbonyl}thieno[2,3-b]pyridin-6(7H)-one The title compound was prepared from Intermediate 77 (883 mg, 1.64 mmol) and 2,4-difluoroaniline (0.28 mL, 2.75 mmol) following the method of Intermediate 75. The crude product was purified by column chromatography (silica, 10% EtOAc in DCM) to give the title compound as a brown solid (750 mg). NMR δH ($CDCl_3$) 9.66 (1H, d, J 4.4 Hz), 7.68-7.64 (1H, m), 7.56-7.41 (3H, m), 7.27 (1H, d, J 8.8 Hz), 7.07-7.04 (1H, m), 6.94-6.89 (1H, m), 6.84-6.80 (1H, m), 6.42 (1H, d, J 9.7 Hz), 4.65-4.63 (1H, m), 4.40-4.38 (1H, m), 3.86-3.61 (5H, m), 3.51-3.44 (1H, m), 2.07-1.89 (2H, m), 1.79-1.77 (1H, m), 1.71-1.68 (1H, m), 1.59-1.49 (4H, m). LCMS $(ES^+)$ RT 3.83 minutes, 586 $(M+H)^+$.

Intermediate 81

3-Bromo-7-(4-methylphenyl)-2-{[(3S)-3-hydroxy-pyrrolidin-1-yl]carbonyl}thieno[2,3-b]pyridin-6(7H)-one The title compound was prepared from Intermediate 37 and (S)-3-hydroxypyrrolidine following the method of Intermediate 56. NMR δH ($CDCl_3$) 7.66 (1H, d, J 9.6 Hz), 7.30 (2H, d, J 8.1 Hz), 7.18 (2H, d, J 8.1 Hz), 6.65 (1H, d, J 9.6 Hz), 4.44 (1H, bm), 3.80-3.25 (4H, m), 2.37 (3H, s), 2.20-1.93 (3H, m). LCMS $(ES^+)$ RT 2.65 minutes, 433 $(M+H, ^{79}Br)^+$, 435 $(M+H, ^{81}Br)^+$.

Intermediate 82

3-Bromo-7-(4-methylphenyl)-2-{[(3R)-3-hydroxy-pyrrolidin-1-yl]carbonyl}thieno[2,3-b]pyridin-6(7H)-one The title compound was prepared from Intermediate 37 (6.0 g, 18.0 mmol) and (R)-3-hydroxypyrrolidine (2.0 g, 27.0 mmol) following the method of Intermediate 56. The crude product was purified by column chromatography (silica, 20% THF in DCM) to give the title compound as a white solid (5.36 g). δH 7.68 (1H, d, J 9.6 Hz), 7.32 (2H, m), 7.20 (2H, m), 6.66 (1H, d, J 9.6 Hz), 4.49 (1H, bs), 3.78-3.60 (3H, m), 2.39 (3H, s), 1.97 (2H, bs), 1.82 (2H, bs). LCMS $(ES^+)$ RT 2.64 minutes, 433 $(M+H, ^{79}Br)^+$, 435 $(M+H, ^{81}Br)^+$.

Intermediate 83

3-Bromo-7-phenyl-2-[(3-hydroxyazetidin-1-yl)carbonyl]-7H-thieno[2,3-b]pyridin-6-one Intermediate 36 (17.6 g, 50 mmol) was suspended in DCM (150 mL) to which thionyl chloride (30 mL, 411 mmol) and DMF (0.5 mL) were added. The mixture was heated under reflux for 1 h during which the solid dissolved to form a dark solution. After cooling to ambient temperature, the solution was evaporated to dryness in vacuo (30° C./150 mBar). This step was repeated twice with fresh DCM (2×100 mL). The intermediate acid chloride was thus obtained as a mottled brown solid.

In a separate flask, 3-hydroxyazetidine hydrochloride (10.9 g, 100 mmol) and diisopropylethylamine (50 mL, 360 mmol) were stirred at 20-25° C. in 1:1 DCM:DMF (400 mL) for 1 h then cooled to 0-5° C. A solution of the acid chloride (19.9 g) in DCM (200 mL) was added to this preparation over 1 h and the resulting orange-brown solution stirred out for another hour. Following evaporation to dryness (5-100 mBar/ 40° C.), the residue was partitioned between EtOAc (500 mL) and water (150 mL) at 40° C. The organic phase was washed twice with water (2×100 mL) then re-evaporated. The residue was re-suspended in fresh EtOAc (200 mL) at 40° C. and then filtered. The title compound was obtained as a fawn powder after washing with EtOAc (3×30 mL) and drying in vacuo at 50° C. (16.5 g, 81.5% yield, m.p. 199.1° C.). δH (DMSO-d6) 7.87 (1H, d, J 9.8 Hz), 7.65 (3H, m), 7.55 (2H, m), 6.69 (1H, d, J 9.8 Hz), 5.62 (1H, d, J 6.5 Hz), 4.46 (1H, m), 4.30 (2H, m), 3.87 (2H, br m). LCMS (ES$^+$) RT 2.19 minutes, 405 (M+H)$^+$.

Intermediate 84

3-Bromo-7-phenyl-2-[3-(tetrahydropyran-2-yloxy)-azetidine-1-carbonyl]-7H-thieno[2,3-b]pyridin-6-one p-Toluenesulfonic acid monohydrate (0.28 g, 1.47 mmol) was added to a suspension of Intermediate 83 (11.9 g, 29 mmol) in DCM (100 mL) containing 3,4-dihydro-2H-pyran (7.5 g, 89 mmol). The mixture was stirred until all the starting material had dissolved to give an orange solution and then left to stand at 20-25° C. overnight. Sat. NaHCO$_3$(aq) (20 mL) was added to quench the reaction and the organic phase washed subsequently with water (25 mL). After drying (Na$_2$SO$_4$) and removal of solvent in vacuo the crude product was obtained as a brown glass (22.8 g). This residue was taken up in EtOAc (100 mL) at 40° C., and then seeded after the resulting solution had cooled to 25° C. Once crystallisation had initiated the temperature was reduced further to 0-5° C. and the slurry stirred out for 1 h. The fawn solid was filtered off, washed with EtOAc (2×25 mL) and dried at 40° C. in vacuo, affording the title compound (14.1 g, 71.2% yield, m.p. 162° C.). δH (CDCl$_3$) 7.78 (1H, d, J 9.8 Hz), 7.67 (3H, m), 7.48 (2H, m), 6.73 (1H, d, J 9.8 Hz), 4.70 (1H, m), 4.68 (1H, m), 4.40 (2H, dd), 4.19 (2H, m), 3.81 (1H, m), 3.50 (1H, m), 1.42-1.90 (6H, br m). LCMS (ES$^+$) RT 3.31 minutes, 489 (M+H)$^+$.

Intermediate 85

3-(4-Fluoro-3-methylphenylamino)-7-phenyl-2-[3-(tetrahydropyan-2-yloxy)azetidine-1-carbonyl]-7H-thieno[2,3-b]pyridin-6-one Intermediate 84 (2.00 g, 4.21 mmol), 4-fluoro-3-methylaniline (0.58 g, 4.64 mmol), rac-BINAP (0.26 g, 0.42 mmol), Pd$_2$(dba)$_3$ (0.19 g, 0.21 mmol) cesium carbonate (2.01 g, 6.17 mmol) and toluene (20 mL) were charged to an oven-dried flask and heated to reflux for 2 h under an atmosphere of nitrogen. After cooling to r.t. water (20 mL) was added and this mixture stirred for 10 min. At this time the solid was isolated via filtration, washed with toluene (2×5 mL) and water (2×5 mL) and dried in vacuo to yield the title compound (1.89 g, 84%). δH (CDCl$_3$) 9.62 (1H, s), 7.53-7.64 (3H, m), 7.38-7.41 (2H, m), 7.16-7.20 (1H, d), 6.87-6.98 (3H, m), 6.36-6.39 (1H, d), 4.51-4.60 (2H, m), 4.32-4.49 (2H, m), 4.04-4.16 (2H, m), 3.78-3.85 (1H, m), 3.47-3.51 (1H, m), 2.25 (3H, s), 1.51-1.81 (6H, m). LCMS (ES$^+$), RT 4.19 minutes, 534 (M+H)$^+$.

Intermediate 86 tert-Butyl [1-({3-[(2,4-difluorophenyl)amino]-6-oxo-7-phenyl-6,7-dihydrothieno[2,3-b]pyridin-2-yl}carbonyl)piperidin-4-yl]carbamate A mixture of Intermediate 35 (800 mg, 1.42 mmol), Et$_3$N (0.5 mL) and tert-butyl piperidin-4-ylcarbamate (354 mg, 1.70 mmol) in DCM (20 mL) was stirred at r.t for 18 h. The reaction was concentrated under vacuum and triturated with Et$_2$O. Purification by chromatography (silica, 2% EtOAc in DCM) gave the title compound as an off-white solid (267 mg, 32%). δH (DMSO-d6) 8.40 (1H, s), 7.87 (1H, d, J 9.6 Hz), 7.7-7.6 (3H, m), 7.57-7.53 (2H, m), 7.33-7.26 (1H, m), 6.98-6.9 (2H, m), 6.86-6.83 (1H, m), 6.57 (1H, d, J 9.6 Hz), 3.85-3.80 (2H, m), 3.40-3.30 (1H, m), 2.55-2.50 (2H, m), 1.65-1.60 (2H, m), 1.38 (9H, s), 1.18-1.14 (2H, m). LCMS (ES$^+$) RT 3.50 minutes, 581 (M+H)$^+$.

Intermediate 87 tert-Butyl [1-({3-[(2,4-difluorophenyl)amino]-6-oxo-7-phenyl-6,7-dihydrothieno[2,3-b]pyridin-2-yl}carbonyl)azetidin-3-yl]carbamate A mixture of Intermediate 35 (483 mg, 0.85 mmol), Et$_3$N (0.5 mL) and tert-butyl azetidin-3-ylcarbamate (175 mg, 1.02 mmol) in DCM (20 mL) was stirred at r.t. for 18 h. The reaction mixture was concentrated under vacuum and triturated with Et$_2$O. The title compound was obtained as a yellow solid (386 mg, 82%). δH (DMSO-d6) 9.32 (1H, s), 7.71-7.62 (3H, m), 7.57-7.50 (2H, m), 7.45-7.38 (1H, m), 7.36 (1H, d, J 9.7 Hz), 7.17-7.10 (1H, m), 7.09-7.00 (1H, m), 6.47 (1H, d, J 9.7 Hz), 4.60-4.30 (3H, m), 3.90-3.80 (2H, m), 3.35-3.30 (1H, m), 1.40 (9H, s). LCMS (ES$^+$) RT 3.58 minutes, 553 (M+H)$^+$.

Intermediate 88

3-Bromo-7-(2-chlorophenyl)-2-{[(3R)-3-hydroxypyrrolidin-1-yl]carbonyl}thieno[2,3-b]pyridin-6(7H)-one From Intermediate 55 (4.7 g, 12.2 mmol) and (R)-3-hydroxypyrrolidine (1.13 g, 13 mmol) by the method of Intermediate 56 to give the title compound as a yellow solid (5.70 g, quant). δH (CDCl$_3$) 7.77 (1H, d, J 9.6 Hz), 7.63-7.60 (1H, m), 7.51-7.37 (3H, m), 6.70 (1H, d, J 9.6 Hz), 4.51 (1H, br m), 3.78-3.53 (4H, m), 2.20-1.70 (2H, m), 1.60 (1H, br s). LCMS (ES$^+$) RT 2.70 minutes, 453 (M+H)$^+$.

Intermediate 89

3-Bromo-7-(2-chlorophenyl)-2-{[(3R)-3-(tetrahydro-2H-pyran-2-yloxy)pyrrolidin-1-yl]carbonyl}thieno[2,3-b]pyridin-6(7H)-one From Intermediate 88 (5.35 g, 11.8 mmol) and 3,4-dihydro-2H-pyran (3.3 mL, 35.4 mmol) by the method of Intermediate 57 to give the title compound as an orange solid (6.70 g, quant). δH (DMSO-d6) 7.91-7.60 (5H, m), 6.70 (1H, d, J 9.6 Hz), 4.85-4.83 (1H, m), 4.78-4.67 (1H, m), 4.34-4.27 (1H, m), 3.93-3.40 (5H, m), 2.10-1.95 (2H, m), 1.85-1.40 (6H, m). LCMS (ES$^+$) RT 3.46 minutes, 537 (M+H)$^+$.

Intermediate 90

7-(2-Chlorophenyl)-3-[(2,4-difluorophenyl)amino]-2-{[(3R)-3-(tetrahydro-2H-pyran-2-yloxy)pyrrolidin-1-yl]carbonyl}thieno[2,3-b]pyridin-6(7H)-one From Intermediate 89 (6.35 g, 11.8 mmol) and 2,4-difluoroaniline (1.45 mL, 14.1 mmol) by the method of Intermediate 75 to give the title compound as a pale brown solid (3.0 g, 43%). δH (DMSO-d6) 8.99-8.94 (1H, m), 7.83-7.79 (1H, m), 7.74-7.59 (4H, m), 7.39-7.26 (1H, m), 7.06-6.93 (2H, m), 6.51 (1H, d, J 9.7 Hz), 4.62-4.54 (1H, m), 4.23-4.18 (1H, m), 3.73-3.50 (6H, m), 1.95-1.35 (8H, m). LCMS (ES$^+$) RT 3.85 minutes, 586 (M+H)$^+$.

EXAMPLE 1

3-[(2,4-Difluorophenyl)amino]-2-{[(2R)-2-(hydroxymethyl)pyrrolidin-1-yl]carbonyl}-7-phenylthieno[2,3-b]pyridin-6(7H)-one To a suspension of Intermediate 45 (7.3 g, 12.9 mmol) in ethanol (300 mL) was added 10% HCl(aq) (40 mL) and the reaction stirred at room temperature for 16 h. The reaction mixture was then concentrated in vacuo to give an orange/brown oil. The crude product was purified by column chromatography (silica, EtOAc) followed by a second column (silica, 10% THF in DCM) to give the title compound as a light yellow solid (4.05 g). δH (CDCl$_3$) 9.36 (1H, bs), 7.68-7.36 (3H, m), 7.33-7.18 (2H, m), 7.14-7.06 (1H, m), 7.04-7.00 (1H, m), 6.97-6.73 (2H, m), 6.35 (1H, d, J 9.7 Hz), 4.36-4.28 (1H, m), 3.74-3.47 (4H, m), 2.00-1.68 (3H, m), 1.60-1.50 (1H, m). LCMS (ES$^+$) RT 3.19 minutes, 482 (M+H)$^+$.

EXAMPLE 2

2-{[(2R)-2-(Hydroxymethyl)pyrrolidin-1-yl]carbonyl}-3-[(3-methylphenyl)amino]-7-phenylthieno[2,3-b]pyridin-6(7H)-one The title compound was prepared from Intermediate 46 (2.0 g, 3.68 mmol) following the method of Example 1 to give the title compound as a pale yellow solid (747 mg). δH (CDCl$_3$) 7.77 (3H, m), 7.71 (2H, m), 7.51 (H, d, J 9.73 Hz), 7.36 (1H, m), 7.07 (3H, m), 6.58 (1H, d, J 9.75 Hz), 4.57 (1H, m), 4.00-3.75 (4H, m), 2.51 (3H, s), 2.25-2.00 (3H, m), 1.81 (1H, m). LCMS (ES$^+$) RT 3.18 minutes, 460 (M+H)$^+$.

EXAMPLE 3

3-[(3-Chlorophenyl)amino]-2-{[(2R)-2-(hydroxymethyl)pyrrolidin-1-yl]carbonyl}-7-phenylthieno[2,3-b]pyridin-6(7H)-one The title compound was prepared from intermediate 47 (0.85 g, 11.5 mmol) following the method of Example 1 to give the title compound as a pale yellow solid (545 mg). δH (CDCl$_3$) 7.60 (3H, m), 7.55 (3H, m), 7.37 (1H, m), 7.03 (2H, m), 6.95 (1H, m), 6.49 (H, d, J 9.7 Hz), 4.38 (1H, m), 3.80 (1H, m) 3.76 (1H, m), 3.62 (2H, m), 2.18 (1H, s), 1.96 (3H, m), 1.66 (1H, m). LCMS (ES$^+$) RT 3.15 minutes, 480 (M+H)$^+$.

EXAMPLE 4

3-[(2,4-Difluorophenyl)amino]-2-{[(2R)-2-(hydroxymethyl)pyrrolidin-1-yl]carbonyl}-7-(4-methylphenyl)thieno[2,3-b]pyridin-6(7H)-one The title compound was prepared from Intermediate 48 (1.14 g, 2.0 mmol) following the method of Example 1 to give the title compound as a pale yellow solid (470 mg, 46%). δH (CDCl$_3$) 7.31-7.29 (2H, m), 7.19-7.13 (3H, m), 6.95-6.84 (1H, m), 6.83-6.80 (1H, m), 6.74 (1H, t, J 7.7 Hz), 6.34 (1H d, J 9.7 Hz), 4.31-4.25 (1H, m), 3.72-3.48 (4H, m), 2.37 (3H, s), 1.96-1.73 (3H, m), 1.62-1.51 (1H, m). LCMS (ES$^+$) RT 3.24 minutes, 496 (M+H)$^+$.

EXAMPLE 5

3-[(4-Fluoro-3-methylphenyl)amino]-2-{[(2R)-2-(hydroxymethyl)-pyrrolidin-1-yl]carbonyl}-7-(4-methylphenyl)thieno[2,3-b]pyridin-6(7H)-one The title compound was prepared from Intermediate 49 (879 mg, 1.52 mmol) following the method of Example 1 to give the title compound as a pale yellow solid (410 mg, 54%). δH (CDCl$_3$) 9.35 (1H, bs), 7.30 (2H, m), 7.21-7.12 (3H, m), 6.86-6.75 (3H, m), 6.29 (1H, d, J 9.7 Hz), 4.30-4.25 (2H, m), 3.72-3.70 (1H, m), 3.69-3.63 (1H, m), 3.62-3.49 (2H, m), 2.174 (3H, s), 2.170 (3H, s), 1.96-1.74 (3H, m), 1.58-1.50 (1H, m). LCMS (ES$^+$) RT 3.30 minutes, 492 (m+H)$^+$.

EXAMPLE 6

2-{[(2R)-2-(Hydroxymethyl)pyrrolidin-1-yl]carbonyl}-7-(4-methylphenyl)-3-[(3-methylphenyl)amino]thieno[2,3-b]pyridin-6(7H)-one The title compound was prepared from Intermediate 50 (1.0 g, 1.8 mmol) following the method of Example 1 to give the title compound as a yellow solid (492 mg, 56%). δH (CDCl$_3$) 9.20 (1H, bs), 7.31-7.18 (5H, m), 7.09 (1H, t, J 8.0 Hz), 6.80-6.75 (3H, m), 6.30 (1H, d, J 9.6 Hz), 4.29-4.19 (2H, m), 3.71-3.67 (1H, m), 3.65-3.59 (1H, m), 3.52-3.46 (2H, m), 2.37 (3H, s), 2.23 (3H, s), 1.96-1.73 (3H, m), 1.69-1.56 (1H, m). LCMS (ES$^+$) RT 3.27 minutes, 474 (M+H)$^+$.

EXAMPLE 7

3-[(2,4-Difluorophenyl)amino]-7-(4-fluorophenyl)-2-{[(2R)-2-(hydroxymethyl)pyrrolidin-1-yl]carbonyl}thieno[2,3-b]pyridin-6(7H)-one The title compound was prepared from Intermediate 51 (206 mg, 0.35 mmol) following the method of Example 1 to give the title compound as an off-white solid (155 mg). δH (DMSO-d6) 8.92 (1H, s), 7.92 (1H, d, J 9.6 Hz), 7.79 (2H, m), 7.66 (2H, t, J 8.6 Hz), 7.51-7.46 (1H, m), 7.20-7.10 (2H, m), 6.68 (1H d, J 9.6 Hz), 4.82 (1H, m), 4.10 (1H, bs), 3.54 (1H, m), 3.44 (1H, m), 3.11 (1H, m), 1.98-1.87 (3H, m), 1.80 (1H, m). LCMS (ES$^+$) RT 3.15 minutes, 500 (M+H)$^+$.

EXAMPLE 8

3-[(4-Fluoro-3-methylphenyl)amino]-7-(4-fluorophenyl)-2-{[(2R)-2-(hydroxymethyl)pyrrolidin-1-yl]carbonyl}thieno[2,3-b]pyridin-6(7H)-one The title compound was prepared from Intermediate 52 (90 mg, 0.16 mmol) following the method of Example 1 to give the title compound as a pale yellow solid (63 mg). δH (DMSO-d6) 8.80 (1H, s), 7.81 (1H, d, J 9.6 Hz), 7.66 (2H, m), 7.52 (2H, t, J 8.5 Hz), 7.05 (1H, t, J 9.1 Hz), 6.87-6.85 (1H, m), 6.82-6.78 (1H, m), 6.56 (1H, d, J 9.6 Hz), 4.67 (1H, t, J 5.5 Hz), 3.96 (1H, m), 3.36-3.32 (2H, m), 2.87 (1H, m), 2.20 (3H, s), 1.72-1.69 (3H, m), 1.63-1.58 (1H, m). LCMS (ES$^+$) RT 3.22 minutes, 496 (M+H)$^+$.

EXAMPLE 9

7-(2-Chlorophenyl)-3-[(4-fluoro-3-methylphenyl) amino]-2-{[(2R)-2-(hydroxymethyl)pyrrolidin-1-yl] carbonyl}thieno[2,3-b]pyridin-6(7H)-one 1M HCl aq (2 mL) was added to a solution of Intermediate 58 (500 mg, 0.84 mmol) in EtOH (20 mL) and the mixture stirred at r.t. overnight. Saturated Na$_2$CO$_3$ aq (50 mL) was added and the mixture extracted with EtOAc (50 ml then 10 mL). The combined organics were dried (Na$_2$SO$_4$) and concentrated in vacuo. The residual gum was treated with DCM (5 mL) and then the solvent removed in vacuo to give the title compound as a yellow solid (400 mg, 93%). δH (CDCl$_3$) 9.47 (1H, br d, J 7.7 Hz), 7.60-7.56 (1H, m), 7.49-7.33 (3H, m), 7.18 (1H, dd, J 0.5, 9.8 Hz), 6.89-6.79 (3H, m), 6.30 (1H, dd, J 0.5, 9.8 Hz), 4.33-4.31 (1H, m), 4.29 (1H, br s), 3.74-3.37 (4H, m), 2.19 (3H, d, J 1.5 Hz), 1.99-1.64 (4H, m). LCMS (ES$^+$) RT 3.28 minutes, 512 (M+H)$^+$.

EXAMPLE 10

7-(2-Chlorophenyl)-3-[(2,4-difluorophenyl)amino]-2-{[(2R)-2-(hydroxymethyl)pyrrolidin-1-yl] carbonyl}thieno[2,3-b]pyridin-6(7H)-one From Intermediate 59 by the method of Example 9. Brown solid. δH (CDCl$_3$) 9.40 (1H, s), 7.65-7.62 (1H, m), 7.53-7.39 (3H, m), 7.24 (1H, d, J 9.9 Hz), 7.10-7.04 (1H, m), 6.84-6.80 (1H, m), 6.41 (1H, d, J 9.8 Hz), 4.40-4.34 (1H, m), 4.17-4.18 (1H, m), 3.79-3.54 (4H, m), 1.98-1.75 (3H, m), 1.55-1.50 (1H, m). LCMS (ES$^+$) RT 3.247 minutes, 516 (M+H)$^+$.

EXAMPLE 11

3-[(2-Chlorophenyl)amino]-2-{[(2R)-2-(hydroxymethyl)pyrrolidin-1-yl]carbonyl}-7-phenylthieno[2,3-b]pyridin-6(7H)-one To a suspension of Intermediate 63 (1.0 g, 2.4 mmol) in DCM (15 mL) was added EDC (0.73 g, 3.7 mmol, 1.5 equiv.), HOBT (0.33 g, 3.7 mmol, 1.5 equiv.) and the mixture stirred at r.t. for 15 minutes. (R)-2-Pyrrolidinemethanol (0.25 mL, 3.7 mmol) was added and the reaction stirred at r.t. for 18 h. The reaction was diluted with DCM (10 mL), washed with water (10 mL) and brine (10 mL), dried (MgSO$_4$) and concentrated in vacuo. The crude residue was purified by column chromatography (silica, 20% EtOAc in DCM) to give the title compound as an off-white solid (492 mg). δH (DMSO-d6) 9.00 (1H, bs), 7.77-7.68 (7H, m), 7.38 (1H, m), 7.07 (2H, m), 6.64 (1H, d, J 9.6 Hz), 4.78 (1H, t, J 5.9 Hz), 4.22-4.15 (1H, m), 3.55-3.53 (2H, m), 3.46-3.39 (1H, m), 3.26-3.18 (1H, m), 1.99-1.77 (4H, m). LCMS (ES$^+$) RT 3.28 minutes, (Cl$^{37}$) 482 (M+H)$^+$.

General Procedure for Preparing Amide Examples by EDC Coupling

The following Examples were all prepared from the appropriate carboxylic acid intermediate and amine starting materials following the method described for Example 11.

EXAMPLE 12

3-[(2-Chlorophenyl)amino]-2-{[(2S)-2-(hydroxymethyl)pyrrolidin-1-yl]carbonyl}-7-phenylthieno[2,3-b]pyridin-6(7H)-one The title compound was prepared from Intermediate 63 (500 mg, 1.24 mmol) and (S)-2-pyrrolidinemethanol (0.12 mL, 1.86 mmol) following the method of Example 11 to give the title compound as an off-white solid (40 mg). δH (CDCl$_3$) 7.57-7.42 (3H, m), 7.39-7.29 (4H, m), 7.14-7.05 (1H, m), 6.95-6.84 (2H, m), 6.39 (1H, d, J 9.7 Hz), 4.32-4.24 (1H, m), 3.70-3.58 (2H, m), 3.52-3.38 (2H, m), 1.97-1.49 (4H, m). LCMS (ES$^+$) RT 3.27 minutes, (Cl$^{37}$) 482 (M+H)$^+$.

EXAMPLE 13

3-Anilino-2-{[(2R)-2-(hydroxymethyl)pyrrolidin-1-yl]carbonyl}-7-phenylthieno[2,3-b]pyridin-6(7H)-one The title compound was prepared from Intermediate 29 and (R)-2-pyrrolidinemethanol following the method of Example 11 to give the title compound as a pale yellow solid. δH (CDCl$_3$) 7.56-7.47 (3H, m), 7.36-7.33 (2H, m), 7.27-7.19 (3H, m), 7.02-6.99 (3H, m), 6.34 (1H, d, J 9.7 Hz), 4.34-4.29 (1H, m), 3.73-3.69 (1H, m), 3.65-3.62 (1H, m), 3.57-3.48 (2H, m), 2.06-1.70 (3H, m), 1.60-1.45 (2H, m). LCMS (ES$^+$) RT 3.10 minutes, 446 (M+H)$^+$.

EXAMPLE 14

3-Anilino-2-{[(2S)-2-(hydroxymethyl)pyrrolidin-1-yl]carbonyl}-7-phenylthieno[2,3-b]pyridin-6(7H)-one The title compound was prepared from Intermediate 29 and (R)-2-pyrrolidinemethanol following the method of Example 11 to give the title compound as a pale yellow solid. δH (CDCl$_3$) 9.31 (1H, bs), 7.55-7.46 (3H, m), 7.35-7.32 (2H, m), 7.26-7.18 (3H, m), 7.01-6.98 (3H, m), 6.33 (1H, d, J 9.7 Hz), 4.32-4.29 (1H, m), 4.14 (1H, bs), 3.73-3.64 (2H, m), 3.61-3.50 (2H, m), 1.97-1.71 (3H, m), 1.58-1.50 (1H, m). LCMS (ES$^+$) RT 3.11 minutes, 446 (M+H)$^+$.

EXAMPLE 15

3-[(2,4-Difluorophenyl)amino]-2-{[(2S)-2-(hydroxymethyl)pyrrolidin-1-yl]carbonyl}-7-phenylthieno[2,3-b]pyridin-6(7H)-one The title compound was prepared from Intermediate 28 (1.0 g, 2.58 mmol) and (S)-2-pyrrolidinemethanol (390 mg, 3.87 mmol) following the method of Example 11 to give the title compound as a pale yellow solid (300 mg). δH (CDCl$_3$) 7.65-7.48 (3H, m), 7.35-7.32 (2H, m), 7.15 (1H, d, J 9.7 Hz), 7.04-7.01 (1H, m), 6.99-6.72 (2H, m), 6.36 (1H, d, J 9.7 Hz), 4.37-4.29 (1H, m), 3.74-3.47 (4H, m), 1.95-1.74 (3H, m), 1.61-1.53 (1H, m). LCMS (ES$^+$) RT 3.18 minutes, 482 (M+H)$^+$.

EXAMPLE 18

3-Anilino-2-{[(2S)-2-(methoxymethyl)pyrrolidin-1-yl]carbonyl}-7-phenylthieno[2,3-b]pyridin-6(7H)-one The title compound was prepared from Intermediate 29 and (S)-2-(methoxymethyl)pyrrolidine following the method of Example 11 to give the title compound as a pale yellow solid. δH (CDCl$_3$) 9.50 (1H, bs), 7.55-7.46 (3H, m), 7.40-7.30 (2H, m), 7.27 (1H, d, J 9.7 Hz), 7.25-7.18 (2H, m), 6.99-6.95 (3H, m), 6.33 (1H, d, J 9.7 Hz), 4.35-4.30 (1H, m), 3.62-3.56 (1H, m), 3.51-3.43 (2H, m), 3.41-3.30 (1H, m), 3.23 (3H, s), 1.92-1.73 (4H, m). LCMS (ES$^+$) RT 3.49 minutes, 460 (M+H)$^+$.

EXAMPLE 19

3-Anilino-2-{[(2R)-2-(methoxymethyl)pyrrolidin-1-yl]carbonyl}-7-phenylthieno[2,3-b]pyridin-6(7H)-one The title compound was prepared from Intermediate 29 and (R)-2-(methoxymethyl)pyrrolidine following the method of Example 11 to give the title compound as a pale yellow solid. δH (CDCl$_3$) 9.45 (1H, bs), 7.55-7.46 (3H, m), 7.40-7.30 (2H, m), 7.27 (1H, d, J 9.7 Hz), 7.25-7.18 (2H, m), 6.99-6.95 (3H, m), 6.33 (1H, d, J 9.7 Hz), 4.35-4.30 (1H, m), 3.62-3.56 (1H, m), 3.51-3.43 (2H, m), 3.41-3.30 (1H, m), 3.23 (3H, s), 1.92-1.73 (4H, m). LCMS (ES$^+$) RT 3.49 minutes, 460 (M+H)$^+$.

EXAMPLE 20

7-(4-Chlorophenyl)-3-[(4-fluoro-3-methylphenyl)amino]-2-{[(2R)-2-(hydroxymethyl)pyrrolidin-1-yl]carbonyl}thieno[2,3-b]pyridin-6(7H)-one The title compound was prepared from Intermediate 30 (800 mg, 1.87 mmol) and (R)-2-pyrrolidinemethanol (0.28 mL, 2.81 mmol) following the method of Example 11 to give the title compound as a pale yellow solid (251 mg). δH (CDCl$_3$) 9.43 (1H, bs), 7.51-7.48 (2H, m), 7.39-7.19 (2H, m), 7.13 (1H, d, J 9.8 Hz), 6.80-6.76 (3H, m), 6.28 (1H, d, J 9.8 Hz), 4.36-4.25 (2H, m), 3.75-3.50 (4H, m), 2.18 (3H, s), 1.98-1.73 (3H, m), 1.60-1.52 (1H, m). LCMS (ES$^+$) RT 3.39 minutes, 512 (M+H)$^+$.

EXAMPLE 21

3-[(4-Fluoro-3-methylphenyl)amino]-2-{[(2S)-2-(hydroxymethyl)-pyrrolidin-1-yl]carbonyl}-7-(3-methylphenyl)thieno[2,3-b]pyridin-6(7H)-one The title compound was prepared from Intermediate 31 (1.0 g, 2.4 mmol) and (S)-2-pyrrolidinemethanol (0.36 mL, 3.6 mmol) following the method of Example 11 to give the title compound as a pale yellow solid (212 mg). δH (CDCl$_3$) 9.38 (1H, bs), 7.45-7.40 (1H, m), 7.38-7.27 (1H, m), 7.18-7.12 (3H, m), 6.87-6.76 (3H, m), 6.30 (1H, d, J 9.8 Hz), 4.36-4.28 (2H, m), 3.75-3.48 (4H, m), 2.37 (3H, s), 2.18 (3H, s), 1.97-1.82 (3H, m), 1.70-1.59 (1H, m). LCMS (ES$^+$) RT 3.34 minutes, 492 (M+H)$^+$.

EXAMPLE 22

2-{[(2R)-2-(Hydroxymethyl)pyrrolidin-1-yl]carbonyl}-7-(3-methylphenyl)-3-[(3-methylphenyl)amino]thieno[2,3-b]pyridin-6(7H)-one The title compound was prepared from Intermediate 32 (842 mg, 2.15 mmol) and (R)-2-pyrrolidinemethanol (0.32 mL, 3.23 mmol) following the method of Example 11 to give the title compound as a pale yellow solid (179 mg). δH (CDCl$_3$) 9.21 (1H, bs), 7.40-7.35 (1H, m), 7.27-7.24 (2H, m), 7.18-7.07 (3H, m), 6.81-6.76 (3H, m), 6.31 (1H, d, J 9.7 Hz), 4.30-4.22 (2H, m), 3.70-3.46 (4H, m), 2.37 (3H, s), 2.25 (3H, s), 1.98-1.66 (3H, m), 1.58-1.47 (1H, m). LCMS (ES$^+$) RT 3.30 minutes, 474 (M+H)$^+$.

EXAMPLE 23

3-[(4-Fluoro-3-methylphenyl)amino]-2-{[(2R)-2-(hydroxymethyl)-pyrrolidin-1-yl]carbonyl}-7-(3-methylphenyl)thieno[2,3-b]pyridin-6(7H)-one The title compound was prepared from Intermediate 31 (640 mg, 1.54 mmol) and (R)-2-pyrrolidinemethanol (0.25 mL, 2.3 mmol) following the method of Example 11 to give the title compound as a pale yellow solid (112 mg). δH (CDCl$_3$) 7.49-7.35 (1H, m), 7.26 (1H, d, J 9.7 Hz), 7.24-7.23 (3H, m), 6.98-6.91 (3H, m), 6.88 (1H, d, J 9.8 Hz), 4.39-4.35 (1H, m), 3.83-3.56 (4H, m), 2.45 (3H, s), 2.26 (3H, s), 1.99-1.81 (3H, m), 1.68-1.60 (1H, m). LCMS (ES$^+$) RT 3.34 minutes, 492 (M+H)$^+$.

EXAMPLE 24

3-[(3-Chloro-4-fluorophenyl)amino]-2-{[(2R)-2-(hydroxymethyl)-pyrrolidin-1-yl]carbonyl}-7-phenylthieno[2,3-b]pyridin-6(7H)-one The title compound was prepared from Intermediate 33 (340 mg, 0.77 mmol) and (R)-2-pyrrolidinemethanol (0.12 mL, 1.16 mmol) following the method of Example 11 to give the title compound as a yellow solid (71 mg). δH (CDCl$_3$) 7.58-7.51 (3H, m), 7.34-7.21 (2H, m), 7.19-7.17 (1H, m), 7.05-6.98 (2H, m), 6.88-6.82 (1H, m), 6.38 (1H, d, J 9.7 Hz), 4.34-4.30 (1H, m), 3.72-3.48 (4H, m), 1.99-1.53 (4H, m). LCMS (ES$^+$) RT 3.21 minutes, 498 (M+H)$^+$.

EXAMPLE 25

3-[(3-Chloro-4-fluorophenyl)amino]-2-{[(2S)-2-(hydroxymethyl)-pyrrolidin-1-yl]carbonyl}-7-phenylthieno[2,3-b]pyridin-6(7H)-one The title compound was prepared from Intermediate 33 (340 mg, 0.77 mmol) and (S)-2-pyrrolidinemethanol (0.12 mL, 1.16 mmol) following the method of Example 11 to give the title compound as a yellow solid (65 mg). δH (CDCl$_3$) 7.66-7.59 (3H, m), 7.44-7.31 (2H, m), 7.28-7.26 (1H, m), 7.14-7.08 (2H, m), 6.98-6.93 (1H, m), 6.47 (1H, d, J 9.8 Hz), 4.43-4.40 (1H, m), 3.81-3.57 (4H, m), 2.06-1.62 (4H, m). LCMS (ES$^+$) RT 3.21 minutes, 498 (M+H)$^+$.

EXAMPLE 26

3-[(4-Fluoro-3-methylphenyl)amino]-2-{[(2R)-2-(hydroxymethyl)-pyrrolidin-1-yl]carbonyl}-7-phenylthieno[2,3-b]pyridin-6(7H)-one (R)-2-Pyrrolidinemethanol (0.398 mL, 4.037 mmol) was added to a solution of Intermediate 34 (1.5 g, 2.69 mmol) in DCM (20 mL) and the mixture stirred at r.t. for 24 h. The volatiles were removed in vacuo and the residue was purified by column chromatography (silica, 1-10% THF in DCM) to produce the title compound as an orange solid (0.737 g). δH (DMSO-d6) 8.45 (1H, s), 7.65-7.55 (4H, br m), 7.49-7.46 (2H, m), 6.98-6.93 (1H, m), 6.88-6.86 (1H, m), 6.80-6.76 (1H, m), 6.42 (1H, d, J 9.63 Hz), 4.06 (1H, m), 3.45-3.36 (3H, m), 3.21-3.17 (2H, m), 2.08 (3H, s), 1.85-1.74 (3H, m), 1.68-

1.60 (1H, m). LCMS (ES$^+$) 478 (M+H)$^+$. HPLC Chiralpak AS 80:20 Isohexane/EtOH. RT 19.62 minutes.

EXAMPLE 27

3-[(4-Fluoro-3-methylphenyl)amino]-2-{[(2S)-2-(hydroxymethyl)-pyrrolidin-1-yl]carbonyl}-7-phenylthieno[2,3-b]pyridin-6(7H)-one (S)-2-Pyrrolidinemethanol (0.198 mL, 2.007 mmol) was added to a solution of Intermediate 34 (0.750 g, 1.338 mmol) in DCM (10 mL) and the mixture stirred at r.t. for 24 h. The volatiles were removed in vacuo and the residue was purified by column chromatography (silica, 1-10% THF in DCM) to produce the title compound as an orange solid (0.369 g). δH (DMSO-d6) 8.46 (1H, s), 7.65-7.55 (4H, br m), 7.49-7.46 (2H, m), 6.98-6.93 (1H, m), 6.88-6.86 (1H, m), 6.80-6.76 (1H, m), 6.42 (1H, d, J 9.63 Hz), 4.05 (1H, m), 3.46-3.35 (3H, m), 3.20-3.16 (2H, m), 2.19 (3H, s), 1.84-1.72 (3H, m), 1.68-1.60 (1H, m). LCMS (ES$^+$) 478 (M+H)$^+$. HPLC Chiralpak AS 80:20 Isohexane/EtOH. RT 15.37 minutes.

EXAMPLE 28

3-[(2,4-Difluorophenyl)amino]-2-{[(3S)-3-hydroxypyrrolidin-1-yl]carbonyl}-7-phenylthieno[2,3-b]pyridin-6(7H)-one (S)-3-Hydroxypyrrolidine (107 mg, 1.23 mmol) was added to a solution of Intermediate 35 (400 mg, 0.709 mmol) in DCM (8 mL) and the reaction stirred at room temperature for 24 h. The volatiles were removed in vacuo and the crude residue purified by column chromatography (silica, 5-15% THF in DCM) and (silica, 20-80% EtOAc in isohexane) to give the title compound as a pale yellow solid (156 mg). δH (CDCl$_3$) 7.46-7.53 (3H, m), 7.33 (2H, m), 7.19 (1H, d, J 10.2 Hz), 6.95-7.01 (1H, m), 6.82-6.87 (1H, m), 6.72-6.76 (1H, m), 6.35-6.38 (1H, m), 4.22 (1H, m), 3.64-3.69 (2H, m), 3.62 (1H, m), 3.55 (1H, m), 1.89-1.94 (2H, m). LCMS (ES$^+$) RT 2.98 minutes, 468 (M+H)$^+$.

EXAMPLE 29

3-[(2,4-Difluorophenyl)amino]-2-{[(3R)-3-hydroxypyrrolidin-1-yl]carbonyl}-7-phenylthieno[2,3-b]pyridin-6(7H)-one (R)-3-Hydroxypyrrolidine (107 mg, 1.23 mmol) was added to a solution of Intermediate 35 (232 mg, 0.411 mmol) in DCM (4 mL) and the reaction stirred at room temperature for 24 h. The volatiles were removed in vacuo and the crude residue purified by column chromatography (silica, 5-15% THF in DCM) to give the title compound as a pale yellow solid (91 mg). δH (CDCl$_3$) 7.48 (3H, m), 7.31 (2H, m), 7.15 (1H, d, J 9.7 Hz), 6.95 (1H, m), 6.82 (1H, m), 6.72 (1H, m), 6.34 (1H, d, J 9.7 Hz), 4.41 (1H, m), 3.67-3.59 (3H, m), 3.53 (1H, m), 1.90 (2H, m). LCMS (ES$^+$) RT 2.95 minutes, 468 (M+H)$^+$.

EXAMPLE 30

3-[(4-Fluoro-3-methylphenyl)amino]-2-{[(3S)-3-hydroxypyrrolidin-1-yl]carbonyl}-7-phenylthieno[2,3-b]pyridin-6(7H)-one The title compound was prepared from (S)-3-hydroxypyrrolidine (100 mg, 1.10 mmol) and Intermediate 34 (200 mg, 0.36 mmol) following the method of Example 28 to give the title compound as a pale yellow solid (55 mg). δH (CDCl$_3$) 7.51 (3H, m), 7.34 (2H, m), 7.19 (1H, m), 6.84 (2H, m), 6.80 (1H, m), 6.33 (1H, d, J 9.75 Hz), 4.44 (1H, m), 3.66 (4H, m), 2.18 (3H, s), 1.91 (2H, m). LCMS (ES$^+$) RT 3.02 minutes, 464 (M+H)$^+$.

EXAMPLE 31

3-[(4-Fluoro-3-methylphenyl)amino]-2-{[(3R)-3-hydroxypyrrolidin-1-yl]carbonyl}-7-phenylthieno[2,3-b]pyridin-6(7H)-one The title compound was prepared from (R)-3-hydroxypyrrolidine (100 mg, 1.10 mmol) and Intermediate 34 (200 mg, 0.36 mmol) following the method of Example 28 to give the title compound as a pale yellow solid (73 mg). δH (CDCl$_3$) 7.65 (3H, m), 7.60 (2H, m), 7.29 (1H, m), 6.90 (3H, m), 6.48 (1H, d, J 9.73 Hz), 4.58 (1H,m), 3.80 (3H, m), 3.76 (1H, m), 2.31 (3H, s), 2.07 (2H, m). LCMS (ES$^+$) RT 3.02 minutes, 464 (M+H)$^+$.

EXAMPLE 32

3[(2,4-Difluorophenyl)amino]-2-{[(3S,4S)-3,4-dihydroxypyrrolidin-1-yl]carbonyl}-7-phenylthieno[2,3-b]pyridin-6(7H)-one The title compound was prepared from (S,S)-3,4-dihydroxypyrrolidine (110 mg, 1.10 mmol) and Intermediate 35 (200 mg, 0.35 mmol) following the method of Example 28 to give the title compound as a pale yellow solid (144 mg). δH (CDCl$_3$) 9.49 (1H, s), 7.51 (3H, m), 7.34 (2H, m); 7.18 (1H, m), 6.93 (1H, m), 6.84 (1H, m), 6.82 (1H, m), 6.36 (1H, d, J 9.72 Hz), 4.15 (2H, m), 3.83 (2H, m), 3.57 (2H, d, J 12.4 Hz). LCMS (ES$^+$) RT 2.74 minutes, 484 (M+H)$^+$.

EXAMPLE 33

3-[(2,4-Difluorophenyl)amino]-2-[(3-hydroxyazetidin-1-yl)carbonyl]-7-phenylthieno[2,3-b]pyridin-6(7H)-one The title compound was prepared from 3-hydroxyazetidine hydrochloride (110 mg, 1.05 mmol) and Intermediate 35 (200 mg, 0.35 mmol) with the addition of diisopropylethylamine (0.195 mL, 1.12 mmol) following the method of Example 28 to give the title compound as a white solid (64 mg). δH (CDCl$_3$) 9.48 (1H, s), 7.53 (3H, m), 7.32 (2H, m), 7.10 (1H, d, J 9.7 Hz), 6.86 (1H, m), 6.83 (1H, m), 6.74 (1H, m), 6.33 (1H, d, J 9.8 Hz), 4.58 (1H, s), 4.34 (2H, m), 3.94 (2H, m), 2.07 (1H, s). LCMS (ES$^+$) RT 3.06 minutes, 454 (M+H)$^+$.

EXAMPLE 34

3-[(2,4-Difluorophenyl)amino]-2-{[(2S)-2-(1-hydroxy-1-methylethyl)pyrrolidin-1-yl]carbonyl}-7-phenylthieno[2,3-b]pyridin-6(7H)-one The title compound was prepared from 2-[(2S)pyrrolidin-2-yl]propan-2-ol (140 mg, 1.05 mmol) and Intermediate 35 (200 mg, 0.35 mmol) following the method of Example 28 to give the title compound as a pale yellow solid (140 mg). δH (CDCl$_3$) 8.95 (1H, s), 7.51 (3H, m), 7.49 (2H, m), 7.19 (1H, m), 6.87 (1H, m), 6.84 (1H, m), 6.76 (1H, m), 6.37 (1H, d, J 9.7 Hz), 4.36 (1H, m), 3.90 (1H, m), 3.34 (1H, m), 1.93 (1H, m), 1.84 (1H, m), 1.67 (2H, m), 1.13 (3H, s), 1.00 (3H, s). LCMS (ES+) RT 3.47 minutes, 510 (M+H)+.

EXAMPLE 35

3-[(2,4-Difluorophenyl)amino]-2-{[(2R)-2-(1-hydroxy-1-methylethyl)pyrrolidin-1-yl]carbonyl}-7-phenylthieno[2,3-b]pyridin-6(7H)-one The title compound was prepared from 2-[(2R)-pyrrolidin-2-yl]propan-2-ol hydrochloride (165 mg, 1.05 mmol) and Intermediate 35 (200 mg, 0.35 mmol) with the addition of diisopropylethylamine (0.20 mL, 1.12 mmol) following the method of Example 28 to give the title compound as an off-white solid (89 mg). δH (CDCl$_3$) 8.96 (1H, s), 7.63 (3H, m), 7.32 (2H, m), 7.23 (1H, m), 7.01 (1H, m), 6.83 (1H, m), 6.74 (1H, m), 6.38 (1H, d, J 9.7 Hz), 5.00 (1H, s), 4.32 (1H, m), 3.90 (1H, m), 3.33 (1H, m), 2.00 (2H, m), 1.92 (2H, m), 1.15 (3H, s), 1.00 (3H, s). LCMS (ES+) RT 3.47 minutes, 510 (M+H)+.

EXAMPLE 36

3-[(2-Cyanophenyl)amino]-2-{[(2S)-2-(hydroxymethyl)pyrrolidin-1-yl]carbonyl}-7-phenylthieno[2,3-b]pyridin-6(7H)-one To a suspension of Intermediate 17 (400 mg, 0.96 mmol) in 2-ethoxyethanol (5 mL) was added (S)-2-pyrrolidinemethanol (0.48 mL, 4.81 mmol) and the reaction heated at 78° C. for 2 days. Solvent was removed in vacuo and the residue purified by column chromatography (silica, 30-80% EtOAc in isohexane) to give the title compound as a solid (123 mg). δH (CDCl$_3$) 9.26 (1H, bs), 7.57-7.48 (4H, m), 7.40-7.36 (3H, m), 7.26 (1H, d, J 9.7 Hz), 7.00-6.95 (2H, m), 6.44 (1H, d, J 9.7 Hz), 4.29-4.33 (1H, m), 3.68-3.61 (2H, m), 3.52-3.46 (2H, m), 1.97-1.83 (2H, m), 1.81-1.73 (1H, m), 1.60-1.53 (1H, m). LCMS (ES+) RT 2.98 minutes, 471 (M+H)+.

EXAMPLE 37

3-[(2-Cyanophenyl)amino]-2-{[(2R)-2-(hydroxymethyl)pyrrolidin-1-yl]carbonyl}-7-phenylthieno[2,3-b]pyridin-6(7H)-one To a suspension of Intermediate 17 (400 mg, 0.96 mmol) in 2-ethoxyethanol (5 mL) was added (R)-2-pyrrolidinemethanol (0.48 mL, 4.81 mmol) and the reaction heated at 78° C. for 2 days. Solvent was removed in vacuo and the residue purified by column chromatography (silica, 30-80% EtOAc in isohexane) to give the title compound as a white solid (105 mg). δH (CDCl$_3$) 9.25 (1H, bs), 7.57-7.48 (4H, m), 7.45-7.36 (3H, m), 7.26 (1H, d, J 9.7 Hz), 7.00-6.95 (2H, m), 6.44 (1H, d, J 9.7 Hz), 4.30 (1H, m), 3.71-3.61 (2H, m), 3.52-3.47 (2H, m), 2.00-1.87 (2H, m), 1.80-1.70 (1H, m), 1.65-1.60 (1H, m). LCMS (ES+) RT 2.94 minutes, 471 (M+H)+.

EXAMPLE 38

3-Anilino-7-(cyclopropylmethyl)-2-{[(2R)-2-(hydroxymethyl)pyrrolidin-1-yl]carbonyl}thieno[2,3-b]pyridin-6(7H)-one A mixture of Intermediate 26 (500 mg, 1.4 mmol) and (R)-2-pyrrolidinemethanol (2 mL, 20 mmol) was heated at 130° C. in a sealed Schlenk tube for 6 h. The reaction was cooled to room temperature and partitioned between EtOAc (50 mL) and water (50 mL). The EtOAc layer was washed with water (2×20 mL), dried (Na$_2$SO$_4$) and concentrated in vacuo. The crude residue was purified by column chromatography (silica, 20-50% EtOAc in DCM) to give the title compound as a yellow solid (405 mg, 70%). δH (CDCl$_3$) 9.31 (1H, bs), 7.23-7.14 (3H, m), 6.99-6.94 (3H, m), 6.24 (1H, d, J 9.7 Hz), 4.40-4.34 (1H, m), 4.18-4.16 (1H, m) 3.98-3.88 (3H, m), 3.76-3.58 (3H, m), 2.04-1.93 (3H, m), 1.90-1.81 (1H, m), 1.67-1.61 (1H, m), 0.62-0.58 (4H, m). LCMS (ES+) RT 3.12 minutes, 424 (M+H)+.

EXAMPLE 39

3-[(3-Cyanophenyl)amino]-2-{[(2R)-2-(hydroxymethyl)pyrrolidin-1-yl]carbonyl}-7-phenylthieno[2,3-b]pyridin-6(7H)-one To a suspension of Intermediate 16 (224 mg) in 2-ethoxyethanol (2 mL) was added (R)-2-pyrrolidinemethanol (1.0 mL) and the reaction heated at 110° C. for 18 h in a sealed tube. Solvent was removed in vacuo and the residue purified by column chromatography (silica, 70% EtOAc in isohexane) to give the title compound as a white solid (112 mg). δH (DMSO-d6) 9.18 (1H, s), 7.90 (1H, dd, J 9.6, 1.3 Hz), 7.80-7.62 (5H, m), 7.51 (1H, t, J 7.9 Hz), 7.37-7.25 (3H, m), 6.69 (1H, d, J 9.6 Hz), 4.75 (1H, m), 4.00 (1H, m), 3.50-3.28 (3H, m), 2.90 (1H, m), 1.95-1.65 (4H, m). LCMS (ES+) RT 2.99 minutes, 471 (M+H)+.

EXAMPLE 40

3-[(2,4-Difluorophenyl)amino]-2-{[(2R)-2-(hydroxymethyl)pyrrolidin-1-yl]sulfonyl}-7-phenylthieno[2,3-b]pyridin-6(7H)-one A mixture of Intermediate 62 (340 mg), trifluoroacetic acid (5 mL) and DCM (20 mL) was stirred at r.t. overnight. Solvents were removed in vacuo and the residue azeotroped with toluene (×3). The residue was dissolved in DCM, treated with triethylamine (10 mL) and the mixture concentrated in vacuo. Purification by column chromatography (silica, 20% EtOAc in DCM) gave the title compound (160 mg, 23%). δH (CDCl$_3$) 7.58-7.49 (3H, m), 7.36-7.31 (3H, m), 7.02 (1H, d, J 9.9 Hz), 6.99-6.78 (3H, m), 6.38 (1H, d, J 9.9 Hz), 3.73-3.69 (1H, m), 3.65-3.45 (2H, m), 3.35-3.28 (1H, m), 3.25-3.17 (1H, m), 2.15 (1H br m), 1.97-1.60 (4H, m). LCMS (ES+) RT 3.34 minutes, 518 (M+H)+.

EXAMPLE 41

2-{[(3R)-3-Aminopyrrolidin-1-yl]carbonyl}-3-[(2,4-difluorophenyl)amino]-7-phenylthieno[2,3-b]pyridin-6(7H)-one Intermediate 35 (1 g, 1.77 mmol) and (R)-3-aminopyrrolidine dihydrochloride (309 mg, 1.95 mmol) were dissolved in dichloromethane (50 mL) and treated with triethylamine (360 mg, 3.0 mmol). After stirring at room temperature for 18 h the reaction mixture was washed with water, the organic phase separated, dried (sodium sulphate) and concentrated in vacuo. The crude product was purified by column chromatography (silica, 0-100% THF in DCM) to give the title compound as a white solid (300 mg). NMR δH (DMSO) 9.08 (1H, brs), 7.67-7.50 (6H, m), 7.35-7.27 (1H, m), 7.06-6.93 (2H, m), 6.47 (1H, d, J 9.7 Hz), 3.43-3.32 (2H, m), 3.31-3.28 (1H, m), 3.00 (1H, dd, J 4.0, 10.5 Hz), 1.89-1.77 (1H, m), 1.65-1.53 (1H, m), 1.52-1.45 (1H, m). LCMS (ES+) RT 2.25 minutes, 467 (M+H)+.

General Procedure for Preparing Amide Examples from Pentafluoro-phenyl Esters The following Examples 42-53 were all prepared from the appropriate pentafluorophenyl ester intermediate and amine starting materials following the method described for Example 41. Where necessary reactions were run in the presence of a tertiary amine base such as triethylamine to neutralise acid salts of the starting materials.

EXAMPLE 42

2-{[(2S)-2-(Aminomethyl)pyrrolidin-1-yl]carbonyl}-3-[(2,4-difluorophenyl)amino]-7-phenylthieno[2,3-b]pyridin-6(7H)-one Prepared from Intermediate 35 (1 g, 1.77 mmol), (S)-2-(aminomethyl)-pyrrolidine (192 mg, 1.95 mmol) and triethylamine (360 mg, 3.0 mmol) by the method of Example 41. Chromatography (silica, 0-100% THF in DCM) gave the title compound as a white solid (296 mg). NMR $\delta$H (DMSO) 8.73 (1H, brs), 7.74 (1H, d, J 9.3 Hz), 7.66-7.56 (3H, m), 7.52-7.50 (2H, m), 7.29 (1H, dt, J 2.6, 8.9 Hz), 6.99-6.89 (2H, m), 6.42 (1H, d, J 9.6 Hz), 3.88-3.78 (1H, m), 2.43 (1H, dd, J 3.7, 12.6 Hz), 2.12 (1H, dd, J 7.9, 12.5 Hz), 1.75-1.56 (4H, m), 1.30-1.11 (2H, brm). LCMS (ES$^+$) RT 2.32 minutes, 481 (M+H)$^+$.

EXAMPLE 43

2-{[(2R)-2-(Aminomethyl)pyrrolidin-1-yl]carbonyl}-3-[(2,4-difluorophenyl)amino]-7-phenylthieno[2,3-b]pyridin-6(7H)-one Prepared from Intermediate 35 (1 g, 1.77 mmol), (R)-2-(aminomethyl)-pyrrolidine (350 mg, 1.95 mmol) and triethylamine (2 mL, 14.3 mmol) by the method of Example 41. Chromatography (reverse phase silica, 60% ethanol:40% water) gave the title compound as a white solid (390 mg). NMR $\delta$H (CDCl$_3$) 9.38 (1H, s), 7.64-7.54 (3H, m), 7.50-7.31 (2H, m), 7.32-7.24 (1H, m), 7.11-7.03 (1H, m), 6.97-6.90 (1H, m), 6.87-6.81 (1H, m), 6.44 (1H, d, J 9.7 Hz), 4.33-4.27 (1H, m), 3.77-3.67 (1H, m), 3.61-3.54 (1H, m), 2.95 (1H, dd, J 5.1, 12.9 Hz), 2.83 (1H, dd, J 6.1, 12.9 Hz), 2.08-1.74 (4H, m). LCMS (ES$^+$) RT 2.32 minutes, 481 (M+H)$^+$.

EXAMPLE 44

3-[(2,4-Difluorophenyl)amino]-2-{[(3R)-3-(dimethylamino)pyrrolidin-1-yl]carbonyl}-7-phenylthieno[2,3-b]pyridin-6(7H)-one Prepared from Intermediate 35 (0.75 g, 1.33 mmol) and (R)-3-(dimethylamino)pyrrolidine (166 mg, 1.46 mmol) by the method of Example 41. Chromatography (reverse phase silica, 60% ethanol:40% water) gave the title compound as a white solid (440 mg). NMR $\delta$H (DMSO) 8.82 (1H, s), 7.67-7.59 (4H, m), 7.52-7.49 (2H, m), 7.35-7.27 (1H, m), 7.03-6.91 (2H, m), 6.48 (1H, d, J 9.7 Hz), 3.50-3.21 (4H, m), 3.00 (1H, t, J 8.9 Hz), 2.06 (6H, s), 1.96-1.92 (1H, m), 1.59-1.49 (1H, m). LCMS (ES$^+$) RT 2.266 minutes, 495 (M+H)$^+$.

EXAMPLE 45

3-[(2,4-Difluorophenyl)amino]-2-[(4-hydroxypiperidin-1-yl)carbonyl]-7-phenylthieno[2,3-b]pyridin-6(7H)-one Prepared from Intermediate 35 (200 mg, 0.36 mmol) and 4-hydroxypiperidine (110 mg, 1.1 mmol) by the method of Example 41 to give the title compound as a white powder (100 mg). NMR $\delta$H (CDCl$_3$) 7.93 (1H, s), 7.51 (3H, m), 7.35 (2H, m), 7.24 (1H, d, J 9.7 Hz), 6.81-6.93 (2H, m), 6.75 (1H, m), 6.41 (1H, d, J 9.7 Hz), 3.86 (3H, m), 3.22 (2H, m), 1.77 (2H, m), 1.40 (2H, m). LCMS (ES$^+$) RT 2.90 minutes, 482 (M+H)$^+$.

EXAMPLE 46 rac-3-[(2,4-Difluorophenyl)amino]-2-[(3-hydroxypiperidin-1-yl)carbonyl]-7-phenylthieno[2,3-b]pyridin-6(7H)-one Prepared from Intermediate 35 (200 mg, 0.36 mmol), 3-hydroxypiperidine hydrochloride (98 mg, 0.70 mmol) and diisopropylethylamine (101 mg, 0.78 mmol) by the method of Example 41. Chromatography (silica, 15% THF in DCM) gave the title compound as a white solid (137 mg). NMR $\delta$H (CDCl$_3$) 7.46-7.55 (3H, m), 7.33-7.35 (2H, m), 7.23 (1H, d, J 9.7 Hz), 6.82-6.93 (2H, m), 6.70-6.75 (1H, m), 6.41 (1H, d, J 9.7 Hz), 3.72-3.77 (1H, m), 3.56-3.60 (1H, m), 3.38-3.49 (3H, m), 1.70-1.80 (2H, m), 1.53-1.59 (1H, m), 1.38-1.42 (1H, m). LCMS (ES$^+$) RT 3.02 minutes, 482 (M+H)$^+$.

EXAMPLE 47

2-{[(3R)-3-Aminopyrrolidin-1-yl]carbonyl}-3-[(4-fluoro-3-methylphenyl)amino]-7-phenylthieno[2,3-b]pyridin-6(7H)-one Prepared from Intermediate 34 (1.0 g, 1.79 mmol), (R)-3-aminopyrrolidine dihydrochloride (311 mg, 1.96 mmol) and triethylamine (1 mL, 7.2 mmol) by the method of Example 41. Chromatography (silica, 10% isopropanol in DCM) gave the title compound as a yellow solid (620 mg). NMR $\delta$H (CDCl$_3$) 9.54 (1H, bs), 7.56-7.44 (3H, m), 7.34-7.31 (2H, m), 7.19-7.14 (1H, m), 6.88-6.75 (3H, m), 6.31 (1H, d, J 10.2 Hz), 3.73-3.65 (2H, m), 3.59-3.52 (2H, m), 3.29 (1H, dd, J 11.0, 4.5 Hz), 2.37-2.06 (2H, bm), 2.17 (3H, d, J 2.3 Hz), 2.04-1.95 (1H, m), 1.70-1.62 (1H, m). LCMS (ES$^+$) RT 2.33 minutes, 463 (M+H)$^+$.

EXAMPLE 48

2-{[(2S)-2-(Aminomethyl)pyrrolidin-1-yl]carbonyl}-3-[(4-fluoro-3-methylphenyl)amino]-7-phenylthieno[2,3-b]pyridin-6(7H)-one Prepared from Intermediate 34 (1.0 g, 1.79 mmol), (S)-2-(aminomethyl)-pyrrolidine (200 mg) and triethylamine (1 mL) by the method of Example 41. Chromatography (reverse phase silica, 60% MeCN in water) gave the title compound as a white solid (260 mg). NMR $\delta$H (CDCl$_3$) 9.57 (1H, bs), 7.64-7.55 (3H, m), 7.43-7.31 (2H, m), 7.28-7.24 (1H, m), 6.98-6.84 (3H, m), 6.40 (1H, d, J 9.7 Hz), 4.30-4.23 (1H, m), 3.75-3.69 (1H, m), 3.61-3.54 (1H, m), 2.94 (1H, dd J 11.8, 4.4 Hz), 2.75 (1H, dd, J 12.8, 7.0 Hz), 2.27 (3H, d, J 1.8 Hz), 2.04-1.74 (4H, m). LCMS (ES$^+$) RT 2.36 minutes, 477 (M+H)$^+$.

EXAMPLE 49

3-[(4-Fluoro-3-methylphenyl)amino]-2-{[(3R)-3-(dimethylamino)-pyrrolidin-1-yl]carbonyl}-7-phenylthieno[2,3-b]pyridin-6(7H)-one Prepared from Intermediate 34 (1.0 g, 1.79 mmol), (R)-3-(dimethylamino)-pyrrolidine (245 mg, 2.15 mmol) and triethylamine (1 mL) by the method of Example 41. Chromatography (silica, 50-100% MeCN in DCM) gave the title compound as a pale yellow solid (610 mg). NMR δH (CDCl$_3$) 9.50 (1H, bs), 7.55-7.45 (3H, m), 7.34-7.32 (2H, m), 7.17 (1H, d, J 9.8 Hz), 6.89-6.75 (3H, m), 6.31 (1H, d, J 9.8 Hz), 3.81-3.68 (2H, m), 3.52-3.42 (1H, m), 3.31-3.24 (1H, m), 2.67-2.57 (1H, m), 2.17 (9H, s), 2.06-1.93 (1H, m), 1.80-1.70 (1H, m). LCMS (ES$^+$) RT 2.34 minutes, 491 (M+H)$^+$.

EXAMPLE 50

3-[(2,4-Difluorophenyl)amino]-2-{[(3R,4R)-3,4-dihydroxypyrrolidin-1-yl]carbonyl}-7-phenylthieno[2,3-b]pyridin-6(7H)-one Prepared from Intermediate 35 (196 mg, 0.35 mmol) and (3R,4R)-3,4-dihydroxypyrrolidine (107 mg, 1.04 mmol) by the method of Example 41. Column chromatography (silica, 0-8% MeOH in DCM) gave the title compound as a yellow solid (111 mg). NMR δH (CDCl$_3$) 7.33-7.41 (3H, m), 7.20 (2H, bm), 7.02 (1H, m), 6.82-6.88 (1H, m), 6.68-6.74 (1H, m), 6.58-6.63 (1H, m), 6.23 (1H, d, J 9.7 Hz), 4.02 (2H, m), 3.69 (2H, m), 3.43 (2H, d, J 12.5 Hz). LCMS (ES$^+$) RT 2.79 minutes, 484 (M+H)$^+$.

EXAMPLE 51

3-[(2,4-Difluorophenyl)amino]-2-{[(3R*,4S*)-3,4-dihydroxypyrrolidin-1-yl]carbonyl}-7-phenylthieno[2,3-b]pyridin-6(7H)-one Prepared from Intermediate 35 (250 mg, 0.44 mmol), cis-3,4-dihydroxy-pyrrolidine hydrochloride (130 mg, 0.94 mmol) and diisopropylethylamine (127 mg, 0.98 mmol) by the method of Example 41. Column chromatography (silica, 5-15% THF in DCM) gave the title compound as a yellow solid (98 mg). NMR δH (CDCl$_3$) 7.48-7.56 (3H, m), 7.31-7.34 (2H, m), 7.15 (1H, m), 6.96-7.02 (1H, m), 6.82-6.88 (1H, m), 6.72-6.78 (1H, m), 6.36 (1H, d, J 9.7 Hz), 4.20-4.22 (2H, m), 3.77 (2H, m), 3.53 (2H, m). LCMS (ES$^+$) RT 2.84 minutes, 484 (M+H)$^+$.

EXAMPLE 52

3-[(2-Cyanophenyl)amino]-2-{[(3S)-3-hydroxypyrrolidin-1-yl]carbonyl}-7-phenylthieno[2,3-b]pyridin-6(7H)-one Prepared from Intermediate 67 (340 mg, 0.61 mmol) and (S)-3-hydroxy-pyrrolidine (227 mg, 2.60 mmol) by the method of Example 41. Column chromatography (silica, 30-100% EtOAc in isohexane) gave the title compound as a white solid (210 mg). NMR δH (DMSO) 9.68 (1H, s), 7.86 (1H, m), 7.72-7.81 (4H, m), 7.63-7.71 (3H, m), 7.19 (1H, m), 7.12 (1H, d), 6.64 (1H, d, J 9.7 Hz), 5.07 (1H, bs), 4.34 (1H, bs), 3.59 (3H, m), 3.39 (1H, m), 1.88-1.97 (2H, m). LCMS (ES$^+$) RT 2.81 minutes, 457 (M+H)$^+$.

EXAMPLE 53

3-[(2-Cyanophenyl)amino]-2-{[(3R)-3-hydroxypyrrolidin-1-yl]carbonyl}-7-phenylthieno[2,3-b]pyridin-6(7H)-one Prepared from Intermediate 67 (340 mg, 0.61 mmol) and (R)-3-hydroxy-pyrrolidine (227 mg, 2.60 mmol) by the method of Example 41. Column chromatography (silica, 30-100% EtOAc in isohexane) gave the title compound as a white solid (225 mg). NMR δH (DMSO) 9.59 (1H, s), 7.70 (1H, m), 7.62-7.73 (4H, m), 7.54-7.60 (3H, m), 7.10 (1H, m), 7.03 (1H, m), 6.56 (1H, d, J 9.7 Hz), 4.98 (1H, bs), 4.25 (1H, bs) 3.51 (3H, m), 3.30 (1H, m), 1.79-1.88 (2H, m). LCMS (ES$^+$) RT 2.81 minutes, 457 (M+H)$^+$.

EXAMPLE 54 rac-2-{[3-Aminopyrrolidin-1-yl]carbonyl}-3-[(2,4-difluorophenyl)amino]-7-phenylthieno[2,3-b]pyridin-6(7H)-one Intermediate 64 (270 mg, 0.48 mmol) was dissolved in 4M HCl in dioxane (30 mL) and stirred at r.t. for 18 h. The reaction mixture was concentrated in vacuo and the residue dissolved in DCM and washed with sat. NaHCO$_3$(aq) (×2). The organic layer was separated, dried (MgSO$_4$) and the crude product purified by column chromatography (silica, 2-6% MeOH in DCM) to give the title compound as a white solid (89 mg). NMR δH (DMSO) 9.01 (1H, s), 7.42-7.59 (6H, m), 7.25 (1H, m), 6.98 (2H, m), 6.40 (1H, d, J 9.7 Hz), 5.50 (1H, bm), 3.45 (3H, m), 3.20 (1H, m), 1.86 (1H, m), 1.65 (1H, m). LCMS (ES$^+$) RT 2.23 minutes, 467 (M+H)$^+$.

EXAMPLE 55

2-{[(3S)-3-Aminopyrrolidin-1-yl]carbonyl}-3-[(2,4-difluorophenyl)amino]-7-phenylthieno[2,3-b]pyridin-6(7H)-one Intermediate 65 (0.7 g, 1.24 mmol) was dissolved in dichloromethane (10 mL), treated with trifluoroacetic acid (5 mL) and stirred at room temperature for 2 h. The reaction mixture was concentrated in vacuo and the residual trifluoroacetic acid removed by azeotrope with heptane. The resulting yellow oil was redissolved in dichloromethane, washed with sodium hydrogen-carbonate solution, dried over sodium sulphate and concentrated in vacuo. Chromatography (reverse phase silica, 60% ethanol:40% water) gave the title compound as a white solid (336 mg). NMR δH (DMSO) 9.08 (1H, s), 7.66-7.50 (6H, m), 7.35-7.27 (1H, m), 7.08-6.94 (2H, m), 6.47 (1H, d, J 9.7 Hz), 3.43-3.35 (2H, m), 3.02-2.98 (1H, m), 1.83-1.76 (1H, m), 1.68-1.48 (3H, m). LCMS (ES$^+$) RT 2.239 minutes, 467 (M+H)$^+$.

EXAMPLE 56

2-{[(3S)-3-Aminopyrrolidin-1-yl]carbonyl}-3-[(4-fluoro-3-methylphenyl)amino]-7-phenylthieno[2,3-b]pyridin-6(7H)-one Intermediate 66 (1.2 g, 1.79 mmol) was dissolved in dioxane (20 mL), treated with c.HCl (5 mL) and stirred at room temperature for 20 minutes. The reaction mixture was diluted with DCM (100 mL) and neutralised with sat. NaHCO₃(aq). The aqueous was extracted with several portions of DCM and the combined extracts dried (MgSO₄) and concentrated in vacuo. The crude product was purified by column chromatography (silica, 50-100% MeCN in DCM and then 15% isopropanol in DCM) to give the title compound as a pale yellow solid (520 mg). NMR δH (CDCl₃) 9.57 (1H, bs), 7.56-7.46 (3H, m), 7.35-7.32 (2H, m), 7.19-7.15 (1H, m), 6.89-675 (3H, m), 6.31 (1H, d, J 9.7 Hz), 3.74-3.66 (2H, m), 3.61-3.53 (2H, m), 3.24 (1H, dd, J 10.9, 4.6 Hz), 2.17 (3H, d, J 1.6 Hz), 2.03-1.97 (1H, m), 1.89-1.67 (1H, m). LCMS (ES⁺) RT 2.32 minutes, 463 (M+H)⁺.

EXAMPLE 57

3-[(2,4-Difluorophenyl)amino]-7-(4-fluorophenyl)-2-{[(3R)-3-hydroxypyrrolidin-1-yl]carbonyl}thieno[2,3-b]pyridin-6(7H)-one To a solution of Intermediate 73 (876 mg, 1.54 mmol) in EtOH (45 mL) was added 10% HCl(aq) (5 mL) and the reaction stirred at r.t. for 18 h. The reaction was diluted with EtOAc (100 mL), washed with sat. NaHCO₃(aq) (×2) and then brine. The organic layer was separated, dried (MgSO₄) and concentrated in vacuo. The crude product was purified by column chromatography (silica, 80% EtOAc in isohexane, loading the product in DCM) to give the title compound as a yellow solid (270 mg). NMR δH (CDCl₃) 7.36 (2H, m), 7.19 (3H, m), 6.99 (1H, m), 6.76 (1H, m), 6.72 (1H, m), 6.33 (1H, d, J 9.7 Hz), 4.45 (1H, m), 3.62 (4H, m), 1.85 (2H, m). LCMS (ES⁺) RT 3.04 minutes, 486 (M+H)⁺.

EXAMPLE 58

3-[(2,4-Difluorophenyl)amino]-7-(4-fluorophenyl)-2-{[(3S)-3-hydroxypyrrolidin-1-yl]carbonyl}thieno[2,3-b]pyridin-6(7H)-one To a solution of Intermediate 74 (767 mg, 1.35 mmol) in EtOH (45 mL) was added 10% HCl(aq) (5 mL) and the reaction stirred at r.t. for 18 h. The reaction was diluted with EtOAc (100 mL), washed with sat. NaHCO₃(aq) (×2) and then brine. The organic layer was separated, dried (MgSO₄) and concentrated in vacuo. The crude product was purified by column chromatography (silica, 80% EtOAc in isohexane, loading the product in DCM) to give the title compound as a yellow solid (304 mg). NMR δH (CDCl₃) 7.27 (2H, m), 7.20 (3H, m), 6.99 (1H, m), 6.85 (1H, m), 6.74 (1H, m), 6.36 (1H, d, J 9.7 Hz), 4.46 (1H, m), 3.75-3.50 (4H, m), 1.97 (2H, m). LCMS (ES⁺) RT 3.05 minutes, 486 (M+H)⁺.

EXAMPLE 59

3-[(4-Fluoro-3-methylphenyl)amino]-7-(4-fluorophenyl)-2-{[(3S)-3-hydroxypyrrolidin-1-yl]carbonyl}thieno[2,3-b]pyridin-6(7H)-one To a solution of Intermediate 75 (980 mg, 1.35 mmol) in EtOH (45 mL) was added 10% HCl(aq) (5 mL) and the reaction stirred at r.t. for 18 h. The reaction was diluted with EtOAc (100 mL), washed with sat. NaHCO₃(aq) (×2) and then brine. The organic layer was separated, dried (MgSO₄) and concentrated in vacuo. The crude product was purified by column chromatography (silica, 50-100% EtOAc in isohexane) to give the title compound as a pale yellow solid (654 mg). NMR δH (CDCl₃) 7.27 (2H, m), 7.14 (3H, m), 6.84-6.72 (3H, m), 6.26 (1H, d, J 9.7 Hz), 4.39 (1H, m), 3.62 (4H, m), 2.12 (3H, s), 1.88 (2H, m). LCMS (ES⁺) RT 3.12 minutes, 482 (M+H)⁺.

EXAMPLE 60

7-(2-Chlorophenyl)-3-[(4-fluoro-3-methylphenyl)amino]-2-{[(3S)-3-hydroxypyrrolidin-1-yl]carbonyl}thieno[2,3-b]pyridin-6(7H)-one The title compound was prepared from Intermediate 78 (623 mg, 1.07 mmol) following the procedure used for Example 58 to give a light yellow solid (253 mg). NMR δH (CDCl₃) 9.60 (1H, s), 7.64-7.57 (1H, m), 7.52-7.37 (3H, m), 7.25 (1H, d, J 9.8 Hz), 6.98-6.70 (3H, m), 6.34 (1H, d, J 9.8 Hz), 4.34 (1H, bs), 3.72-3.50 (4H, m), 3.08 (1H, bs), 2.22 (3H, s), 1.86 (2H, m). LCMS (ES⁺) RT 3.17 minutes, 498 (M+H)⁺.

EXAMPLE 61

7-(2-Chlorophenyl)-2-{[(3S)-3-hydroxypyrrolidin-1-yl]carbonyl}-3-[(3-methyl phenyl)amino]thieno[2,3-b]pyridin-6(7H)-one The title compound was prepared from Intermediate 79 (509 mg, 0.90 mmol) following the procedure used for Example 58. The crude product was purified by column chromatography (silica, 20% EtOAc in DCM) to give the title compound as a light yellow solid (253 mg). NMR δH (CDCl₃) 9.62 (1H, bs), 7.72-7.60 (1H, m), 7.58-7.25 (4H, m), 7.23-7.20 (1H, m), 7.02-6.86 (3H, m), 7.46 (1H, d, J 7.3 Hz), 4.35 (1H, bs), 3.74-3.50 (4H, m), 3.13 (1H, bs), 2.40 (3H, s), 1.96 (2H, bs). LCMS (ES⁺) RT 3.12 minutes, 480 (M+H)⁺.

EXAMPLE 62

7-(2-Chlorophenyl)-3-[(2,4-difluorophenyl)amino]-2-{[(3S)-3-hydroxypyrrolidin-1-yl]carbonyl}thieno[2,3-b]pyridin-6(7H)-one The title compound was prepared from Intermediate 80 (750 mg, 1.28 mmol) following the procedure used for Example 58 to give a light yellow solid (367 mg). NMR δH (CDCl₃) 9.56 (1H, s), 7.69-7.58 (1H, m), 7.43-7.38 (3H, m), 7.26 (1H, d, J 9.7 Hz), 7.07-6.97 (1H, m), 6.95-6.87 (1H, m), 6.80-6.78 (1H, m), 6.40 (1H, d, J 9.7 Hz), 4.35 (1H, s), 3.77-3.52 (4H, m), 3.00 (1H, bs), 1.90 (2H, s). LCMS (ES⁺) RT 3.10 minutes, 502 (M+H)⁺.

EXAMPLE 63

3-[(2,4-Difluorophenyl)amino]-2-{[(3S)-3-hydroxypyrrolidin-1-yl]carbonyl}-7-(4-methylphenyl)thieno[2,3-b]pyridin-6(7H)-one To a solution of Intermediate 81 (1.0 g, 2.31 mmol), tris(dibenzylideneacetone)dipalladium(0) (212 mg, 0.23 mmol, 10 mol %) and (+/−)-BINAP (288 mg, 0.46 mmol, 20 mol %) in toluene (50 mL) and under nitrogen was added 2,4-difluoroaniline (300 μL, 2.77 mmol) and caesium carbonate (1.05 g, 3.23 mmol, 1.4 equiv.). The reaction was heated at 100° C. under nitrogen for 4 days. The reaction mixture was diluted with EtOAc (80 mL), washed with water, brine (×2), dried (MgSO₄) and concentrated in vacuo. The crude product was purified by column chromatography (silica, 20% EtOAc in isohexane) to give the title compound as a white solid (123 mg). NMR δH (CDCl₃) 9.49 (1H, s), 7.33-7.30 (2H, m), 7.22-7.18 (2H, m), 7.16 (1H, d, J 9.7 Hz), 6.97 (1H, dd, J 9.0, 5.7 Hz), 6.86-6.81 (1H, m), 6.75-6.72 (1H, m), 6.35 (1H, d, J 9.7 Hz), 4.42 (1H, bs), 3.70-3.62 (3H, m), 3.56-3.53 (1H, m), 2.39 (3H, s), 1.97-1.85 (3H, m). LCMS (ES⁺) RT 3.13 minutes, 482 (M+H)⁺.

EXAMPLE 64

3-[(4-Fluoro-3-methylphenyl)amino]-2-{[(3S)-3-hydroxypyrrolidin-1-yl]carbonyl}-7-(4-methylphenyl)thieno[2,3-b]pyridin-6(7H)-one The title compound was prepared from Intermediate 81 (1.0 g, 2.3 mmol) and 4-fluoro-3-methylaniline (347 mg) following the method of Example 63. The crude product was purified by column chromatography (silica, 20% EtOAc in DCM) to give the title compound as a white solid (60 mg). NMR δH (CDCl₃) 9.56 (1H, bs), 7.33-7.30 (2H, m), 7.22-7.13 (3H, m), 6.89-6.78 (3H, m), 6.31 (1H, d, J 9.7 Hz), 4.44 (1H, m), 3.71-3.67 (3H, m), 3.63-3.57 (1H, m), 2.39 (3H, s), 2.17 (3H, d, J 1.8 Hz), 1.96-1.90 (2H, m), 1.59 (1H, bs). LCMS (ES⁺) RT 3.20 minutes, 478 (M+H)⁺.

EXAMPLE 65

3-[(2,4-Difluorophenyl)amino]-2-{[(3R)-3-hydroxypyrrolidin-1-yl]carbonyl}-7-(4-methylphenyl)thieno[2,3-b]pyridin-6(7H)-one The title compound was prepared from Intermediate 82 and 2,4-difluoroaniline following the method of Example 63 to give a white solid. NMR δH (CDCl₃) 7.44-7.21 (2H, m), 7.19-7.16 (3H, m), 6.99-6.97 (1H, m), 6.96-6.94 (1H, m), 6.92-6.87 (1H, m), 6.98 (1H, d, J 9.8 Hz), 4.44 (1H, bs), 3.71-3.63 (3H, m), 3.57-3.54 (1H, m), 2.39 (3H, s), 1.99-1.96 (2H, m). LCMS (ES⁺) RT 3.14 minutes, 482 (M+H)⁺.

EXAMPLE 66

3-[(4-Fluoro-3-methyl phenyl)amino]-2-{[(3R)-3-hydroxypyrrolidin-1-yl]carbonyl}-7-(4-methylphenyl)thieno[2,3-b]pyridin-6(7H)-one The title compound was prepared from Intermediate 82 (1.0 g, 2.3 mmol) and 4-fluoro-3-methylaniline (0.34 mL, 2.7 mmol) following the method of Example 63. The crude product was purified by column chromatography (silica, 70% EtOAc in isohexane) to give the title compound as a white solid (80 mg). NMR δH (CDCl₃) 7.32-7.30 (2H, m), 7.27-7.15 (3H, m), 6.88-6.77 (3H, m), 6.35 (1H, d, J 9.8 Hz), 4.42 (1H, bs), 3.73-3.62 (4H, m), 2.39 (3H, s), 2.17 (3H, s), 1.98-1.89 (2H, m). LCMS (ES⁺) RT 3.17 minutes, 478 (M+H)⁺.

EXAMPLE 67

3-[(4-Fluoro-3-methylphenyl)amino]-2-[(3-hydroxyazetidin-1-yl)carbonyl]-7-phenylthieno[2,3-b]pyridin-6(7H)-one Intermediate 85 (1.89 g, 3.55 mmol) was suspended in EtOH (76 mL) and 10% HCl (10 mL) and stirred at 40° C. for 36 h. The mixture was concentrated under reduced pressure and the residue redissolved in DCM/MeOH. Decolourising charcoal (0.09 g) was added and the suspension stirred for 30 min, filtered and reconcentrated to give crude product (1.58 g, 99%). This crude material was suspended in EtOH (8 mL) and stirred at r.t. for 4 h. The solid was isolated by filtration, washed with EtOH (3×2 mL) and dried in vacuo to yield the pure title compound (1.49 g, 94%). δH (CDCl₃) 9.60 (1H, s), 7.52-7.63 (3H, m), 7.38-7.41 (2H, m), 7.16-7.19 (1H, d), 6.86-6.98 (3H, m), 6.35-6.39 (1H, d), 4.36-4.42 (2H, m), 3.97-4.03 (2H, m), 2.33-2.43 (1H, m), 2.25 (3H, s). LCMS (ES⁺) RT 3.09 min, (M+H)⁺ 450.

EXAMPLE 68

2-[(4-Aminopiperidin-1-yl)carbonyl]-3-[(2,4-difluorophenyl)amino]-7-phenylthieno[2,3-b]pyridin-6(7H)-one Intermediate 86 (326 mg, 0.46 mmol) was dissolved in a solution of HCl in 1,4-dioxane (4.0N) and stirred under N₂ at r.t for 18 h. The crude product was concentrated in vacuo and triturated with Et₂O. Purification by chromatography (silica, 5% MeOH in DCM) gave the title compound as a light brown solid (175 mg, 80%). δH (DMSO-d6) 8.41 (1H, s), 7.86 (1H, d, J 9.6 Hz), 7.68-7.59 (5H, m), 7.31-7.26 (1H, m), 7.00-6.91 (2H, m), 6.89-6.53 (3H, m), 3.90-3.87 (2H, m), 3.10-2.95 (1H, m), 2.70-2.66 (2H, m), 1.75-1.72 (2H, m), 1.20-1.11 (2H, m). LCMS (ES⁺) RT 2.17 minutes, 481 (M+H)⁺.

EXAMPLE 69

2-[(3-Aminoazetidin-1-yl)carbonyl]-3-[(2,4-difluorophenyl)amino]-7-phenylthieno[2,3-b]pyridin-6(7H)-one From Intermediate 87 (386 mg, 0.70 mmol) by the method of Example 68 to give the title compound as an off-white solid (303 mg, 95%). δH (DMSO-d6) 9.29 (1H, s), 8.20-7.80 (2H, br s), 7.70-7.63 (3H, m), 7.57-7.53 (2H, m), 7.46-7.40 (1H, m), 7.32 (1H, d, J 9.7 Hz), 7.22-7.16 (1H, m), 7.12-7.05 (1H, m), 6.48 (1H, d, J 9.7 Hz), 4.33-4.25 (2H, m), 4.05-3.90 (3H, m). LCMS (ES⁺) RT 2.23 minutes, 453 (M+H)⁺.

EXAMPLE 70

3-[(2,4-Difluorophenyl)amino]-2-{[4-(dimethylamino)piperidin-1-yl]carbonyl}-7-phenylthieno[2,3-b]pyridin-6(7H)-one Example 68 (111 mg, 0.23 mmol), paraformaldehyde (70 mg, 0.56 mmol) and sodium cyanoborohydride (36 mg, 0.54 mmol) in MeOH (10 mL) were stirred at r.t. for 18 h. The reaction mixture was acidified using aq HCl (2N) and stirred for 20 min. The acidic mixture was neutralised with 10% aq. NaOH and extracted with DCM. The DCM extract was dried (Na₂SO₄) and concentrated in vacuo. The crude product was purified by chromatography (silica, 2% MeOH in DCM) to give the title compound as an off-white solid (30 mg, 25%). δH (CDCl₃) 8.00 (1H, s), 7.63-7.52 (3H, m), 7.42-7.40 (2H, m), 7.32 (1H, d, J 9.7 Hz), 7.00-6.90 (2H, m), 6.82-6.75 (1H, m), 6.48 (1H, d, J 9.7 Hz), 4.42-4.35 (2H, m), 2.95-2.80 (2H, m), 2.35-2.25 (1H, m), 1.90-1.75 (2H, m), 1.54 (6H, s), 1.40-1.30 (2H, m). LCMS (ES⁺) RT 2.20 minutes, 509 (M+H)⁺.

EXAMPLE 71

3-[(2,4-Difluorophenyl)amino]-2-{[3-(dimethylamino)azetidin-1-yl]carbonyl}-7-phenylthieno[2,3-b]pyridin-6(7H)-one From Example 69 (168 mg, 0.37 mmol), paraformaldehyde (103 mg, 0.82 mmol) and sodium cyanoborohydride (52 mg, 0.82 mmol) by the method of Example 70 to give the title compound as an off-white solid (130 mg, 70%). δH (DMSO-d6) 11.23 (1H, s), 7.71-7.62 (3H, m), 7.56-7.54 (2H, m), 7.44-7.39 (2H, m), 7.18-7.12 (1H, m), 7.08-7.04 (1H, m), 6.48 (1H, d, J 9.7 Hz), 4.15-3.95 (2H, m), 3.85-3.75 (2H, m), 3.10-3.00 (1H, m), 2.07 (6H, s). LCMS (ES$^+$) RT 2.26 minutes, 481 (M+H)$^+$.

EXAMPLE 72

3-[(2,4-Difluorophenyl)amino]-2-{[(3S)-3-(dimethylamino)pyrrolidin-1-yl]carbonyl}-7-phenylthieno[2,3-b]pyridin-6(7H)-one Intermediate 35 (1.0 g, 1.77 mmol) and (S)-3-dimethylaminopyrrolidine (222 mg, 1.95 mmol) were dissolved in DCM and stirred at r.t. for 18 h. The solution was washed with aq NaHCO$_3$ solution, dried (Na$_2$SO$_4$) and concentrated in vacuo. Chromatography (60:40 ethanol:water on reverse phase silica) gave the title compound (387 mg, 44%). δH (DMSO-d6) 8.82 (1H, br s), 7.67-7.59 (4H, m), 7.51 (2H, dd, J 1.78, 8.15 Hz), 7.36-7.28 (1H, m), 7.00-6.91 (2H, m), 6.48 (1H, d, J 9.6 Hz), 3.50-3.24 (3H, m), 2.98 (1H, t, J 9.7 Hz), 2.50-2.44 (1H, m), 2.03 (6H, s), 1.97-1.91 (1H, m), 1.50 (1H, t, J 9.7 Hz). LCMS (ES$^+$) RT 2.214 minutes, 495 (M+H)$^+$.

EXAMPLE 73

2-{[(3S)-3-(Dimethylamino)pyrrolidin-1-yl]carbonyl}-3-[(4-fluoro-3-methylphenyl)amino]-7-phenylthieno[2,3-b]pyridin-6(7H)-one From Intermediate 34 (1 g, 1.77 mmol) and (S)-3-dimethylaminopyrrolidine (222 mg, 1.94 mmol) by the method of Example 72. δH (DMSO-d6) 8.78 (1H, s), 7.67-7.56 (4H, m), 7.51 (2H, dd, J 8.2, 1.9 Hz), 7.00 (1H, t, J 9.11 Hz), 6.83-6.80 (1H, m), 6.75-6.70 (1H, m), 6.49 (1H, d, J 9.6 Hz), 3.44-3.20 (3H, m), 2.97 (1H, t, J 9.9 Hz), 2.42-2.35 (1H, m), 2.15 (3H, s), 1.99 (6H, s), 1.91-1.87 (1H, m), 1.47-1.40 (1H, m). LCMS (ES$^+$) RT 2.282 minutes, 491 (M+H)$^+$.

EXAMPLE 74

7-(2-Chlorophenyl)-3-[(2,4-difluorophenyl)amino]-2-{[(3R)-3-hydroxypyrrolidin-1-yl]carbonyl}thieno[2,3-b]pyridin-6(7H)-one From Intermediate 90 (3.0 g, 5.1 mmol) by the method of Example 62 to give the title compound as a pale yellow solid (1.61 g, 63%). δH (CDCl$_3$) 7.60-7.57 (1H, m), 7.48-7.33 (3H, m), 7.19 (2H, m), 7.00 (1H, dt, J 9.0, 5.7 Hz), 6.87-6.82 (1H, m), 6.77-6.73 (1H, m), 6.35 (1H, d, J 9.8 Hz), 4.43-4.40 (1H, m), 3.69-3.52 (4H, m), 1.97-1.91 (3H, m). LCMS (ES$^+$) RT 3.10 minutes, 502 (M+H)$^+$.

Preparation of Activated Human p38α for Inhibitor Assays

Purification of Human p38α

Human p38α, incorporating an N-terminal (His)6 tag, was expressed in baculovirus-infected High-Five™ cells (Invitrogen) according to the manufacturer's instructions. The cells were harvested 72 h post-infection and lysed in phosphate buffered saline (PBS) containing 1% (w/v) β-octylglucoside and Complete, EDTA-free™ protease inhibitors (Roche Molecular Biochemicals). The lysate was centrifuged at 35000×g for 30 min at 4° C. and the supernatant applied to a NiNTA™ column (Qiagen). Bound protein was eluted by 150 mM imidazole in PBS (after a wash with 15 mM imidazole in PBS) and directly applied to a HiTrap Q⇛ column (AP Biotech). Bound protein was eluted using a 20 column volume, 0 to 1M NaCl gradient. Fractions containing (His)6-p38 were aliquotted and stored at −70° C. prior to their activation.

Preparation of GST-MKK6EE-containing Lysates

E. coli (BL21 pLysS) expressing the constitutively activated form of human MKK6 fused with an N-terminal glutathione-S-transferase tag (GST-MKK6EE) were harvested by centrifugation and frozen at −70° C. Cells were lysed by resuspension in ¹/₁₀th the culture volume of PBS containing Complete, EDTA-free™ protease inhibitors followed by sonication on ice for 4×15 sec. Cell debris was removed by centrifugation at 35,000×g and the resultant supernatant stored in aliquots at −70° C.

Activation of (His)6-p38

0.45 mL of purified (His)6-p38 was incubated with 50 μL of the GST-MKK6EE-containing lysate for 30 min at 23° C. in the presence of 1 mM β-glycerophosphate, 10 mM MgCl$_2$ and 9 mM ATP. The extent of activation was monitored by mass spectrometric detection of the doubly-phosphorylated form of (His)6-p38, which routinely comprised greater than 90% of the final (His)6-p38 preparation. The activated (His)6-p38 was then diluted ×10 in PBS and repurified using the method described above. The concentration of purified, activated (His)6-p38 was measured by UV absorbance at 280 nm using A280, 0.1%=1.2 and the preparation stored in aliquots at −70° C. prior to its use in inhibitor assays.

p38 Inhibition Assays

Inhibition of Phosphorylation of Biotinylated Myelin Basic Protein (MBP)

The inhibition of p38 catalysed phosphorylation of biotinylated MBP is measured using a DELFIA based format. The assay was performed in a buffer comprising 20 mM HEPES (pH 7.4), 5 mM MgCl$_2$ and 3 mM DTT. For a typical IC$_{50}$ determination, biotinylated MBP (2.5 μM) was incubated at room temperature in a streptavidin-coated microtitre plate together with activated gst-p38 (10 nM) and ATP (1 μM) in the presence of a range of inhibitor concentrations (final concentration of DMSO is 2 percent). After fifteen minutes the reaction was terminated by the addition of EDTA (75 mM). The microtitre plate was then washed with Tris buffered saline (TBS), prior to the addition of 100 μl of anti-phospho MBP antibody (mouse) together with europium-labeled anti-mouse IgG antibody. After one hour at room temperature the plate was again washed in TBS followed by the addition of Enhancement solution (PerkinElmer Wallac). Fluorescence measurements were performed after a further fifteen minutes at room temperature.

IC$_{50}$ values are determined from the plot of log$_{10}$ inhibitor concentration (x-axis) versus percentage inhibition of the fluorescence generated by a control sample in the absence of inhibitor (y-axis).

Purification of Human Peripheral Blood Mononuclear Cells

Peripheral blood mononuclear cells (PBMC) were isolated from normal healthy volunteers. Whole blood was taken by venous puncture using heparinised vacutainers (Becton Dickinson), diluted 1 in 4 in RPMI 1640 (Gibco, UK) and centrifuged at 400 g for 35 min over a Ficoll-paque gradient (Amersham-Pharmacia Biotech, UK). Cells at the interface were removed and washed once followed by a low speed spin (250 g) to remove platelets. Cells were then resuspended in DMEM containing 10% FCS, penicillin 100 units ml$^{-1}$, streptomycin 50 μg ml$^{-1}$ and glutamine 2 mM (Gibco, UK).

Inhibitor Dilutions

Inhibitor stocks (20 mM) were kept as a frozen solution (−20° C.) in DMSO. Serial dilutions of inhibitors were performed in DMSO as 250-times concentrated stocks. Inhibitors were diluted 1 in 250 into tissue culture media, prewarmed to 37° C. and transferred to plates containing PBMC. PBMC and inhibitors were incubated together for 30 min prior to addition of LPS. Inhibitors used in whole blood assays were prepared according to a different regime. Using the same stock solution serial dilutions of inhibitors were performed in DMSO. Inhibitors were then diluted 1 in 500 straight into whole blood in a volume of 1 μl. Inhibitor was incubated with whole blood for 30 min prior to the addition of LPS.

LPS Stimulation of PBMC

PBMC were resuspended at a density of $2\times10^5$ cells/well in flat bottomed 96-well tissue culture treated plates. After the addition of inhibitor cells were stimulated with an optimal dose of LPS (*E coli* strain B5:055, Sigma, at a final concentration of 1 μg ml$^{-1}$) and incubated at 37° C. in 5% $CO_2$/95% air for 18 hours. TNF-α levels were measured from cell free supernatants by sandwich ELISA (BioSource #CHC1751).

LPS Stimulation of Whole Blood

Whole blood was taken by venous puncture using heparinised vacutainers (Becton Dickinson), and 500 μl of blood aliquoted into each well of a 24-well tissue culture treated plate. After the addition of inhibitor cells were stimulated with an optimal dose of LPS (*E coli* strain B5:055, Sigma, at a final concentration of 1 μg ml$^{-1}$) and incubated at 37° C. without $CO_2$ for 18 hours. TNF-α levels were measured from cell free supernatants by sandwich ELISA (BioSource #CHC1751).

Rat LPS Induced TNF Release

Male Lewis rats (180-200 g) are anaesthetised with Isofluor and injected i.v. with LPS* in a volume of 0.5 ml sterile saline. After 90 minutes blood is collected into EDTA tubes for preparation of plasma samples. Plasma is stored at –70° C. prior to assay for TNF-α by commercial ELISA.

Rat CIA

Female Lewis rats (180-200 g) are anaesthetised with Isofluor and immunised i.d. at the base of the tail with 2×100 μl of emulsion containing 4 mg/ml bovine collagen II in 0.01M acetic acid and Freund's Incomplete Adjuvant at a ratio of 1:1. A polyarthritis develops with onset from about 13 days post sensitisation. The disease is mainly confined to the ankles and is quantified by plethysmometry. Results are expressed as change in paw volume over time.

In the p38 inhibitor assays described above compounds of the invention have $IC_{50}$ values of around 1 μM and below. The compounds of the invention are clearly potent inhibitors of p38 kinase, especially p38α kinase.

The invention claimed is:

1. A compound of formula (1):

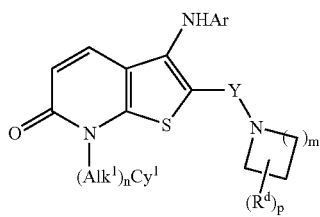

wherein:
Y is a linking group —C(O)— or —S(O)$_2$—;
n is zero or the integer 1;
m is the integer 1, 2, 3 or 4;
p is the integer 1, 2, 3 or 4;
$R^d$ is —OH, -(Alk$^2$)OH, —OR$^1$, -(Alk$^2$)OR$^1$, —NR$^2$R$^3$, -(Alk$^2$)NR$^2$R$^3$ or a straight or branched C$_{1-6}$ alkyl group;

Alk$^2$ is a straight or branched C$_{1-4}$ alkylene chain;
R$^1$ is a straight or branched C$_{1-6}$ alkyl group;
R$^2$ and R$^3$, which may be the same or different, are each independently a hydrogen atom or a straight or branched C$_{1-6}$ alkyl group;
Alk$^1$ is a straight or branched C$_{1-4}$ alkylene chain;
Cy$^1$ is an optionally substituted cycloaliphatic, aromatic or heteroaromatic group; and
Ar is an optionally substituted aromatic or heteroaromatic group; or a salt or N-oxide thereof.

2. A compound as claimed in claim 1 wherein $R^d$ is —OH, -(Alk$^2$)OH, -(Alk$^2$)OR$^1$, —NR$^2$R$^3$ or -(Alk$^2$)NR$^2$R$^3$.

3. A compound as claimed in claim 1 wherein Alk$^2$ is —CH$_2$— or —C(CH$_3$)$_2$—.

4. A compound as claimed in claim 1 wherein R$^1$ is methyl.

5. A compound as claimed in claim 1 wherein R$^2$ is hydrogen or methyl.

6. A compound as claimed in claim 1 wherein R$^3$ is hydrogen or methyl.

7. A compound as claimed in claim 1 wherein Cy$^1$ is phenyl, fluorophenyl, chlorophenyl, methylphenyl or cyclopropyl.

8. A compound as claimed in claim 1 wherein Ar is phenyl, difluorophenyl, (chloro)(fluoro)phenyl, (fluoro)(methyl)phenyl, chlorophenyl, cyanophenyl or methylphenyl.

9. A compound as claimed in claim 1 that is
3-[(2,4-Difluorophenyl)amino]-2-{[(2R)-2-(hydroxymethyl)pyrrolidin-1-yl]carbonyl}-7-phenylthieno[2,3-b]pyridin-6(7H)-one;
2-{[(2R)-2-(Hydroxymethyl)pyrrolidin-1-yl]carbonyl}-3-[(3-methylphenyl)amino]-7-phenylthieno[2,3-b]pyridin-6(7H)-one;
3-[(3-Chlorophenyl)amino]-2-{[(2R)-2-(hydroxymethyl)pyrrolidin-1-yl]carbonyl}-7-phenylthieno[2,3-b]pyridin-6(7H)-one;
3-[(2,4-Difluorophenyl)amino]-2-{[(2R)-2-(hydroxymethyl)pyrrolidin-1-yl]carbonyl}-7-(4-methylphenyl)thieno[2,3-b]pyridin-6(7H)-one;
3-[(4-Fluoro-3-methylphenyl)amino]-2-{[(2R)-2-(hydroxymethyl)-pyrrolidin-1-yl]carbonyl}-7-(4-methylphenyl)thieno[2,3-b]pyridin-6(7H)-one;
2-{[(2R)-2-(Hydroxymethyl)pyrrolidin-1-yl]carbonyl}-7-(4-methylphenyl)-3-[(3-methylphenyl)amino]thieno[2,3-b]pyridin-6(7H)-one;
3-[(2,4-Difluorophenyl)amino]-7-(4-fluorophenyl)-2-{[(2R)-2-(hydroxymethyl)pyrrolidin-1-yl]carbonyl}thieno[2,3-b]pyridin-6(7H)-one;
3-[(4-Fluoro-3-methylphenyl)amino]-7-(4-fluorophenyl)-2-{[(2R)-2-(hydroxymethyl)pyrrolidin-1-yl]carbonyl}thieno[2,3-b]pyridin-6(7H)-one;
7-(2-Chlorophenyl)-3-[(4-fluoro-3-methylphenyl)amino]-2-{[(2R)-2-(hydroxymethyl)pyrrolidin-1-yl]carbonyl}thieno[2,3-b]pyridin-6(7H)-one;
7-(2-Chlorophenyl)-3-[(2,4-difluorophenyl)amino]-2{[(2R)-2-(hydroxymethyl)pyrrolidin-1-yl]carbonyl}thieno[2,3-b]pyridin-6(7H)-one;
3-[(2-Chlorophenyl)amino]-2-{[(2R)-2-(hydroxymethyl)pyrrolidin-1-yl]carbonyl}-7-phenylthieno[2,3-b]pyridin-6(7H)-one;
3-[(2-Chlorophenyl)amino]-2-{[(2S)-2-(hydroxymethyl)pyrrolidin-1-yl]carbonyl}-7-phenylthieno[2,3-b]pyridin-6(7H)-one;
3-Anilino-2-{[(2R)-2-(hydroxymethyl)pyrrolidin-1-yl]carbonyl}-7-phenylthieno[2,3-b]pyridin-6(7H)-one;
3-Anilino-2-{[(2S)-2-(hydroxymethyl)pyrrolidin-1-yl]carbonyl}-7-phenylthieno[2,3-b]pyridin-6(7H)-one;

3[(2,4-Difluorophenyl)amino]-2-{[(2S)-2-(hydroxymethyl)pyrrolidin-1-yl]carbonyl}-7-phenylthieno[2,3-b]pyridin-6(7H)-one;

3-Anilino-2-{[(2S)-2-(methoxymethyl)pyrrolidin-1-yl]carbonyl}-7-phenylthieno[2,3-b]pyridin-6(7H)-one;

3-Anilino-2-{[(2R)-2-(methoxymethyl)pyrrolidin-1-yl]carbonyl}-7-phenylthieno[2,3-b]pyridin-6(7H)-one;

7-(4-Chlorophenyl)-3-[(4-fluoro-3-methylphenyl)amino]-2-{[(2R)-2-(hydroxymethyl)pyrrolidin-1-yl]carbonyl}thieno[2,3-b]pyridin-6(7H)-one;

3-[(4-Fluoro-3-methylphenyl)amino]-2-{[(2S)-2-(hydroxymethyl)-pyrrolidin-1-yl]carbonyl}-7-(3-methylphenyl)thieno[2,3-b]pyridin-6(7H)-one;

2-{[(2R)-2-(Hydroxymethyl)pyrrolidin-1-yl]carbonyl}-7-(3-methylphenyl)-3-[(3-methylphenyl)amino]thieno[2,3-b]pyridin-6(7H)-one;

3-[(4-Fluoro-3-methylphenyl)amino]-2-{[(2R)-2-(hydroxymethyl)-pyrrolidin-1-yl]carbonyl}-7-(3-methylphenyl)thieno[2,3-b]pyridin-6(7H)-one;

3-[(3-Chloro-4-fluorophenyl)amino]-2-{[(2R)-2-(hydroxymethyl)-pyrrolidin-1-yl]carbonyl}-7-phenylthieno[2,3-b]pyridin-6(7H)-one;

3-[(3-Chloro-4-fluorophenyl)amino]-2-{[(2S)-2-(hydroxymethyl)-pyrrolidin-1-yl]carbonyl}-7-phenylthieno[2,3-b]pyridin-6(7H)-one;

3-[(4-Fluoro-3-methylphenyl)amino]-2-{[(2R)-2-(hydroxymethyl)-pyrrolidin-1-yl]carbonyl}-7-phenylthieno[2,3-b]pyridin-6(7H)-one;

3-[(4-Fluoro-3-methylphenyl)amino]-2-{[(2S)-2-(hydroxymethyl)-pyrrolidin-1-yl]carbonyl}-7-phenylthieno[2,3-b]pyridin-6(7H)-one;

3-[(2,4-Difluorophenyl)amino]-2-{[(3S)-3-hydroxypyrrolidin-1-yl]carbonyl}-7-phenylthieno[2,3-b]pyridin-6(7H)-one;

3-[(2,4-Difluorophenyl)amino]-2-{[(3R)-3-hydroxypyrrolidin-1-yl]carbonyl}-7-phenylthieno[2,3-b]pyridin-6(7H)-one;

3-[(4-Fluoro-3-methylphenyl)amino]-2-{[(3S)-3-hydroxypyrrolidin-1-yl]carbonyl}-7-phenylthieno[2,3-b]pyridin-6(7H)-one;

3-[(4-Fluoro-3-methylphenyl)amino]-2-{[(3R)-3-hydroxypyrrolidin-1-yl]carbonyl}-7-phenylthieno[2,3-b]pyridin-6(7H)-one;

3-[(2,4-Difluorophenyl)amino]-2-{[(3S,4S)-3,4-dihydroxypyrrolidin-1-yl]carbonyl}-7-phenylthieno[2,3-b]pyridin-6(7H)-one;

3-[(2,4-Difluorophenyl)amino]-2-[(3-hydroxyazetidin-1-yl)carbonyl]-7-phenylthieno[2,3-b]pyridin-6(7H)-one;

3-[(2,4-Difluorophenyl)amino]-2-{[(2S)-2-(1-hydroxy-1-methylethyl)pyrrolidin-1-yl]carbonyl}-7-phenylthieno[2,3-b]pyridin-6(7H)-one;

3-[(2,4-Difluorophenyl)amino]-2-{[(2R)-2-(1-hydroxy-1-methylethyl)pyrrolidin-1-yl]carbonyl}-7-phenylthieno[2,3-b]pyridin-6(7H)-one;

3-[(2-Cyanophenyl)amino]-2-{[(2S)-2-(hydroxymethyl)pyrrolidin-1-yl]carbonyl}-7-phenylthieno[2,3-b]pyridin-6(7H)-one;

3-[(2-Cyanophenyl)amino]-2-{[(2R)-2-(hydroxymethyl)pyrrolidin-1-yl]carbonyl}-7-phenylthieno[2,3-b]pyridin-6(7H)-one;

3-Anilino-7-(cyclopropylmethyl)-2-{[(2R)-2-(hydroxymethyl)pyrrolidin-1-yl]carbonyl}thieno[2,3-b]pyridin-6(7H)-one;

3-[(3-Cyanophenyl)amino]-2-{[(2R)-2-(hydroxymethyl)pyrrolidin-1-yl]carbonyl}-7-phenylthieno[2,3-b]pyridin-6(7H)-one;

3-[(2,4-Difluorophenyl)amino]-2-{[2R)-2-(hydroxymethyl)pyrrolidin-1-yl]sulfonyl}-7-phenylthieno[2,3-b]pyridin-6(7H)-one;

2-{[(3R)-3-Aminopyrrolidin-1-yl]carbonyl}-3-[(2,4-difluorophenyl)amino]-7-phenylthieno[2,3-b]pyridin-6(7H)-one;

2-{[(2S)-2-(Aminomethyl)pyrrolidin-1-yl]carbonyl}-3-[(2,4-difluorophenyl)amino]-7-phenylthieno[2,3-b]pyridin-6(7H)-one;

2-{[(2R)-2-(Aminomethyl)pyrrolidin-1-yl]carbonyl}-3-[(2,4-difluorophenyl)amino]-7-phenylthieno[2,3-b]pyridin-6(7H)-one;

3-[(2,4-Difluorophenyl)amino]-2-{[(3R)-3-(dimethylamino)pyrrolidin-1-yl]carbonyl}-7-phenylthieno[2,3-b]pyridin-6(7H)-one;

3-[(2,4-Difluorophenyl)amino]-2-[(4-hydroxypiperidin-1-yl)carbonyl]-7-phenylthieno[2,3-b]pyridin-6(7H)-one;

rac-3-[(2,4-Difluorophenyl)amino]-2-[(3-hydroxypiperidin-1-yl)carbonyl]-7-phenylthieno[2,3-b]pyridin-6(7H)-one;

2-{[(3R)-3-Aminopyrrolidin-1-yl]carbonyl}-3-[(4-fluoro-3-methylphenyl)amino]-7-phenylthieno[2,3-b]pyridin-6(7H)-one;

2-{[(2S)-2-(Aminomethyl)pyrrolidin-1-yl]carbonyl}-3-[(4-fluoro-3-methylphenyl)amino]-7-phenylthieno[2,3-b]pyridin-6(7H)-one;

3-[(4-Fluoro-3-methylphenyl)amino]-2-{[(3R)-3-(dimethylamino)-pyrrolidin-1-yl]carbonyl}-7-phenylthieno[2,3-b]pyridin-6(7H)-one;

3-[(2,4-Difluorophenyl)amino]-2-{[(3R,4R)-3,4-dihydroxypyrrolidin-1-yl]carbonyl}-7-phenylthieno[2,3-b]pyridin-6(7H)-one;

3-[(2,4-Difluorophenyl)amino]-2-{[(3R*,4S*)-3,4-dihydroxypyrrolidin-1-yl]carbonyl}-7-phenylthieno[2,3-b]pyridin-6(7H)-one;

3-[(2-Cyanophenyl)amino]-2-{[(3S)-3-hydroxypyrrolidin-1-yl]carbonyl}-7-phenylthieno[2,3-b]pyridin-6(7H)-one;

3-[(2-Cyanophenyl)amino]-2-{[(3R)-3-hydroxypyrrolidin-1-yl]carbonyl}-7-phenylthieno[2,3-b]pyridin-6(7H)-one;

rac-2-{[3-Aminopyrrolidin-1-yl]carbonyl}-3-[(2,4-difluorophenyl)amino]-7-phenylthieno[2,3-b]pyridin-6(7H)-one;

2-{[(3S)-3-Aminopyrrolidin-1-yl]carbonyl}-3-[(2,4-difluorophenyl)amino]-7-phenylthieno[2,3-b]pyridin-6(7H)-one;

2-{[(3S)-3-Aminopyrrolidin-1-yl]carbonyl}-3-[(4-fluoro-3-methylphenyl)amino]-7-phenylthieno[2,3-b]pyridin-6(7H)-one;

3-[(2,4-Difluorophenyl)amino]-7-(4-fluorophenyl)-2-{[(3R)-3-hydroxypyrrolidin-1-yl]carbonyl}thieno[2,3-b]pyridin-6(7H)-one;

3-[(2,4-Difluorophenyl)amino]-7-(4-fluorophenyl)-2-{[(3S)-3-hydroxypyrrolidin-1-yl]carbonyl}thieno[2,3-b]pyridin-6(7H)-one;

3-[(4-Fluoro-3-methylphenyl)amino]-7-(4-fluorophenyl)-2-{[(3S)-3-hydroxypyrrolidin-1-yl]carbonyl}thieno[2,3-b]pyridin-6(7H)-one;

7-(2-Chlorophenyl)-3[(4-fluoro-3-methylphenyl)amino]-2-{[(3S)-3-hydroxypyrrolidin-1-yl]carbonyl}thieno[2,3-b]pyridin-6(7H)-one;

7-(2-Chlorophenyl)-2-{[(3S)-3-hydroxypyrrolidin-1-yl]carbonyl}-3-[(3-methylphenyl)amino]thieno[2,3-b]pyridin-6(7H)-one;

7-(2-Chlorophenyl)-3-[(2,4-difluorophenyl)amino]-2-{[(3S)-3-hydroxypyrrolidin-1-yl]carbonyl}thieno[2,3-b]pyridin-6(7H)-one;

3-[(2,4-Difluorophenyl)amino]-2-{[(3S)-3-hydroxypyrrolidin-1-yl]carbonyl}-7-(4-methylphenyl)thieno[2,3-b]pyridin-6(7H)-one;

3-[(4-Fluoro-3-methylphenyl)amino]-2-{[(3S)-3-hydroxypyrrolidin-1-yl]carbonyl}-7-(4-methylphenyl)thieno[2,3-b]pyridin-6(7H)-one;

3-[(2,4-Difluorophenyl)amino]-2-{[(3R)-3-hydroxypyrrolidin-1-yl]carbonyl}-7-(4-methylphenyl)thieno[2,3-b]pyridin-6(7H)-one;

3-[(4-Fluoro-3-methylphenyl)amino]-2-{[(3R)-3-hydroxypyrrolidin-1-yl]carbonyl}-7-(4-methylphenyl)thieno[2,3-b]pyridin-6(7H)-one;

3-[(4-Fluoro-3-methylphenyl)amino]-2-[(3-hydroxyazetidin-1-yl)carbonyl]-7-phenylthieno[2,3-b]pyridin-6(7H)-one;

2-[(4-Aminopiperidin-1-yl)carbonyl]-3-[(2,4-difluorophenyl)amino]-7-phenylthieno[2,3-b]pyridin-6(7H)-one;

2-[(3-Aminoazetidin-1-yl)carbonyl]-3-[(2,4-difluorophenyl)amino]-7-phenylthieno[2,3-b]pyridin-6(7H)-one;

3-[(2,4-Difluorophenyl)amino]-2-{[4-(dimethylamino)piperidin-1-yl]carbonyl}-7-phenylthieno[2,3-b]pyridin-6(7H)-one;

3-[(2,4-Difluorophenyl)amino]-2-{[3-(dimethylamino)azetidin-1-yl]carbonyl}-7-phenylthieno[2,3-b]pyridin-6(7H)-one;

3-[(2,4-Difluorophenyl)amino]-2-{[(3S)-3-(dimethylamino)pyrrolidin-1-yl]carbonyl}-7-phenylthieno[2,3-b]pyridin-6(7H)-one;

2-{[(3S)-3-(Dimethylamino)pyrrolidin-1-yl]carbonyl}-3-[(4-fluoro-3-methylphenyl)amino]-7-phenylthieno[2,3-b]pyridin-6(7H)-one; or 7-(2-Chlorophenyl)-3-[(2,4-difluorophenyl)amino]-2-{[(3R)-3-hydroxypyrrolidin-1-yl]carbonyl}thieno[2,3-b]pyridin-6(7H)-one.

10. A pharmaceutical composition comprising a compound of claim 1, or a pharmaceutically acceptable salt or N-oxide thereof, in association with a pharmaceutically acceptable carrier.

11. A method for inhibiting p38α MAP kinase, which comprises administering to a patient in need thereof a compound of claim 1, or a pharmaceutically acceptable salt or N-oxide thereof.

* * * * *